(12) United States Patent
Diduch et al.

(10) Patent No.: US 10,856,966 B2
(45) Date of Patent: Dec. 8, 2020

(54) BICEPS TENODESIS IMPLANTS AND DELIVERY TOOLS

(71) Applicant: DePuy Synthes Products, Inc., Raynham, MA (US)

(72) Inventors: David R. Diduch, Charlottesville, VA (US); Mark H. Getelman, Tarzana, CA (US); Jacob A. Marks, Foxboro, MA (US); Gerome Miller, Randolph, MA (US); Matthew J. Ravenscroft, Mere (GB); Mehmet Z. Sengun, Canton, MA (US); Howard C. Tang, Boston, MA (US); Paul P. Weitzel, Newton, MA (US); Gregory R. Whittaker, Stoneham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 1487 days.

(21) Appl. No.: 14/610,602

(22) Filed: Jan. 30, 2015

(65) Prior Publication Data

US 2016/0113756 A1    Apr. 28, 2016

Related U.S. Application Data

(60) Provisional application No. 62/067,701, filed on Oct. 23, 2014.

(51) Int. Cl.
*A61F 2/08* (2006.01)
*A61B 17/88* (2006.01)

(52) U.S. Cl.
CPC ........ *A61F 2/0811* (2013.01); *A61B 17/8894* (2013.01); *A61F 2/0805* (2013.01);
(Continued)

(58) Field of Classification Search
CPC .................. A61B 17/86; A61F 2/0811; A61F 2002/0835; A61F 2002/0841; A61F 2002/0858

See application file for complete search history.

(56) References Cited

U.S. PATENT DOCUMENTS 651,949 A    6/1900  Lillie
775,427 A    11/1904 Lusted
(Continued)

FOREIGN PATENT DOCUMENTS

AU    2013201310 B2   5/2015
CN    1378439 A       11/2002
(Continued)

OTHER PUBLICATIONS

U.S. Appl. No. 14/693,276, filed Apr. 22, 2015, Biceps Repair Device.
(Continued)

*Primary Examiner* — Nicholas W Woodall

(57) ABSTRACT

Methods and devices are provided for anchoring a ligament or tendon to bone. In one embodiment, a surgical implant is provided having a sheath and an expander that is received within the sheath. Various delivery tools, including a sheath inserter and a driver, are also provided. In use, the sheath inserter can be used to position a tendon within a prepared bone hole, and it can be used to deliver the sheath with a guidewire coupled thereto into the bone hole. The driver can be provided for delivering the expander into the sheath. A loader can optionally be used to load the driver and expander onto the guidewire coupled to the implanted sheath.

17 Claims, 47 Drawing Sheets

(52) U.S. Cl.
CPC .............. *A61F 2002/0835* (2013.01); *A61F 2002/0841* (2013.01); *A61F 2002/0858* (2013.01); *A61F 2002/0888* (2013.01)

(56) References Cited

U.S. PATENT DOCUMENTS

| | | | |
|---|---|---|---|
| 1,426,320 A | 8/1922 | Reid | |
| 1,925,385 A | 9/1933 | Humes et al. | |
| 2,243,717 A | 5/1941 | Godoy | |
| 2,288,584 A | 6/1942 | Longfellow | |
| 2,381,050 A | 8/1945 | Hardinge | |
| 2,484,655 A | 10/1949 | Shreve | |
| 3,073,189 A | 1/1963 | Paige | |
| 3,089,359 A | 5/1963 | Poulin | |
| 3,103,926 A * | 9/1963 | Cochran ............. | A61B 17/72 606/104 |
| 3,130,763 A | 4/1964 | Bernard et al. | |
| 3,298,410 A | 1/1967 | Noboru | |
| 4,503,737 A | 3/1985 | DiGiovanni | |
| 4,512,344 A | 4/1985 | Barber | |
| 4,592,346 A | 6/1986 | Jurgutis | |
| 4,640,271 A | 2/1987 | Lower | |
| 4,641,640 A | 2/1987 | Griggs | |
| 4,687,392 A | 8/1987 | Bidwell | |
| 4,704,055 A | 11/1987 | Guhring | |
| 4,711,232 A | 12/1987 | Fischer et al. | |
| 4,773,417 A | 9/1988 | Moore et al. | |
| 4,851,005 A | 7/1989 | Hunt et al. | |
| 4,858,810 A | 8/1989 | Intlekofer et al. | |
| 4,871,289 A | 10/1989 | Choiniere | |
| 4,901,717 A | 2/1990 | Moore et al. | |
| 4,919,130 A | 4/1990 | Stoy et al. | |
| 4,921,383 A | 5/1990 | Fischer | |
| 4,950,270 A | 8/1990 | Bowman et al. | |
| 4,960,420 A | 10/1990 | Goble et al. | |
| 4,976,715 A | 12/1990 | Bays et al. | |
| 4,988,351 A | 1/1991 | Paulos et al. | |
| 5,026,376 A | 6/1991 | Greenberg | |
| 5,029,573 A | 7/1991 | Chow | |
| 5,105,690 A | 4/1992 | Lazzara et al. | |
| 5,116,337 A | 5/1992 | Johnson | |
| 5,129,906 A | 7/1992 | Ross et al. | |
| 5,180,384 A | 1/1993 | Mikhail | |
| 5,209,756 A | 5/1993 | Seedhom et al. | |
| 5,211,647 A | 5/1993 | Schmieding | |
| 5,226,714 A | 7/1993 | Wright | |
| 5,226,890 A | 7/1993 | Ianniruberto et al. | |
| 5,234,435 A | 8/1993 | Seagrave, Jr. | |
| 5,236,445 A | 8/1993 | Hayhurst et al. | |
| 5,242,418 A | 9/1993 | Weinstein | |
| 5,258,012 A | 11/1993 | Luscombe et al. | |
| 5,266,075 A | 11/1993 | Clark et al. | |
| 5,273,024 A | 12/1993 | Menon et al. | |
| 5,290,296 A | 3/1994 | Phillips | |
| 5,290,297 A | 3/1994 | Phillips | |
| 5,314,427 A | 5/1994 | Goble et al. | |
| 5,320,626 A | 6/1994 | Schmieding | |
| 5,325,868 A | 7/1994 | Kimmelstiel | |
| 5,325,883 A | 7/1994 | Orr | |
| 5,352,229 A | 10/1994 | Goble et al. | |
| 5,352,231 A | 10/1994 | Brumfield et al. | |
| 5,380,334 A | 1/1995 | Torrie et al. | |
| 5,383,878 A | 1/1995 | Roger et al. | |
| 5,385,541 A | 1/1995 | Kirsch et al. | |
| 5,409,493 A | 4/1995 | Greenberg | |
| 5,425,490 A | 6/1995 | Goble et al. | |
| 5,425,733 A | 6/1995 | Schmieding | |
| 5,445,642 A | 8/1995 | McNulty et al. | |
| 5,454,811 A | 10/1995 | Huebner | |
| 5,456,721 A | 10/1995 | Legrand | |
| 5,478,329 A | 12/1995 | Ternamian | |
| 5,505,735 A | 4/1996 | Li | |
| 5,527,341 A | 6/1996 | Gogolewski et al. | |
| 5,571,104 A | 11/1996 | Li | |
| 5,601,558 A | 2/1997 | Torrie et al. | |
| 5,601,562 A | 2/1997 | Wolf et al. | |
| 5,607,432 A | 3/1997 | Fucci | |
| 5,630,805 A | 5/1997 | Ternamian | |
| 5,632,748 A | 5/1997 | Beck, Jr. et al. | |
| 5,651,790 A | 7/1997 | Resnick et al. | |
| 5,653,763 A | 8/1997 | Errico et al. | |
| 5,655,330 A | 8/1997 | Parsons, III | |
| 5,658,289 A | 8/1997 | Boucher et al. | |
| 5,660,186 A | 8/1997 | Bachir | |
| 5,662,655 A | 9/1997 | Laboureau et al. | |
| 5,662,657 A | 9/1997 | Carn | |
| 5,669,925 A | 9/1997 | Saunders | |
| 5,676,499 A | 10/1997 | Tukala | |
| D388,171 S | 12/1997 | Fekete | |
| 5,700,266 A | 12/1997 | Harryman, II | |
| 5,702,398 A | 12/1997 | Tarabishy | |
| 5,713,903 A | 2/1998 | Sander et al. | |
| 5,720,753 A | 2/1998 | Sander et al. | |
| 5,738,666 A | 4/1998 | Watson et al. | |
| 5,746,743 A | 5/1998 | Greenberg | |
| 5,779,707 A | 7/1998 | Bertholet et al. | |
| 5,782,865 A | 7/1998 | Gratz | |
| RE36,020 E | 12/1998 | Moore et al. | |
| 5,895,351 A | 4/1999 | Nottage et al. | |
| 5,897,565 A | 4/1999 | Foster | |
| 5,899,906 A | 5/1999 | Schenk | |
| 5,899,938 A | 5/1999 | Sklar et al. | |
| 5,904,685 A | 5/1999 | Walawalkar | |
| 5,906,632 A | 5/1999 | Bolton | |
| 5,941,882 A | 8/1999 | Jammet et al. | |
| 5,948,000 A | 9/1999 | Larsen et al. | |
| 5,948,001 A | 9/1999 | Larsen | |
| 5,957,953 A | 9/1999 | DiPoto et al. | |
| 5,961,520 A | 10/1999 | Beck, Jr. et al. | |
| 5,961,521 A | 10/1999 | Roger | |
| 5,968,078 A | 10/1999 | Gratz | |
| 5,993,458 A | 11/1999 | Vaitekunas et al. | |
| 6,024,758 A | 2/2000 | Thal | |
| 6,027,523 A | 2/2000 | Schmieding | |
| 6,077,267 A | 6/2000 | Huene | |
| 6,117,139 A | 9/2000 | Shino | |
| 6,123,711 A | 9/2000 | Winters | |
| 6,143,016 A | 11/2000 | Bleam et al. | |
| 6,143,017 A | 11/2000 | Thal | |
| 6,221,107 B1 | 4/2001 | Steiner et al. | |
| 6,231,606 B1 | 5/2001 | Graf et al. | |
| 6,251,119 B1 | 6/2001 | Addis | |
| 6,270,518 B1 | 8/2001 | Pedlick et al. | |
| 6,283,948 B1 | 9/2001 | McKernan et al. | |
| 6,306,138 B1 | 10/2001 | Clark et al. | |
| 6,319,270 B1 | 11/2001 | Grafton et al. | |
| 6,325,805 B1 | 12/2001 | Ogilvie et al. | |
| 6,379,361 B1 | 4/2002 | Beck, Jr. et al. | |
| 6,405,863 B1 | 6/2002 | Dhindsa | |
| 6,443,956 B1 | 9/2002 | Ray | |
| 6,464,706 B1 | 10/2002 | Winters | |
| 6,517,519 B1 | 2/2003 | Rosen et al. | |
| 6,517,564 B1 | 2/2003 | Grafton et al. | |
| 6,533,816 B2 | 3/2003 | Sklar | |
| 6,544,281 B2 | 4/2003 | ElAttrache et al. | |
| 6,554,862 B2 | 4/2003 | Hays et al. | |
| 6,558,389 B2 | 5/2003 | Clark et al. | |
| 6,562,044 B1 | 5/2003 | Cooper | |
| 6,579,295 B1 | 6/2003 | Supinski | |
| 6,592,587 B1 | 7/2003 | Roger | |
| 6,599,290 B2 | 7/2003 | Bailey et al. | |
| 6,613,065 B2 | 9/2003 | Lajtai | |
| 6,632,245 B2 | 10/2003 | Kim | |
| 6,663,605 B2 | 12/2003 | Chan | |
| 6,673,115 B2 | 1/2004 | Resch et al. | |
| 6,702,817 B2 | 3/2004 | Beger et al. | |
| 6,712,822 B2 | 3/2004 | Re et al. | |
| 6,755,815 B2 | 6/2004 | Schultz | |
| 6,755,836 B1 | 6/2004 | Lewis | |
| 6,780,188 B2 | 8/2004 | Clark et al. | |
| 6,827,722 B1 | 12/2004 | Schoenefeld | |
| 6,871,740 B1 | 3/2005 | Cao | |
| 6,875,214 B2 | 4/2005 | Supinski | |
| 6,875,216 B2 | 4/2005 | Wolf | |

(56) References Cited

U.S. PATENT DOCUMENTS

| | | | |
|---|---|---|---|
| 6,887,271 B2 | 5/2005 | Justin et al. |
| 6,939,379 B2 | 9/2005 | Sklar |
| 6,942,664 B1 | 9/2005 | Voor et al. |
| 6,955,678 B2 | 10/2005 | Gabriel et al. |
| 7,074,203 B1 | 7/2006 | Johanson et al. |
| 7,083,647 B1 | 8/2006 | Sklar et al. |
| 7,104,999 B2 | 9/2006 | Overaker |
| 7,204,839 B2 | 4/2007 | Dreyfuss et al. |
| 7,235,060 B2 | 6/2007 | Kraus |
| 7,261,716 B2 | 8/2007 | Strobel et al. |
| 7,309,346 B2 | 12/2007 | Martinek |
| 7,309,355 B2 | 12/2007 | Donnelly et al. |
| 7,329,272 B2 | 2/2008 | Burkhart et al. |
| 7,341,591 B2 | 3/2008 | Grinberg |
| 7,341,592 B1 | 3/2008 | Walters et al. |
| 7,413,542 B2 | 8/2008 | Kucklick et al. |
| 7,442,202 B2 | 10/2008 | Dreyfuss |
| 7,468,074 B2 | 12/2008 | Caborn et al. |
| 7,476,228 B2 | 1/2009 | Abdou |
| 7,481,830 B2 | 1/2009 | Wall et al. |
| 7,556,638 B2 | 7/2009 | Morgan et al. |
| 7,572,283 B1 | 8/2009 | Meridew |
| 7,588,575 B2 | 9/2009 | Colleran et al. |
| 7,611,521 B2 | 11/2009 | Lubbers et al. |
| 7,651,528 B2 * | 1/2010 | Montgomery ..... A61B 17/0401 |
| | | | 623/13.14 |
| 7,697,861 B2 | 4/2010 | Shindo et al. |
| D615,572 S | 5/2010 | Harpaz |
| 7,713,300 B2 | 5/2010 | Meridew et al. |
| 7,736,364 B2 | 6/2010 | Stone |
| 7,766,920 B2 | 8/2010 | Ciccone et al. |
| 7,828,090 B2 | 11/2010 | Drivdahl et al. |
| 7,833,244 B2 | 11/2010 | Cerundolo |
| 7,837,731 B2 | 11/2010 | Sklar |
| 7,883,510 B2 | 2/2011 | Kim et al. |
| 7,909,826 B2 | 3/2011 | Serhan et al. |
| 7,918,288 B2 | 4/2011 | Drivdahl et al. |
| 7,922,730 B2 | 4/2011 | Raines, Jr. |
| 7,959,650 B2 | 6/2011 | Kaiser et al. |
| 7,963,952 B2 | 6/2011 | Wright, Jr. et al. |
| 7,963,983 B2 | 6/2011 | Cerundolo |
| 7,967,861 B2 | 6/2011 | Montgomery et al. |
| 7,993,369 B2 | 8/2011 | Dreyfuss |
| 8,012,083 B2 | 9/2011 | Kucklick et al. |
| 8,021,403 B2 | 9/2011 | Wall et al. |
| 8,034,083 B2 | 10/2011 | Abdelgany et al. |
| 8,043,308 B2 | 10/2011 | Bittenson |
| 8,048,158 B2 | 11/2011 | Hays et al. |
| 8,051,929 B2 | 11/2011 | Drivdahl et al. |
| 8,057,524 B2 | 11/2011 | Meridew |
| 8,075,575 B2 | 12/2011 | Gonzalez-Hernandez |
| 8,100,916 B2 | 1/2012 | Kumar et al. |
| 8,123,749 B2 | 2/2012 | Serhan et al. |
| 8,128,658 B2 | 3/2012 | Kaiser et al. |
| 8,187,309 B2 | 5/2012 | Castaneda et al. |
| 8,202,295 B2 | 6/2012 | Kaplan |
| 8,206,446 B1 | 6/2012 | Montgomery |
| 8,216,131 B2 | 7/2012 | Kucklick |
| 8,221,455 B2 | 7/2012 | Shurnas et al. |
| 8,221,498 B2 | 7/2012 | Boucher et al. |
| 8,226,714 B2 * | 7/2012 | Beck, Jr. ............... A61F 2/0811 |
| | | | 606/232 |
| 8,231,654 B2 | 7/2012 | Kaiser et al. |
| 8,241,298 B2 | 8/2012 | Sengun et al. |
| 8,273,086 B2 | 9/2012 | Serhan et al. |
| 8,277,464 B2 | 10/2012 | Bittenson |
| 8,282,651 B2 | 10/2012 | Ciccone et al. |
| 8,292,555 B2 | 10/2012 | Shaffer |
| 8,328,716 B2 | 12/2012 | Schmieding et al. |
| 8,343,195 B2 | 1/2013 | Rathbun et al. |
| 8,348,972 B2 | 1/2013 | Soltz et al. |
| 8,361,152 B2 | 1/2013 | McCormack et al. |
| 8,377,089 B2 | 2/2013 | Lipchitz et al. |
| 8,430,909 B2 | 4/2013 | Dreyfuss |
| 8,435,293 B2 | 5/2013 | Donnelly et al. |
| 8,435,294 B2 | 5/2013 | Montgomery et al. |
| 8,465,545 B2 | 6/2013 | Montgomery et al. |
| 8,506,573 B2 | 8/2013 | Dreyfuss et al. |
| 8,512,376 B2 | 8/2013 | Thornes |
| 8,512,405 B2 | 8/2013 | Baird |
| 8,523,902 B2 | 9/2013 | Heaven et al. |
| 8,523,903 B2 | 9/2013 | Kilburn-Peterson et al. |
| 8,529,610 B2 | 9/2013 | Graf et al. |
| 8,535,377 B2 | 9/2013 | Myers et al. |
| 8,545,535 B2 | 10/2013 | Hirotsuka et al. |
| 8,562,680 B2 | 10/2013 | Hays et al. |
| 8,608,765 B1 | 12/2013 | Jurbala |
| 8,617,197 B2 | 12/2013 | Friedman et al. |
| 8,617,219 B2 | 12/2013 | Oren et al. |
| 8,636,799 B2 | 1/2014 | Sklar et al. |
| 8,647,385 B2 | 2/2014 | Boucher et al. |
| 8,663,279 B2 | 3/2014 | Burkhart et al. |
| 8,663,325 B2 | 3/2014 | Graf et al. |
| 8,672,960 B2 | 3/2014 | Briganti et al. |
| 8,672,967 B2 | 3/2014 | DiMatteo et al. |
| 8,672,968 B2 | 3/2014 | Stone et al. |
| 8,721,650 B2 | 5/2014 | Fanton et al. |
| 8,747,470 B2 | 6/2014 | Beck, Jr. et al. |
| 8,758,227 B2 | 6/2014 | Kucklick et al. |
| 8,771,223 B2 | 7/2014 | Patton et al. |
| 8,771,303 B1 | 7/2014 | Jurbala |
| 8,778,023 B2 | 7/2014 | Sklar |
| 8,784,431 B1 | 7/2014 | Harder et al. |
| 8,790,368 B2 | 7/2014 | Sullivan et al. |
| 8,821,383 B2 | 9/2014 | Mirza et al. |
| 8,821,527 B2 | 9/2014 | Farnan et al. |
| 8,821,557 B2 | 9/2014 | Corradi et al. |
| 8,840,665 B2 | 9/2014 | Young et al. |
| 8,845,725 B2 | 9/2014 | Barwood et al. |
| 8,870,877 B2 | 10/2014 | Koogle, Jr. |
| 8,932,354 B2 | 1/2015 | Barwood et al. |
| 8,939,983 B2 | 1/2015 | Stone et al. |
| 8,956,410 B2 | 2/2015 | Donnelly et al. |
| 9,056,010 B2 | 6/2015 | Shea et al. |
| 9,060,748 B2 | 6/2015 | Housman et al. |
| 9,060,772 B2 | 6/2015 | Gonzalez-Hernandez |
| 9,095,331 B2 | 8/2015 | Hernandez et al. |
| 9,241,783 B2 | 1/2016 | Trenhaile et al. |
| 9,277,911 B2 | 3/2016 | Hernandez |
| 9,289,283 B2 | 3/2016 | Baird |
| 9,301,751 B2 | 4/2016 | Sullivan et al. |
| 9,314,240 B2 | 4/2016 | Paulk et al. |
| 9,693,856 B2 | 7/2017 | Sengun et al. |
| 9,795,412 B2 | 10/2017 | Sinha |
| 9,833,229 B2 | 12/2017 | Hernandez et al. |
| 10,231,823 B2 | 3/2019 | Piccirillo et al. |
| 10,231,824 B2 | 3/2019 | Piccirillo et al. |
| 2001/0021855 A1 | 9/2001 | Levinson |
| 2002/0077631 A1 | 6/2002 | Lubbers et al. |
| 2002/0151977 A1 | 10/2002 | Paes et al. |
| 2002/0164218 A1 | 11/2002 | Aguirre |
| 2002/0188301 A1 | 12/2002 | Dallara et al. |
| 2003/0125749 A1 | 7/2003 | Yuan et al. |
| 2003/0153921 A1 | 8/2003 | Stewart et al. |
| 2003/0153926 A1 | 8/2003 | Schmieding et al. |
| 2003/0225456 A1 | 12/2003 | Ek |
| 2003/0233095 A1 | 12/2003 | Urbanski et al. |
| 2004/0068262 A1 * | 4/2004 | Lemos .................. A61F 2/0811 |
| | | | 424/426 |
| 2004/0073219 A1 | 4/2004 | Skiba et al. |
| 2004/0073222 A1 | 4/2004 | Koseki |
| 2004/0176767 A1 * | 9/2004 | Bickley ............... A61B 17/683 |
| | | | 606/313 |
| 2004/0193217 A1 | 9/2004 | Lubbers et al. |
| 2004/0230194 A1 | 11/2004 | Urbanski et al. |
| 2004/0267361 A1 * | 12/2004 | Donnelly .............. A61F 2/0811 |
| | | | 623/13.14 |
| 2005/0075668 A1 | 4/2005 | Lizardi |
| 2005/0251137 A1 | 11/2005 | Ball |
| 2006/0004378 A1 | 1/2006 | Raines, Jr. |
| 2006/0015110 A1 | 1/2006 | Pepper |
| 2006/0100627 A1 | 5/2006 | Stone et al. |
| 2006/0116685 A1 | 6/2006 | Urbanski et al. |
| 2007/0005068 A1 | 1/2007 | Sklar |

(56) References Cited

U.S. PATENT DOCUMENTS

| | | |
|---|---|---|
| 2007/0156153 A1 | 7/2007 | Jiang et al. |
| 2007/0162124 A1 | 7/2007 | Whittaker |
| 2007/0255172 A1 | 11/2007 | Pflueger |
| 2007/0288031 A1 | 12/2007 | Dreyfuss et al. |
| 2008/0027430 A1* | 1/2008 | Montgomery ........ A61F 2/0811 606/60 |
| 2008/0109038 A1 | 5/2008 | Steiner et al. |
| 2008/0161864 A1 | 7/2008 | Beck et al. |
| 2008/0215060 A1 | 9/2008 | Garcia et al. |
| 2008/0228186 A1 | 9/2008 | Gall et al. |
| 2008/0228224 A1 | 9/2008 | Sauer et al. |
| 2008/0275431 A1 | 11/2008 | Stone et al. |
| 2008/0275469 A1 | 11/2008 | Fanton et al. |
| 2009/0112270 A1* | 4/2009 | Lunn ................. A61B 17/0401 606/301 |
| 2009/0138043 A1 | 5/2009 | Kohm |
| 2009/0171400 A1 | 7/2009 | van der Burg et al. |
| 2009/0192608 A1 | 7/2009 | Paulos |
| 2009/0275994 A1 | 11/2009 | Phan et al. |
| 2009/0281581 A1 | 11/2009 | Berg |
| 2009/0287259 A1 | 11/2009 | Trenhaile et al. |
| 2009/0312763 A1 | 12/2009 | McCormack et al. |
| 2009/0312782 A1 | 12/2009 | Park |
| 2009/0318923 A1 | 12/2009 | Burkhart et al. |
| 2010/0016869 A1 | 1/2010 | Paulk et al. |
| 2010/0069958 A1 | 3/2010 | Sullivan et al. |
| 2010/0106194 A1 | 4/2010 | Bonutti et al. |
| 2010/0121348 A1 | 5/2010 | van der Burg et al. |
| 2010/0130989 A1 | 5/2010 | Bourque et al. |
| 2010/0145395 A1 | 6/2010 | Graf et al. |
| 2010/0174369 A1 | 7/2010 | Wang et al. |
| 2010/0198271 A1 | 8/2010 | Leone |
| 2010/0217393 A1 | 8/2010 | Theofilos |
| 2010/0241124 A1 | 9/2010 | Housman et al. |
| 2010/0249801 A1 | 9/2010 | Sengun et al. |
| 2011/0004247 A1 | 1/2011 | Lechmann et al. |
| 2011/0009885 A1 | 1/2011 | Graf et al. |
| 2011/0015675 A1 | 1/2011 | Howard et al. |
| 2011/0071579 A1 | 3/2011 | Reach, Jr. |
| 2011/0098727 A1 | 4/2011 | Kaiser et al. |
| 2011/0106013 A1 | 5/2011 | Whittaker et al. |
| 2011/0106252 A1 | 5/2011 | Barwood et al. |
| 2011/0106253 A1 | 5/2011 | Barwood et al. |
| 2011/0112550 A1 | 5/2011 | Heaven et al. |
| 2011/0112558 A1 | 5/2011 | Whayne et al. |
| 2011/0251621 A1 | 10/2011 | Sluss et al. |
| 2011/0257691 A1 | 10/2011 | Sutterlin et al. |
| 2011/0270323 A1 | 11/2011 | Olsen et al. |
| 2012/0010668 A1 | 1/2012 | Shimko |
| 2012/0057949 A1 | 3/2012 | Canizares, Jr. et al. |
| 2012/0059379 A1 | 3/2012 | Homan et al. |
| 2012/0109156 A1 | 5/2012 | Overes et al. |
| 2012/0109299 A1 | 5/2012 | Li et al. |
| 2012/0116459 A1 | 5/2012 | Nottmeier |
| 2012/0130374 A1 | 5/2012 | Bouduban et al. |
| 2012/0136357 A1 | 5/2012 | Torrie et al. |
| 2012/0150190 A1 | 6/2012 | Rabiner et al. |
| 2012/0150301 A1 | 6/2012 | Gamache et al. |
| 2012/0211543 A1 | 8/2012 | Euteneuer |
| 2012/0215232 A1 | 8/2012 | Olsen et al. |
| 2012/0245686 A1 | 9/2012 | Park |
| 2012/0316565 A1 | 12/2012 | Stark |
| 2013/0006302 A1 | 1/2013 | Paulk et al. |
| 2013/0103054 A1 | 4/2013 | Housman |
| 2013/0103080 A1 | 4/2013 | Hernandez |
| 2013/0125714 A1 | 5/2013 | Dahners |
| 2013/0158597 A1 | 6/2013 | Hernandez |
| 2013/0158664 A1 | 6/2013 | Palmatier et al. |
| 2013/0190817 A1 | 7/2013 | Bouduban et al. |
| 2013/0197534 A1 | 8/2013 | Lauderbaugh et al. |
| 2013/0197591 A1 | 8/2013 | Corradi et al. |
| 2013/0238036 A1 | 9/2013 | Sinha |
| 2013/0267998 A1 | 10/2013 | Vijay et al. |
| 2013/0268010 A1 | 10/2013 | Santangelo et al. |
| 2013/0310842 A1 | 11/2013 | Winkler et al. |
| 2013/0325128 A1 | 12/2013 | Perloff et al. |
| 2013/0331942 A1 | 12/2013 | Baird |
| 2013/0338710 A1 | 12/2013 | Heaven et al. |
| 2014/0005686 A1 | 1/2014 | Patton et al. |
| 2014/0046369 A1 | 2/2014 | Heaven et al. |
| 2014/0081324 A1 | 3/2014 | Sengun |
| 2014/0107713 A1 | 4/2014 | Pech et al. |
| 2014/0171983 A1 | 6/2014 | Graf et al. |
| 2014/0172095 A1 | 6/2014 | Graf et al. |
| 2014/0188166 A1 | 7/2014 | Cobb et al. |
| 2014/0228898 A1 | 8/2014 | Gordon |
| 2014/0236183 A1 | 8/2014 | Graf et al. |
| 2014/0243978 A1 | 8/2014 | Beck, Jr. et al. |
| 2014/0243982 A1 | 8/2014 | Miller |
| 2014/0249579 A1 | 9/2014 | Heaven et al. |
| 2014/0257384 A1 | 9/2014 | Dreyfuss et al. |
| 2014/0277133 A1 | 9/2014 | Foerster |
| 2014/0277134 A1 | 9/2014 | ElAttrache et al. |
| 2014/0309668 A1 | 10/2014 | Sullivan et al. |
| 2014/0343604 A1 | 11/2014 | Frank |
| 2014/0364862 A1 | 12/2014 | Bennett et al. |
| 2015/0018878 A1 | 1/2015 | Rizk et al. |
| 2015/0018947 A1 | 1/2015 | Barwood |
| 2015/0039030 A1 | 2/2015 | Saliman et al. |
| 2015/0066042 A1 | 3/2015 | Cummins et al. |
| 2015/0173741 A1 | 6/2015 | Housman et al. |
| 2015/0190130 A1 | 7/2015 | Groh |
| 2015/0238327 A1 | 8/2015 | Cheng et al. |
| 2016/0113643 A1 | 4/2016 | Diduch et al. |
| 2016/0113644 A1 | 4/2016 | Diduch et al. |
| 2016/0113756 A1 | 4/2016 | Diduch et al. |
| 2016/0113757 A1 | 4/2016 | Diduch et al. |
| 2016/0113758 A1 | 4/2016 | Diduch et al. |
| 2016/0310260 A1 | 10/2016 | Sengun et al. |
| 2017/0265988 A1 | 9/2017 | Sengun et al. |
| 2017/0290655 A1 | 10/2017 | Piccirillo et al. |
| 2017/0290656 A1 | 10/2017 | Piccirillo et al. |
| 2018/0296319 A1 | 10/2018 | Diduch et al. |
| 2018/0344376 A1 | 12/2018 | Diduch et al. |
| 2019/0029805 A1 | 1/2019 | Piccirillo et al. |
| 2019/0029806 A1 | 1/2019 | Piccirillo et al. |
| 2020/0008928 A1 | 1/2020 | Diduch et al. |
| 2020/0129171 A1 | 4/2020 | Diduch et al. |

FOREIGN PATENT DOCUMENTS

| | | |
|---|---|---|
| CN | 101394795 A | 3/2009 |
| CN | 102098969 A | 6/2011 |
| CN | 102292032 A | 12/2011 |
| CN | 102438548 A | 5/2012 |
| CN | 102470007 A | 5/2012 |
| CN | 202515702 U | 11/2012 |
| CN | 102905629 A | 1/2013 |
| CN | 103209647 A | 7/2013 |
| CN | 103445850 A | 12/2013 |
| CN | 203789970 U | 8/2014 |
| CN | 102098968 B | 7/2015 |
| DE | 10325139 A1 | 12/2004 |
| EP | 1110510 A1 | 6/2001 |
| EP | 1491162 A2 | 12/2004 |
| EP | 2327374 A1 | 6/2011 |
| EP | 2918238 A1 | 9/2015 |
| EP | 3020371 A2 | 5/2016 |
| JP | 2005-013740 A | 1/2005 |
| JP | 2005-066135 A | 3/2005 |
| JP | 2005-506864 A | 3/2005 |
| JP | 2005-323700 A | 11/2005 |
| JP | 2007-050269 A | 3/2007 |
| JP | 2007-306979 A | 11/2007 |
| JP | 2008-086769 A | 4/2008 |
| JP | 2011-0516795 A | 5/2011 |
| JP | 2011-528270 A | 11/2011 |
| JP | 2014-171673 A | 9/2014 |
| WO | 9428799 A1 | 12/1994 |
| WO | 97/31517 A2 | 8/1997 |
| WO | 01/30253 A1 | 5/2001 |
| WO | 2007/110863 A2 | 10/2007 |
| WO | 2009/055800 A1 | 4/2009 |
| WO | 2012/125905 A1 | 9/2012 |

(56) References Cited

FOREIGN PATENT DOCUMENTS

| WO | 2012/129206 | A2 | 9/2012 |
|----|-------------|----|--------|
| WO | 2012/129617 | A1 | 10/2012 |
| WO | 2012138777 | A1 | 10/2012 |
| WO | 2014150053 | A1 | 9/2014 |

OTHER PUBLICATIONS

U.S. Appl. No. 15/093,938, filed Apr. 8, 2016, Tenodesis Implants and Tools.
U.S. Appl. No. 15/093,948, filed Apr. 8, 2016, Tenodesis Anchoring Systems and Tools.
European Search Report for EP Application No. 15191001.5, dated Apr. 1, 2016. (7 pages).
European Search Report for EP Application No. 15191002.3, dated Apr. 15, 2016. (8 pages).
European Search Report for EP Application No. 15191010.6, dated Apr. 4, 2016. (6 pages).
European Search Report for EP Application No. 15191011.4, dated Apr. 1, 2016. (6 pages).
European Search Report for EP Application No. 15191013.0, dated Apr. 14, 2016. (7 pages).
European Search Report for EP Application No. 16166686.2, dated Sep. 20, 2016. (8 pages).
European Search Report for EP Application No. 17165700.0, dated Aug. 11, 2017. (12 pages).
U.S. Appl. No. 15/611,365, filed Jun. 1, 2017, Biceps Repair Device.
European Search Report for EP Application No. 17165749.7, dated Aug. 21, 2017.
U.S. Appl. No. 14/610,609, filed Jan. 30, 2015, Biceps Tenodesis Implants and Delivery Tools.
U.S. Appl. No. 14/610,618, filed Jan. 30, 2015, Biceps Tenodesis Implants and Delivery Tools.
U.S. Appl. No. 14/610,626, filed Jan. 30, 2015, Biceps Tenodesis Anchor Implants.
U.S. Appl. No. 14/610,730, filed Jan. 30, 2015, Biceps Tenodesis Delivery Tools.
U.S. Appl. No. 16/010,790, filed Jun. 18, 2018, Biceps Tenodesis Implants and Delivery Tools.
U.S. Appl. No. 16/047,650, filed Jul. 27, 2018, Biceps Tenodesis Delivery Tools.
U.S. Appl. No. 16/574,655, filed Sep. 18, 2019, Biceps Tenodesis Anchor Implants.
U.S. Appl. No. 16/732,709, filed Jan. 2, 2020, Biceps Tenodesis Implants and Delivery Tools.

* cited by examiner

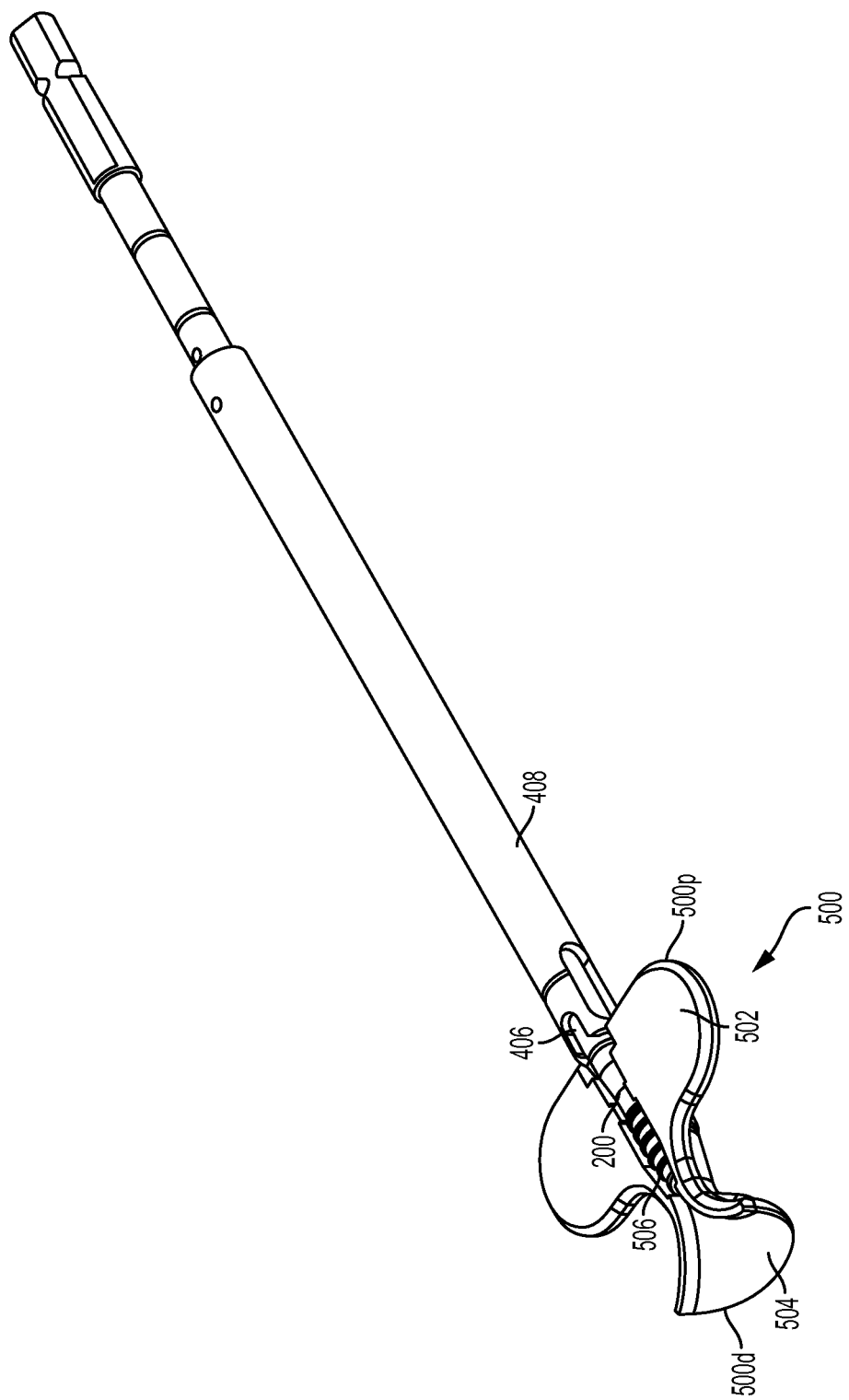

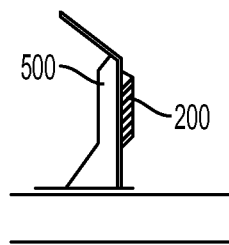
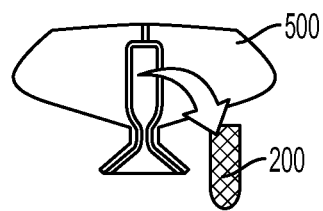
FIG. 26A    FIG. 26B
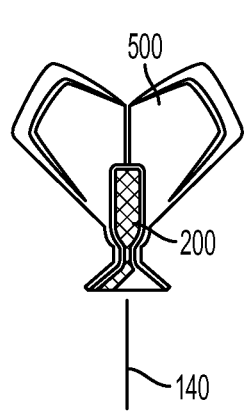
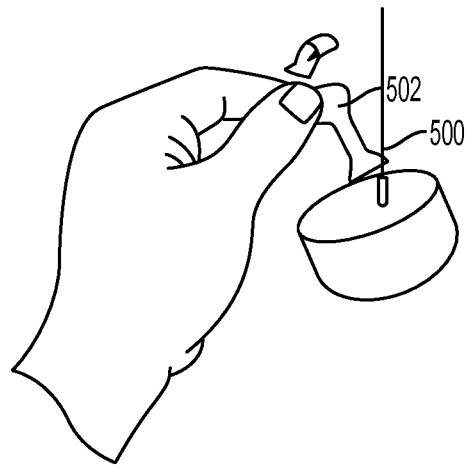
FIG. 26C    FIG. 26D

BICEPS TENODESIS IMPLANTS AND DELIVERY TOOLS

CROSS-REFERENCE TO RELATED APPLICATIONS

The present application claims priority to U.S. Provisional Appl. No. 62/067,701 filed on Oct. 23, 2014 and entitled "Biceps Tenodesis Implants and Delivery Devices," which is hereby incorporated by reference in its entirety.

FIELD

Surgical devices and methods are provided for anchoring tissue to bone, and more particularly surgical implants, delivery tools, and methods are provided for securing a biceps tendon to the humerus.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

While current procedures can provide an effective means for anchoring a tendon to bone, they can suffer from several drawbacks. For example, current procedures require the use of numerous tools, which can lead to a prolonged procedure and increased costs. The use of a screw can also increase the risk of damage to the tendon, as rotation of the screw into the bone hole can tear or sever through the tendon. Moreover, it can be difficult to maintain the desired tension on the tendon while the screw is being implanted, as the tendon can become misaligned and or can slip during insertion of the screw. Any tension applied to the tendon during insertion of the anchor can also cause the anchor to back-out of the bone hole.

Accordingly, there remains a need for improved methods and devices for anchoring tissue to bone, and in particular for performing a biceps tenodesis.

SUMMARY

Various implants, tools and methods are provided for attaching a tendon to bone. In one embodiment, an anchor assembly for anchoring a tendon to bone is provided and includes a sheath having a substantially solid distal end with at least two sidewalls extending proximally therefrom and separated by at least first and second slots. The sidewalls can have threads formed on an internal surface thereof and the sidewalls can define an inner lumen therebetween. The solid distal end of the sheath can have a mating feature. The anchor assembly can further include a guidewire having a distal tip configured to releasably mate with the mating feature in the sheath. In one embodiment, the mating feature can be a threaded bore formed in the sheath and the distal tip on the guidewire can be threaded for threadably mating with the threaded bore. The guidewire can extend proximally from the sheath when mated thereto. The anchor assembly can further include an expander that can have a generally elongate cylindrical configuration such that the expander is configured to be received within the inner lumen of the sheath. In one embodiment, the expander can have threads formed on an external surface thereof that can threadably mate with the threads formed on the internal surface of the at least two sidewalls. The expander can further include a lumen extending therethrough to receive the guidewire.

In some embodiments, the sheath of anchor assembly can include at least one anti-collapse tab formed on at least one of the sidewalls adjacent to one of the slots. The at least one tab can be configured to limit movement of the sidewalls toward one another. In some embodiments, the sidewalls can have an increased thickness at a mid-portion thereof as compared to proximal and distal portions thereof. In other embodiments, the sidewalls can include ribs extending radially therearound. For example, the ribs on a first sidewall of the anchor can be angled distally and the ribs on a second opposite sidewall of the anchor can be angled proximally.

The sheath can also include at least one anti-plunge tab extending radially outward from a proximal-most end thereof. The anti-plunge tab can be configured to limit an insertion depth of the sheath into a bone hole. The sheath can also at least one retaining tab extending radially outward from the sheath at a predetermined distance from the anti-plunge tab. The distance can be configured such that the anti-plunge tab can be positioned on a proximal surface of cortical bone and the retaining tab can be positioned on a distal surface of the cortical bone. In one exemplary embodiment, the distance can be greater than about 0.5 mm.

In some embodiments, the anchor assembly can include a sheath that can have a concave distal-facing end for seating a tendon. In some embodiments, the anchor assembly can include a sheath that can have a convex proximal facing end.

In other aspects, the first and second slots can each have a proximal portion, a distal portion, and a transition region extending between the proximal and distal portions. The proximal and distal portions can each have a constant width, and the transition region can have a width that tapers inward in a distal direction. In an exemplary embodiment, a length of transition region can be substantially equally to a width of the proximal portion.

In another embodiment, a method for anchoring a tendon to bone is provided. The method can include positioning a distal end of a sheath over a tendon extending across a bone hole. The sheath can have a guidewire mated thereto and extending proximally therefrom. The sheath with the guidewire mated thereto can be advanced into the bone hole to cause the tendon to advance into the bone hole and extend between the sheath and the bone hole. A cannulated expander can be advanced along the guidewire and into the sheath to cause the sheath to expand outward to anchor the tendon within the bone hole.

The method can include advancing the sheath into the bone hole using an inserter tool having the guide extending therethrough. The method can further include, after advancing the sheath, manipulating the inserter tool to release the guidewire from a guidewire grasper in the inserter tool, and removing the inserter tool from the guidewire. In another embodiment, when the expander is fully inserted into the sheath, the expander and the sheath can be in full circumferential contact along a majority of a length thereof. In another embodiment, the expander can be non-rotatably advanced into the sheath, or alternatively a distal portion of the expander can be non-rotatably advanced into the sheath, and a proximal portion of the expander can be rotatably threaded into the sheath.

In other aspects, the method can include advancing the expander along the guidewire using a driver tool. The driver tool can include an outer shaft having opposed prongs on a distal end thereof that are positioned within opposed slots formed in the sheath. The driver tool can further include an inner shaft extending through the outer shaft and engaged with the expander. The inner shaft can be rotated to advance the expander into the sheath while the prongs on the outer shaft hold the sheath substantially stationary. The driver tool can be removed from the guidewire and the sheath leaving the sheath and the expander implanted in bone.

In another embodiment, an anchor assembly for anchoring a tendon to bone is provided and includes a sheath and a threaded expander. The sheath can have a body with at least two sidewalls extending proximally therefrom. The sidewalls can be separated by at least first and second slots, and the sidewalls can define an inner lumen therebetween. The sidewalls can further include threads formed on an internal surface thereof. The threaded expander can be configured to be received between the at least two sidewalls and to threadably mate with the threads formed on the internal surface of the sidewalls. The sheath and the threaded expander can be configured such that, when the expander is fully threaded into the sheath, a mid-portion of the sidewall expands outward by a distance that is greater than a distance that proximal and distal portions of the sidewalls expand outward. The mid-portion thus defines a maximum outer dimension of the sheath to anchor the sheath within a bone hole.

In some embodiments, the mid-portion of the at least two sidewalls can have a thickness that is greater than a thickness of the proximal and distal portions of the at least two sidewalls. In some embodiments, the expander of the anchor assembly can have a minor diameter and the threads on the expander define a major diameter. A minor diameter of the expander can cause the sidewalls of the sheath to expand outward. In other embodiments, a major diameter or both a minor and major diameter can cause the sidewalls of the sheath to expand outward. In some embodiments, the expander of the anchor assembly can include a cylindrical proximal portion having a substantially constant diameter, and a tapering distal portion having a diameter that decreases distally.

In other aspects, a method for anchoring a tendon to bone is provided. The method can include positioning a distal end of a sheath over a tendon extending across a bone hole. The sheath can be advanced into the bone hole to cause the tendon to be advanced into the bone hole. An expander can be inserted into an inner lumen of the sheath such that the expander causes proximal, middle, and distal portions of the sheath to expand outward. The mid-portion of the sheath can expand outward by a distance that is greater than a distance that the proximal and distal portions of the sheath expand outward. The mid-portion can thus define a maximum outer dimension of the sheath that prevents the sheath from backing out of the bone hole.

In other aspects, the sheath can have threads formed on an inner surface thereof. The expander can further include threads formed on an outer surface thereon. The expander can be inserted into the sheath by rotating the expander relative to the sheath to thread the expander into the sheath. The expander can have a minor diameter and the threads on the expander can define a major diameter. The minor diameter of the expander can cause the sheath to expand outward. In other embodiments, the major diameter or both the minor and major diameters of the expander can cause the sheath to expand outward.

In another embodiment, an anchor assembly for anchoring a tendon to bone is provided. The anchor assembly can include a sheath having a substantially solid distal end, and at least two sidewalls extending proximally from the distal end. The sidewalls can be separated by at least first and second slots and the sidewalls can define an inner lumen therebetween. The sheath can further include at least one anti-plunge tab extending from a proximal-most end of the sheath adjacent to the slots. The anti-plunge tab can be configured to prevent over-insertion of the sheath into a bone hole. The sheath can further include at least one retaining tab extending from the sheath at a location distal to the anti-plunge tab. The retaining tab can be positioned a distance apart from the anti-plunge tab. The distance can be configured such that when the anti-plunge tab is on a proximal surface of a cortical bone, the retaining tab will extend beneath a distal surface of the cortical bone. The anchor assembly can further include a threaded expander that can be received between the at least two sidewalls on the sheath to cause the sheath to expand and engage the cortical bone.

In some embodiments, the at least one anti-plunge tab can include a pair of anti-plunge tabs, and the at least one retaining tab can include a pair of retaining tabs. In some embodiments, the at least one anti-plunge tab can extend radially outward by a distance that is greater than a distance that the at least one retaining tab extends radially outward. In some embodiment, the at least one anti-plunge tab can be co-planar with the at least one retaining tab. In some embodiments the distance between the anti-plunge tab and the retaining tab can be greater than about 0.5 mm, and more preferably it can be in the range of about 1.0 mm to 2.0 mm.

In other aspects, a method for anchoring a tendon to bone is provided. The method can include positioning a distal end of a sheath over a tendon extending across a bone hole in a bone. The sheath can be advanced into the bone hole such that the tendon is advanced into the bone hole. At least one anti-plunge tab extending from opposed sides of a proximal-most end of the sheath can abut against a surface of the bone to limit an insertion depth of the sheath into the bone hole. At least one retaining tab extending from sheath at a location distal to the anti-plunge tab can extend beneath a surface of the bone. An expander can be inserted into the sheath to cause the sheath to expand outward. The retaining tab can expand to a diameter that is greater than a diameter of the bone hole to thereby prevent removal of the sheath from the bone hole, thereby anchoring the tendon within the bone hole.

In one embodiment, the anti-plunge tab can extend radially outward by a distance that is greater than a distance that the retaining tab extends radially outward. The retaining tab can be inserted into the bone hole while the anti-plunge tab can be prevented from being inserted into the bone hole. The bone can be, for example, cortical bone. The bone can have a thickness of at least about 0.5 mm, and the anti-plunge tab can be positioned at least about 0.5 mm apart from the retaining tab to receive the bone therebetween.

In another embodiment, an anchor inserter tool is provided having a first elongate body with first and second prongs extending distally from a distal end thereof and configured to extend along opposed slots formed in a sheath of an anchor assembly. The anchor assembly can also include a second elongate body slidably disposed relative to the first elongate body. The anchor assembly can also include a handle assembly coupled to a proximal end of each of the first and second elongate bodies. The handle assembly can be configured such that the first elongate body has first and second ranges of motion. The first elongate body in the first range of motion can be movable between a first position in which the first and second prongs extend distally beyond the second elongate body and a second position in which the first and second prongs are retained within the second elongate body. The first elongate body in the second range of motion can be movable from the second position to a third position in which the first elongate body is configured to cause a guidewire extending through the first elongate body and mated to the handle assembly to be disengaged and released from the handle assembly.

In certain embodiments, the first elongate body can be an inner shaft and the second elongate body can be an outer shaft disposed around the inner shaft. In some embodiments, the second elongate body can include a closed distal end having a central bore formed therein for receiving a guidewire. The second elongated body can further include first and second slots formed therein and extending radially outward from the central bore for receiving the prongs. In another embodiment, a distal portion of the second elongate body can include first and second concavities formed in opposite outer sidewalls thereof. In another embodiment, the first and second elongate bodies can be configured to be releasably locked relative to one another such that movement of the first and second elongate bodies relative to one another is prevented.

In certain embodiments, the handle assembly can include a first biasing element that applies a first biasing force that must be overcome to move the first elongate body from the first position to the second position, and the handle assembly includes a second biasing element that applies a second biasing force that must be overcome to move the first elongate body from the second position to the third position. The second biasing force can be greater than the first biasing force. The handle assembly can also include a guidewire grasping element that can be configured to engage a proximal end of a guidewire coupled to a sheath of an anchor assembly and extending through the first elongate body. In other embodiments, the handle assembly can include an actuator coupled to the first elongate body and configured to move the first elongate body through the first and second ranges of motion. In other embodiments, the handle assembly can include a first handle mated to the second elongate body and having an engagement element formed therein for engaging a guidewire. The handle assembly can further include a second handle mated to the first elongate body for moving the first elongate body relative to the second elongate body.

In another embodiment, a tendon anchoring system is provided. The system can include an anchor assembly having a sheath with at least two sidewalls at least partially separated by at least first and second slots. The sidewalls can define an inner lumen therebetween. The anchor assembly can further include an expander that can be received within the inner lumen of the sheath. The system can also include an inserter tool that can have an outer shaft with an inner lumen extending therethrough, and an inner shaft having first and second prongs formed on a distal end thereof. The prongs can be sized and dimensioned to extend along the first and second slots in the sheath and to extend distally beyond a distal end of the sheath. The inserter tool can also include a handle assembly coupled to a proximal end of the inner and outer shafts. The handle assembly can have an actuator configured to axially move the inner shaft relative to the outer shaft to thereby move the prongs between an extended position in which the prongs extend distally beyond a distal end of the outer shaft, and a retracted position in which the prongs are retracted into the distal end of the outer shaft.

In certain embodiments the outer shaft can have a closed distal end having a central bore formed therein for receiving a guidewire. The outer shaft can also have first and second slots formed therein and extending radially outward from the central bore for receiving the first and second prongs. In some embodiments, a guidewire can be mated to the sheath, and a guidewire grasping element in the handle assembly can be configured to engage a proximal end of the guidewire. In other embodiments, the first and second prongs can include a connector extending therebetween along a proximal portion of the prongs, and the connector can have a central lumen extending therethrough. In yet another embodiment, the sheath can include at least one anti-plunge tab extending radially outward from a proximal-most end thereof, and a distal facing surface of the outer shaft can include at least one recess formed therein for seating the at least one anti-plunge tab.

In other aspects, the actuator can move between a distal position on the handle assembly in which the prongs extend distally beyond the distal end of the outer shaft, and a proximal position on the handle assembly in which the prongs are retracted into the distal end of the outer shaft. In certain embodiments, the actuator can be biased to the distal position.

A method for anchoring a tendon to bone is also provided. The method can include attaching a sheath to an inserter tool such that a pair of prongs on a distal end of an inner shaft of the inserter tool extend along opposed slots formed in the sheath. The method can include manipulating an actuator on a handle assembly of the inserter tool to retract the pair of prongs into an outer shaft of the inserter tool, and with the prongs retracted, manipulating the handle assembly to advance the sheath through tissue. After the sheath is advanced through tissue, the actuator can be manipulated to cause the prongs to extend along the opposed slots formed in the sheath and to extend distally beyond a distal end of the sheath. The method can further include positioning the tendon between the pair of prongs, and manipulating the handle assembly to advance the prongs, with the tendon therebetween, and the sheath into a bone hole. The inserter tool can be removed such that the anchor and the tendon remain in the bone hole. In some embodiments, the method can further include inserting an expander into the sheath to cause the sheath to expand outward to anchor the tendon within the bone hole.

In certain embodiments, the method can include measuring a size of a tendon to be anchored to bone by positioning the tendon between the pair of prongs on the distal end of the inner shaft of the inserter tool. In some embodiments, measuring a size of a tendon can include measuring a tendon using a first inserter tool having a pair of prongs spaced a first distance apart, and measuring the tendon using a second inserter tool having a pair of prongs spaced a second distance apart.

In other aspects, attaching the sheath to the inserter can include advancing a guidewire mated to the sheath proximally into a distal end of the inner shaft of the inserter tool to cause the guidewire to mate with a guidewire grasper in the handle assembly of the inserter tool. In some embodiments, removing the inserter can further include manipulating the actuator to cause the guidewire grasper to release the guidewire.

In another aspect, an anchor driver tool is provided. The anchor driver tool can include an outer shaft having first and second prongs extending distally from a distal end thereof. The first and second prongs can be configured to extend into opposed slots formed in a sheath of an anchor assembly. The anchor driver tool can also include an inner shaft extending through the outer shaft and having a distal end configured to mate with an expander of an anchor assembly. A handle assembly can be coupled to a proximal end of the inner and outer shafts. The handle assembly can include an actuator configured to rotate the inner shaft relative to the outer shaft to drive an expander coupled to a distal end of the inner shaft into a sheath coupled to the first and second prongs of the outer shaft. The outer shaft can be configured to hold the sheath in a substantially fixed position during rotation of the inner shaft. In some embodiments, the actuator can include a knob on a proximal end of the inner shaft, and the handle assembly can include a stationary handle on a proximal end of the outer shaft.

In certain embodiments, the outer shaft can include opposed viewing windows formed in a distal portion thereof, and/or opposed cut-outs formed in the distal end thereof for seating a tendon. In some embodiments, the outer shaft is freely rotatably movable relative to the inner shaft, and axial translation of the outer shaft relative to the inner shaft can be limited to a predetermined distance. In some embodiments, at least one of the inner and the outer shafts can include at least one marking for indicating when an expander is fully seated within a sheath.

In another aspect, a tendon anchoring system is provided and includes an anchor assembly and an inserter assembly. The anchor assembly can include a sheath having a generally elongate cylindrical configuration with at least two sidewalls at least partially separated by at least first and second slots. The sidewalls can define an inner lumen therebetween. The anchor assembly can also include an expander configured to be received within the inner lumen of the sheath. The inserter assembly can include an outer shaft having first and second prongs formed on a distal end thereof. The prongs can be sized and dimensioned to be received within the first and second slots in the sheath. The inserter assembly can further include an inner shaft extending through the outer shaft and having a distal end configured to mate with the expander. A handle assembly can be coupled to a proximal end of the inner and outer shafts. The handle assembly can have an actuator configured to rotate the inner shaft to drive the expander into the sheath while the outer shaft prongs hold the sheath in a substantially fixed position In certain embodiments, the tendon anchoring system can include a loader having a pathway extending therethrough between proximal and distal ends thereof for seating the expander and a distal portion of the outer shaft. The loader can include a funneled distal end.

In some embodiments, the prongs can have a length that is less than a length of the first and second slots such that the prongs extend only partially therein. In some embodiments, the actuator can include a knob on a proximal end of the inner shaft, and the handle assembly can include a stationary handle on a proximal end of the outer shaft. In some embodiments markings can be formed on at least one of the inner and outer shafts for indicating when the expander is fully seated within the sheath.

In some embodiments, the outer shaft can include opposed viewing windows formed in a distal portion thereof, and/or opposed cut-outs formed in the distal end thereof for seating a tendon. In some embodiments, the outer shaft is freely rotatably movable relative to the inner shaft, and axial translation of the outer shaft relative to the inner shaft is limited to a predetermined distance.

In another aspect, a method for anchoring a tendon to bone is provided. The method can include advancing a sheath and a tendon into a bone hole in bone such that the tendon extends between the sheath and the bone hole. A pair of prongs on a distal end of an outer shaft of a driver tool can be inserted into opposed slots formed in the sheath implanted in the bone hole. The method can also include manipulating an actuator on a handle assembly of the driver tool to rotate an inner shaft extending through the outer shaft to thereby advance an expander coupled to a distal end of the inner shaft into the sheath. The pair of prongs on the outer shaft can hold the sheath substantially stationary while the inner shaft rotates the expander into the sheath. In some embodiments, the prongs can prevent the sidewalls of the sheath from collapsing radially inward.

In some embodiments, the inner shaft is freely rotatable relative to the outer shaft, and axial movement of the inner shaft to advance the expander into the sheath can be limited to a predetermined distance. In other embodiments, the inner shaft can be cannulated to receive a guidewire coupled to the sheath such that the guidewire axially aligns the inner shaft and the outer shaft relative to the sheath.

In some embodiments, tabs on the sheath limit an insertion depth of the sheath into the bone hole. In some embodiments, the outer shaft can include opposed cut-outs formed in a distal end thereof. The tendon can extend into the opposed cut-outs when the prongs are inserted into the slots such that the outer shaft is positioned against a surface of the bone.

BRIEF DESCRIPTION OF THE DRAWINGS

The invention will be more fully understood from the following detailed description taken in conjunction with the accompanying drawings, in which:

FIG. 25 is a perspective view of one embodiment of a loader, shown having the expander screw and driver tool of FIG. 1 coupled thereto;

FIG. 26A is a side view of the loader of FIG. 25;

FIG. 26B is a front view of the loader of FIG. 26A, showing the expander screw of FIG. 1 about to be received therein;

FIG. 26C is a front view of the loader and expander screw of FIG. 26B shown in the mated configuration, and being guided onto a guidewire;

FIG. 26D illustrates the loader, expander screw, and guidewire of FIG. 26C, showing the loader removed leaving the expander screw positioned on the guidewire;

DETAILED DESCRIPTION

Figure 1:
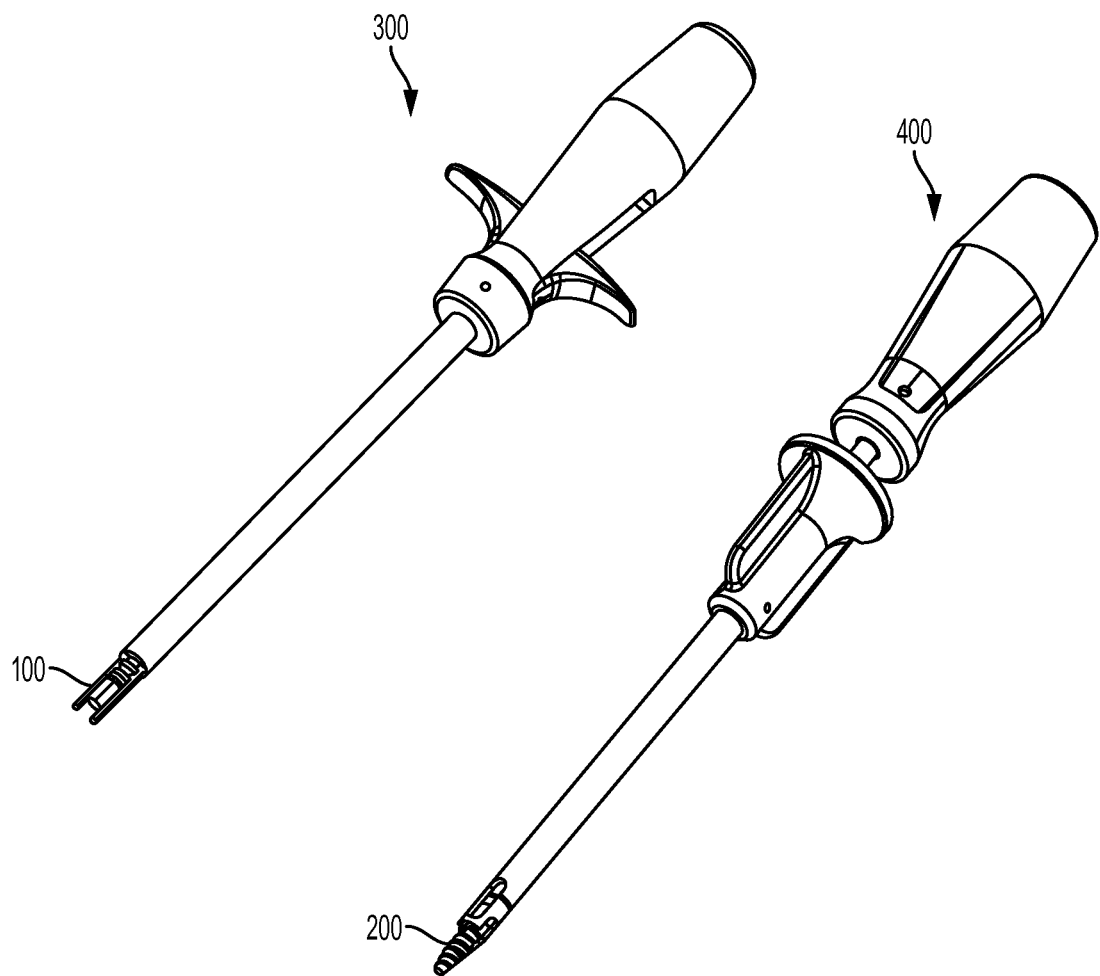
FIG. 1 is a perspective view of a biceps tenodesis system having a sheath inserter, a sheath, a driver tool, and an expander screw.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for anchoring a ligament or tendon to bone. In an exemplary embodiment, the methods and devices are used to perform a biceps tenodesis, however a person skilled in the art will appreciate that the devices and methods can be used in various procedures and for anchoring any tissue to bone. In one embodiment, a surgical implant is provided having a sheath and an expander that is received within the sheath. Various delivery tools, including a sheath inserter and a driver, are also provided. In use, the sheath inserter can be used to position a tendon within a prepared bone hole, and it can be used to deliver the sheath with a guidewire coupled thereto into the bone hole. The driver can be provided for delivering the expander into the sheath. A loader can optionally be used to load the driver and expander onto the guidewire coupled to the implanted sheath.

A person skilled in the art will appreciate that the surgical implants, delivery tools, and methods disclosed herein can be used with a variety of surgical devices, including measuring devices, drills, and mallets, etc.

The embodiments described herein generally relate to systems and methods for preforming biceps tenodesis surgeries. In some embodiments, the system can include any one or more of the following components: an anchor assembly or an implant having a sheath and expander; a sheath inserter tool; a driver tool; and a loader. The components of the system can reduce the number of steps required to perform a biceps tenodesis, and can do so with minimal risk of injuring to the tendon.

FIG. 1 illustrates one embodiment of a biceps tenodesis system that includes a sheath inserter tool 300, a sheath 100 coupled to a distal end of the sheath inserter tool 300, a driver tool 400, and an expander in the form of a screw 200 coupled to a distal end of the driver tool 400. While not shown in FIG. 1, the system can also include a loader configured to removably mate to the driver tool 400 and the screw 200, as well as various other devices, such as bone preparation tools and measurement devices.

The apparatus and methods described herein may have a number of advantages over existing techniques for preforming bicep tenodesis. In particular, the entire attachment preparation procedure can be straightforward and requires a surgeon to take only a few quick steps to affix the implant structure including the sheath and the expander to the bone. A risk of damaging the tendon during rotation of the expander or any other technique requiring rotation of a component in direct contact with the tendon may be avoided. As a result, a risk of causing trauma to the tendon can be reduced and the time required to prepare and affix the tendon can be significantly reduced, which can facilitate the surgery and mitigate inconvenience to the patient. In addition, the described techniques can help save operating room costs.

Implant

Figure 2:
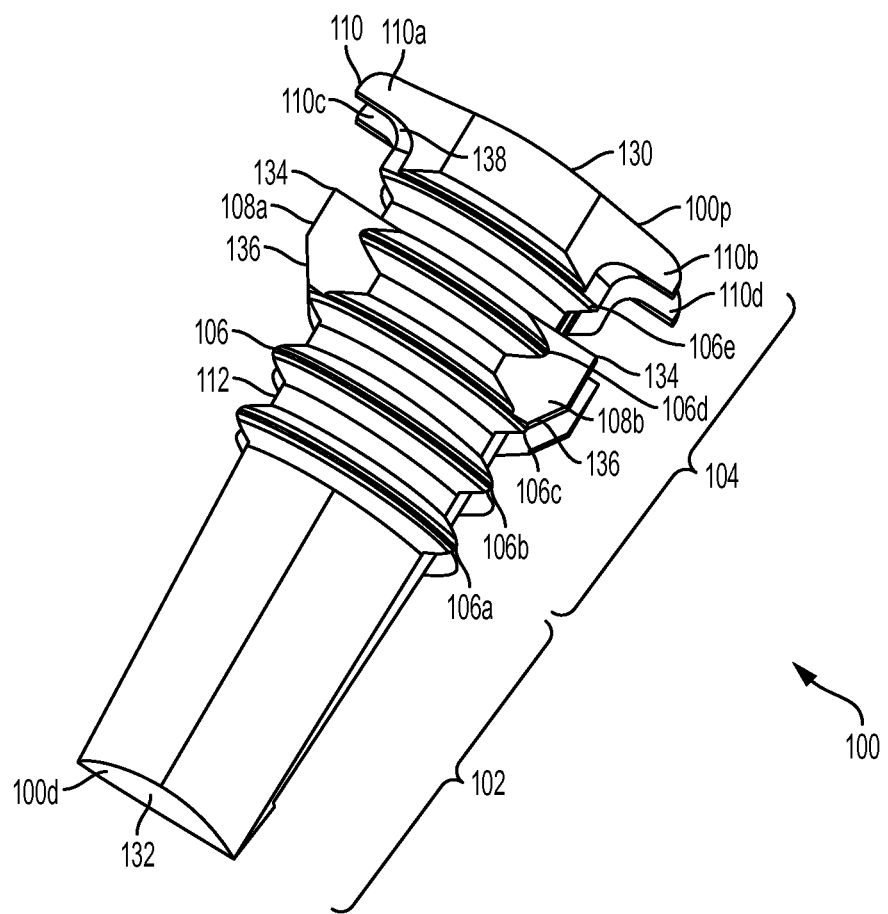
FIG. 2 is a side perspective view of the sheath of FIG. 1.

FIG. 2 illustrates the implantable sheath of FIG. 1 in more detail. In general, the sheath is configured to seat a tendon therearound, and to receive an expander therein which is effective to cause the sheath expand into bone to anchor the tendon within a bone hole. The sheath can be formed from any bio-compatible material, and it can optionally be bio-absorbable.

Figure 3:
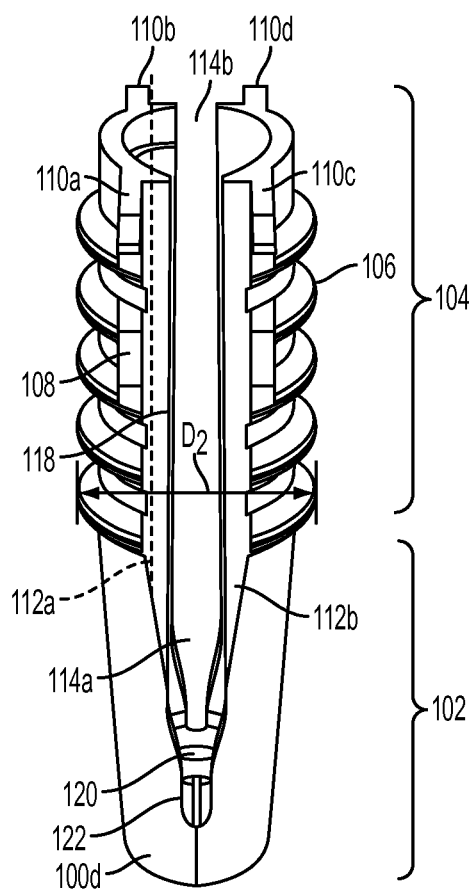
FIG. 3 is another side perspective view of the sheath of FIG. 1.

While the shape and configuration of the sheath can vary, in an exemplary embodiment the sheath 100 has a generally elongate cylindrical shape, with a circular or ovular cross-sectional geometry. The sheath 100 has a proximal end 100p and a distal end 100d as shown in FIG. 2. As shown in the side view of the sheath 100 in FIG. 3, the sheath 100 can be a split sheath, with a first sidewall 112a and a second sidewall 112b that are connected at the distal end 100d and that are separated by first and second elongates slots 114a, 114b extending therebetween. The elongate slots 114a, 114b can extend from the proximal end 100p and can terminate just proximal to the distal end 100d. The slots 114a, 114b are preferably shaped to seat a fork-member on the sheath inserter tool, as will be discussed in more detail below. In the illustrated embodiment, the slots 114a, 114b decrease in width in a proximal-to-distal direction. As further shown in FIG. 2, the distal end 100d of the sheath 100 can be solid and closed, however an inner surface 116 can include a bore 120 formed therein that is configured to receive a guidewire 140 therein. The bore 120 is preferably a blind bore that is threaded for mating with a threaded tip of the guidewire 140, however the bore can optionally extending all the way through the distal end.

As shown above in FIG. 3, the elongate slots 114a, 114b formed in the sidewalls 112a, 112b of the sheath 100 can allow for sheath expansion. The slots 114a, 114b between sidewalls 112a, 112b of the sheath 100 preferably have a width that is greater than a width of the forks (discussed below) so that the sidewalls 112a, 112b can collapse inward toward the fork to allow the tendon and the sheath 100 to be pushed into the bone hole. For example, the slots 114a, 114b in the resting state can have a width that is greater than a width of the fork to allow the sidewalls 112a, 112b of the sheath 100 to move radially inward toward the fork by a first distance to a collapsed position. The sidewalls can also be configured to flex and move radially outward away from the resting position by a second distance to an expanded position. In an exemplary embodiment, the sheath 100 is configured to have a resting state in which the first and second distances are equal. Such a configuration can be advantageous as the sidewalls 112a, 112b move from a middle resting position, rather than having the resting position be in the expanded position and having the sheath flex through both the first and second distances. In use, prior to implantation the sidewalls 112a, 112b can have a curvature that can be semi-circular. When the sheath 100 is inserted into the bone hole, the sidewalls 112a, 112b can collapse into an oval orientation. When the sheath is expanded by the expander, the sidewalls can expand to a circular orientation, which can help attain uniform compression all the way around the sheath 100.

Figure 6:
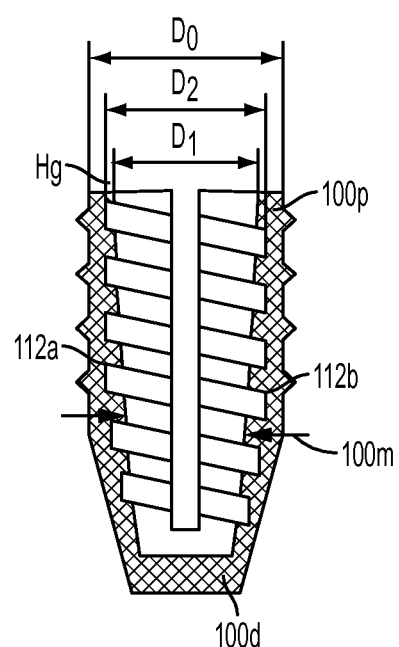
FIG. 6 is a cross-sectional view of the sheath of FIG. 1.

In some embodiments, the sheath can be formed having a varied wall thickness. As shown in FIG. 6, an outer diameter Do of the sheath can be substantially constant along the proximal portion and can taper distally inward along the distal portion to facilitate insertion. The inner lumen of the sheath 100 can have both an inner minor diameter D1 and an inner major diameter D2. The inner major diameter D2 (and optionally the inner minor diameter D1) of the sheath 100 can taper distally inward from the proximal end 100p toward the distal end 100d, such that a thickness of the sidewalls 112a, 112b at a mid-portion 100m of the sheath 100 is greater than a thickness at the proximal end 100p and the distal end 100d of the sheath. As a result, when the screw 200 is inserted into the sheath 100, a mid-portion 100m of the sheath 100, i.e., a portion of the sheath which is placed under the cortex, can expand to a diameter that is greater than a diameter of the sheath 100 at the proximal end 100p, i.e., a portion of the sheath positioned within the cortex. The expansion of the mid-portion 100m thereby "anchors" the sheath 100 to prohibit retraction of the sheath 100 back through the bone hole opening.

As shown in FIG. 2, the sheath 100 can also include a distal facing surface that is concave or saddled to seat the tendon thereon. This surface can be used to assist in the retention of the tendon during the insertion or dunking of the tendon and sheath 100 into the bone hole. This feature can be used in conjunction with or independent of other tendon retention features.

As further shown, the sheath can include a convex proximal surface on each side wall 112a, 112b. The convex shape provides a rounded edge that can help avoid damage to any tissue in contact with the sheath.

The sheath 100 can also include various surface features formed thereon to facilitate engagement with the bone. In one embodiment, the sheath 100 can have surface features, such as ribs 106a, 106b, 106c, 106d, 106e, and each rib can be uni-planar so as to allow the sheath to be inserted into bone without the need to rotate the sheath. A distal portion 102 of the sheath can be free of surface features. While ribs are shown, a person skilled in the art will appreciate that the sheath can include various bone-engaging surface features, such as threads, teeth, or other protrusions.

Figure 7:
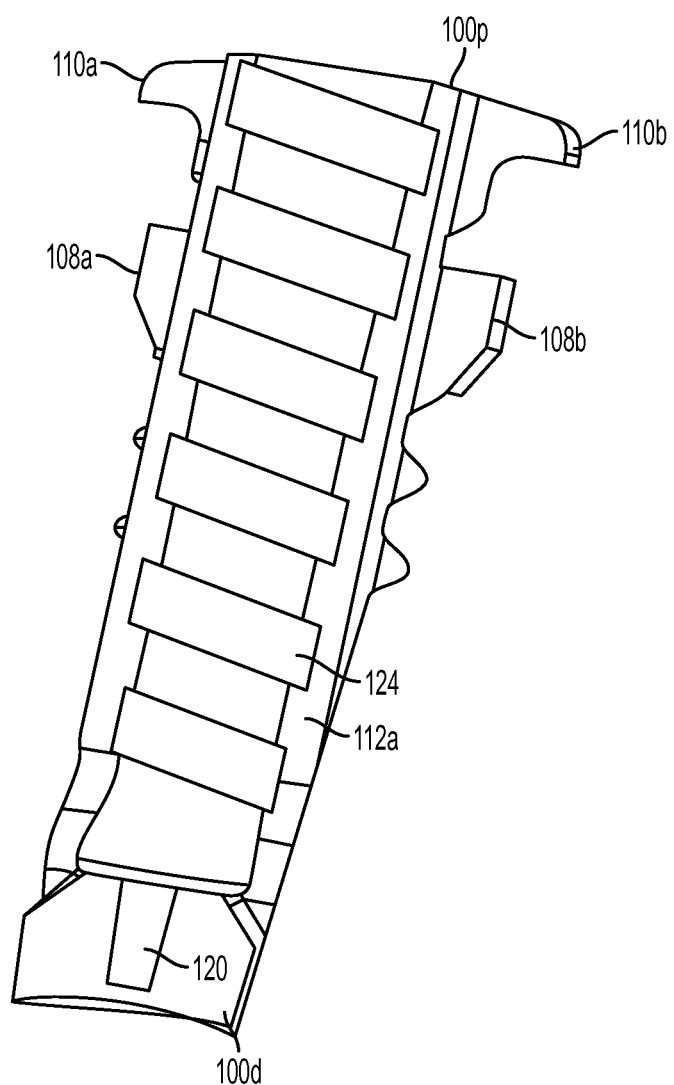
FIG. 7 is another cross-sectional view of the sheath of FIG. 1.
Figure 11A:
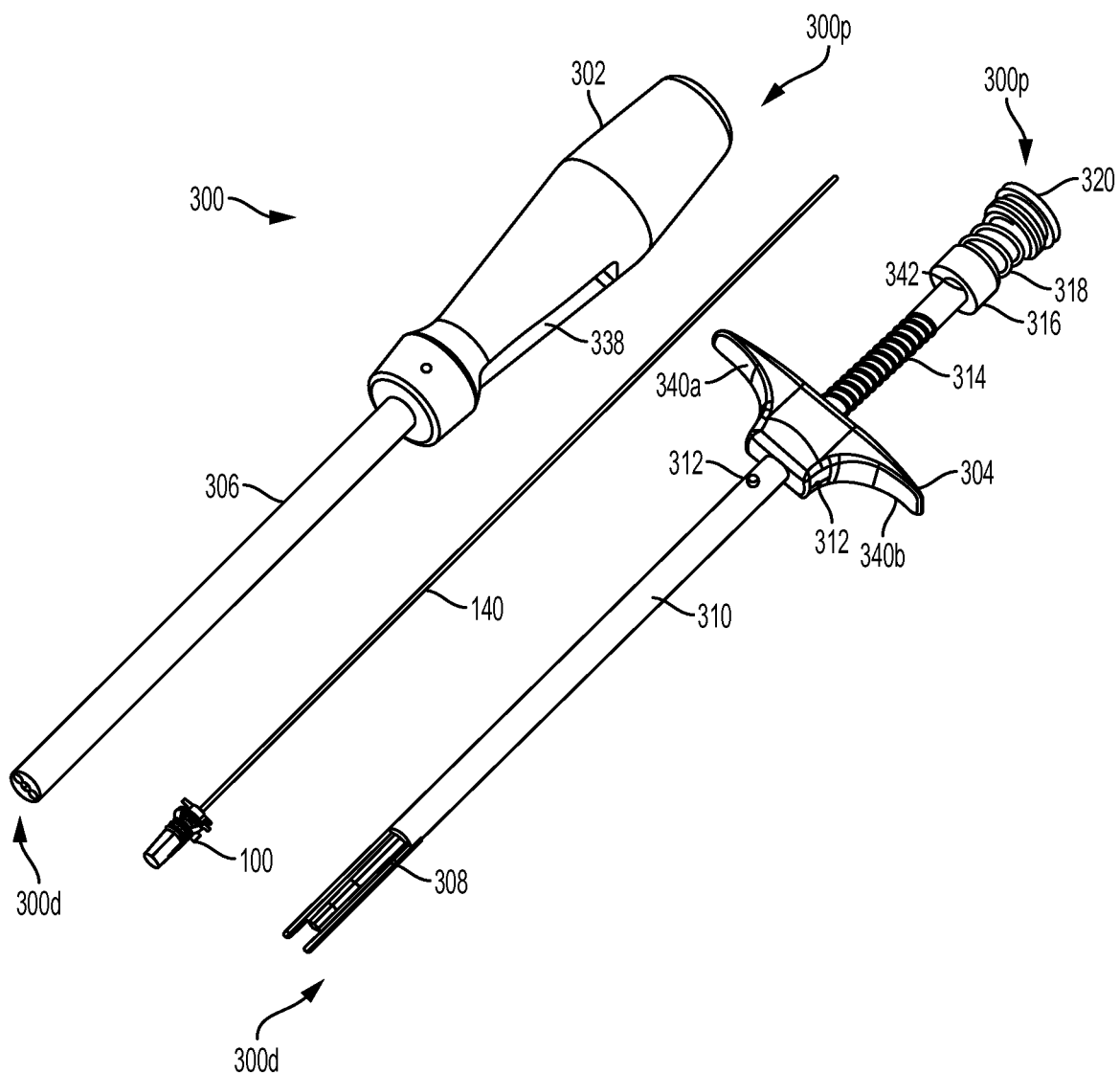
FIG. 11A is an exploded perspective view of the inserter tool of FIG. 1.

As indicated above and further shown in FIG. 7, the interior of the sheath 100 can have a bore 120 formed in the solid distal tip of the sheath 100. The bore 120 can be configured to receive the guidewire 140. The sheath 100 can be pre-packaged on the guidewire 140 to enhance ease of use during the surgical procedure. In an exemplary embodiment, as shown in FIG. 11A, the guidewire 140 has a predetermined length that is sufficient to allow the guidewire to mate to the sheath and to extend all the way through and into the handle portion of each of the inserter and the driver. The guidewire can also have a threaded distal tip 142 that is configured to mate with threads (not shown) formed in the bore 120 in the sheath 100. In one embodiment, the bore 120 is a blind bore such that the guidewire 140 does not protrude through the distal end 100d and is retained inside the sheath 100. In an alternate embodiment, the bore can extend entirely through the distal tip thereby allowing the guidewire 140 to protrude through the end of the sheath 100.

As further shown in FIG. 7, the sheath 100 can include features formed on the internal surface of the sidewalls 112a, 112b. For example, the sidewalls 112a, 112b can include threads 124 formed on the inner facing surfaces thereof for threadably mating with the screw 200. In some embodiments, the threads can extend along a portion of the interior of the sidewalls 112a, 112b or fully along the interior of the sidewalls 112a, 112b. Further internal features can include but are not limited to ridges, engagement members, or detents that could be used to assist the sheath 100 in pulling or engaging the screw 200 into its final position. In an exemplary embodiment, the threads 124 are shaped to match threads on the screw 200 when the sheath 100 is in the expanded state, not the resting state, as will be discussed in more detail below.

In some embodiments, the sheath 100 can include anti-plunge tabs formed at the proximal end 100p. For example, FIGS. 2-7 illustrate four anti-plunge tabs 110a, 110b, 110c, 110d that each have a generally rectangular configuration and that extend radially outward from a proximal end 100p of the sheath 100 to prevent over insertion of the sheath 100 into the bone hole. In particular, first and second anti-plunge tabs 110a, 110b extend from opposed sides of the first sidewall 112a, and third and fourth anti-plunge tabs 110c, 110d extend from opposed sides of the second sidewall 112b. The anti-plunge tabs 110a, 110b, 110c, 110d are thus positioned adjacent to the slots 114a, 114b. The anti-plunge tabs 110 preferably extend radially outward from the sheath 100 beyond a maximum outer dimension or diameter of the sheath so as to act as a stop that limits the insertion depth of the sheath into a bone hole.

Figure 42A:
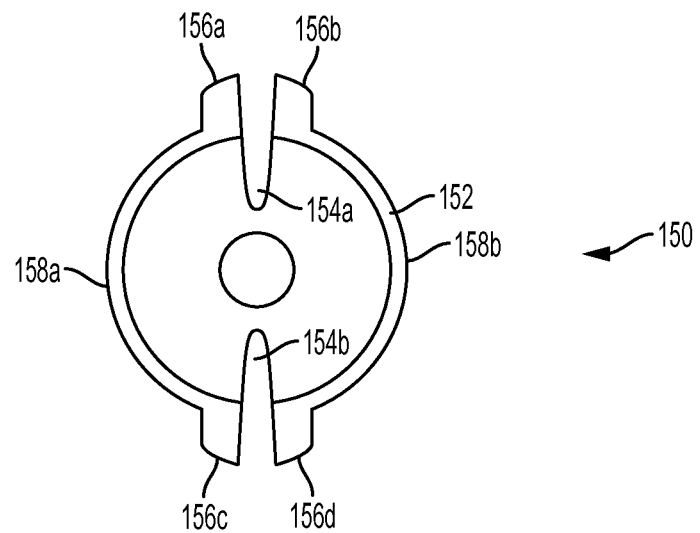
FIG. 42A is a top view of another embodiment of a sheath having anti-plunge tabs.
Figure 42B:
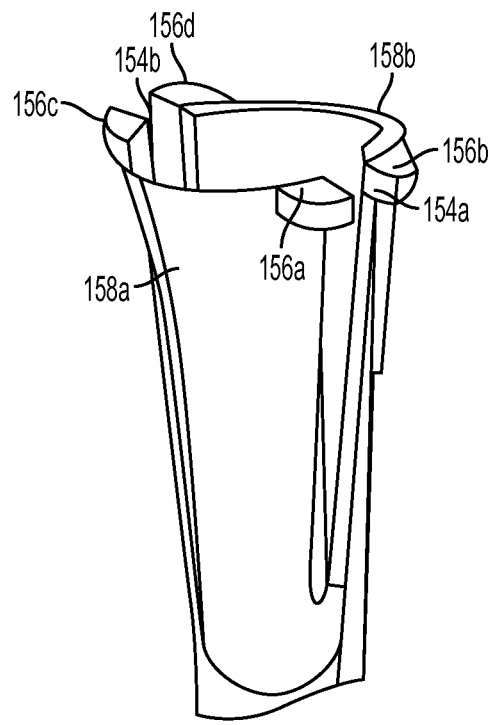
FIG. 42B is a side perspective view of the sheath of FIG. 42A.
Figure 42C:
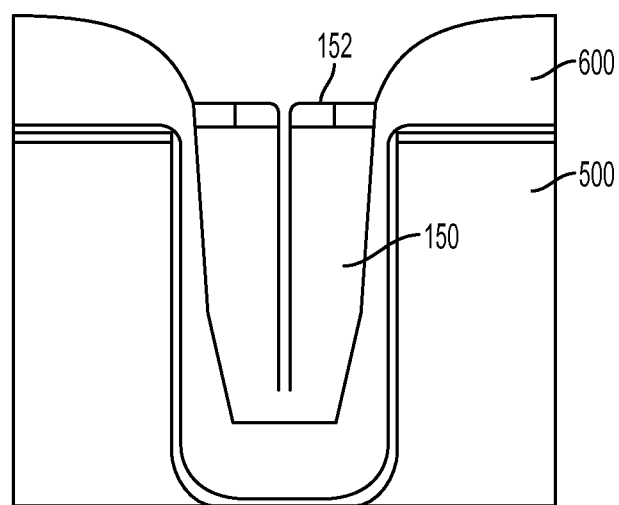
FIG. 42C is a side perspective view of the sheath of FIG. 42A disposed in a bone hole and shown anchoring a tendon to the bone.
Figure 42D:
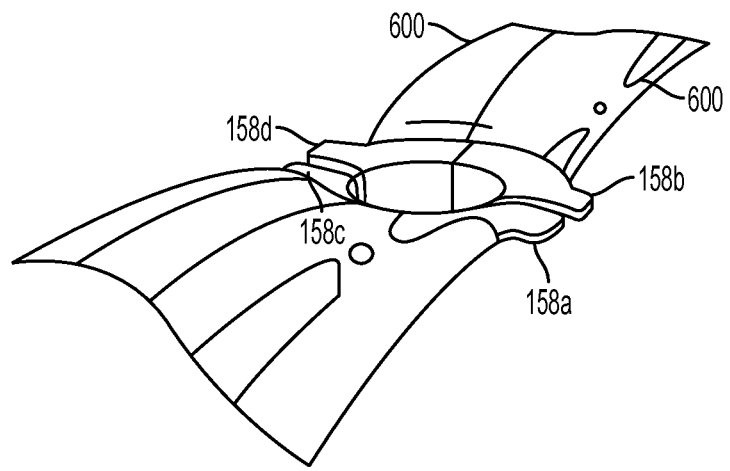
FIG. 42D is a top view of the sheath and tendon of FIG. 42C.

FIGS. 42A-42D illustrate another embodiment of a sheath 150 having anti-plunge tabs 156a, 156b, 156c, 156d formed at a top proximal end 150p. For example, FIG. 42A is a top view of a sheath having two pairs of anti-plunge tabs 156a, 156b, 156c, 156d that extend radially outward from opposed sides of the sheath 150. In particular, as shown in FIG. 42B, first and second tabs 156a, 156c extend from opposed sides of a first sidewall 158a, and third and fourth tabs 156b, 156d extend from opposed sides of a second sidewall 158b. The tabs 156a, 156b, 156c, 156d are positioned adjacent to slots 154a, 154b that separate the sidewalls 158a, 158b. The forked prongs of the inserter tool, discussed in further detail below, can mate with the slots 154a, 154b to insert the sheath 150 into the bone hole. In use, as shown in FIG. 42C, the top surface 152 of the sheath 150 or the proximal end 150p is configured to remain above the top surface of the bone 500. As shown in FIG. 42D, the anti-plunge tabs 156a, 156b, 156c, 156d will abut the top surface of the bone, extending beyond the bone hole to limit the insertion depth of the sheath 150 into the bone hole. The tabs 156a-d are preferably oriented such that they are positioned on opposite sides of the tendon, i.e., in a direction perpendicular to the tendon. For example, first and second tabs 156a, 156b can be position proximate to the left side of the tendon 600l and the third and fourth tabs 156c, 156d can be positioned proximate to the right side of the tendon 600r. The anti-plunge tabs 156a, 156b, 156c, 156d can compress the tendon against the bone to facilitate anchoring of the tendon to the bone.

Figure 43A:
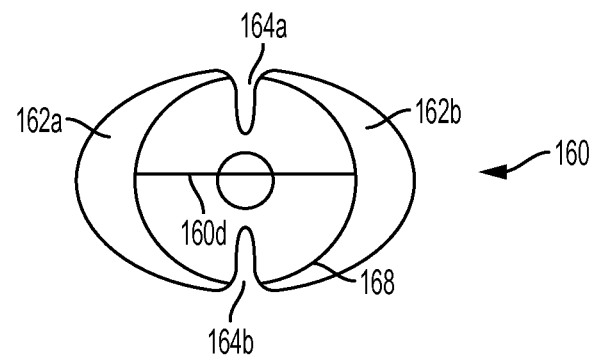
FIG. 43A is a top view of another embodiment of a sheath having a proximal flange.
Figure 43B:
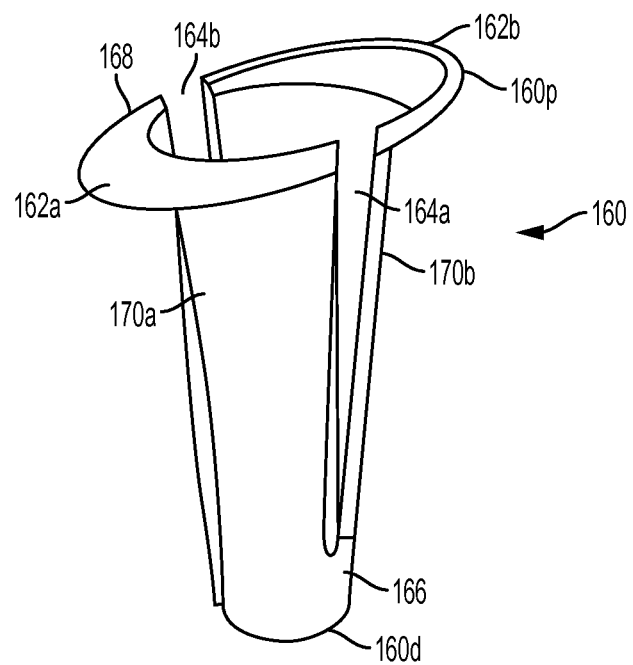
FIG. 43B is a side perspective view of the sheath of FIG. 43A.
Figure 43C:
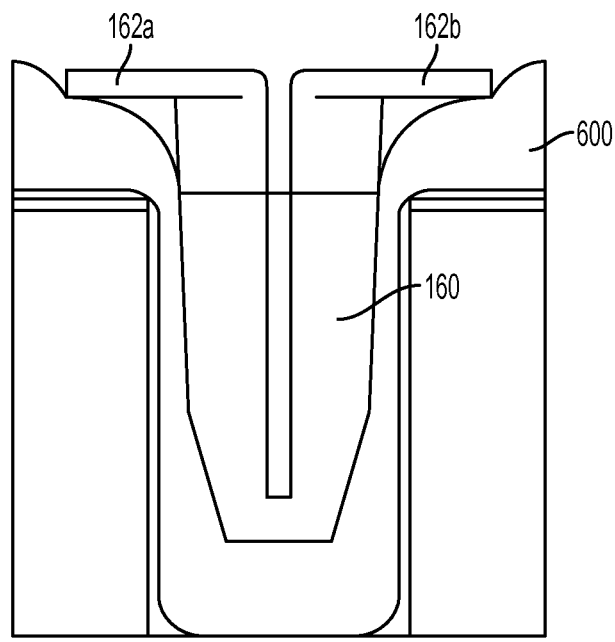
FIG. 43C is a side perspective view of the sheath of FIG. 43A disposed in a bone hole and shown anchoring a tendon to the bone.
Figure 43D:
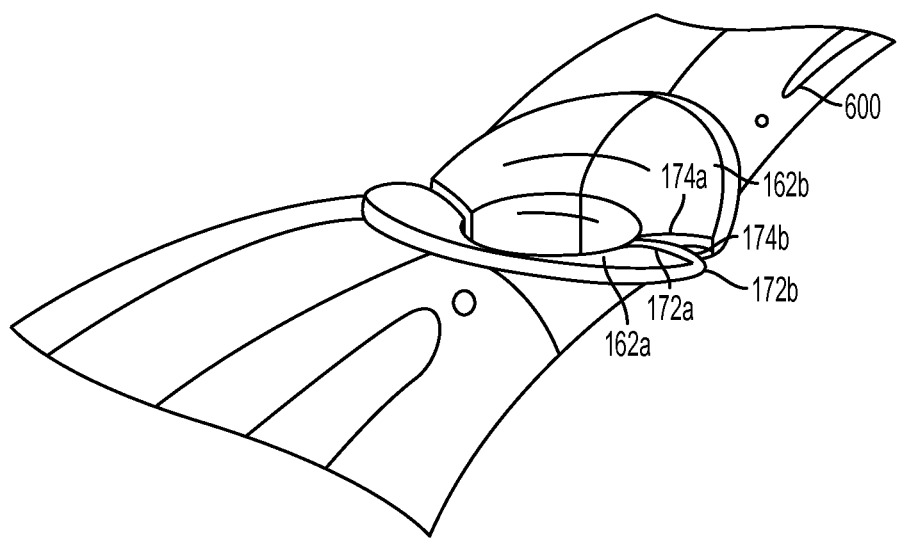
FIG. 43D is a top view of the sheath and tendon of FIG. 43C.

FIGS. 43A-43D illustrate another embodiment of a sheath 160 having an anti-plunge feature. In this embodiment, the proximal end 160p of the sheath 160 includes proximal flanges 162a, 162b extending radially outward from the proximal surface 168 of each sidewall. In particular, the first and second proximal flanges 162a, 162b can extend from opposite sides beyond the diameter 160D of the sheath 160. As shown in FIG. 43B, the sheath 160 can include opposed elongate slots 164a, 164b extending from the proximal end 160p toward the distal end 160d. The elongate slots 164a, 164b can terminate just proximal to the solid distal tip 166 and can be configured to couple to an inserter tool, as will be discussed in further detail below. As shown in FIGS. 42A and 42B, the first flange 162a can extend between the first and second elongate slots 164a, 164b, extending circumferentially around the perimeter of the proximal surface 168 of the first sidewall 170a. The second proximal flange 162b can also extend between the first and second elongate slots 164a, 164b, extending circumferentially around the perimeter of the proximal surface 168 of the second sidewall 170b. The flanges 162a, 162b can each have a generally semi-circular or oblong shape. As shown by FIG. 43C, when the sheath is implanted in a bone hole, the tendon 600 will be engaged between the proximal flanges 162a, 162b and the surface of the bone. The proximal flanges 162a, 162b can thus be positioned on the top surface of the tendon 600 covering the bone. The proximal flanges 162a, 162b can be formed from a flexible material and can be configured to provide relief to the tendon by flexing. As shown in FIG. 43D, the outer edges 172b, 147b of the proximal flanges 162a, 162b can flex upward away from the surface of the bone while the inner edges 172a, 174a of the proximal flanges 162a, 162b located proximate to the elongated slots 164a, 164b can flex downward toward the bone hole pressing the tendon 600 into place. In this embodiment, the flanges 162a, 162b are oriented in-line with the tendon, such that the first flange 162a extends across the tendon along one side of the bone hole, i.e., the distal side, and the second flange 162b extends across the tendon along the opposite side of the bone hole, i.e., the proximal side.

Figure 4:
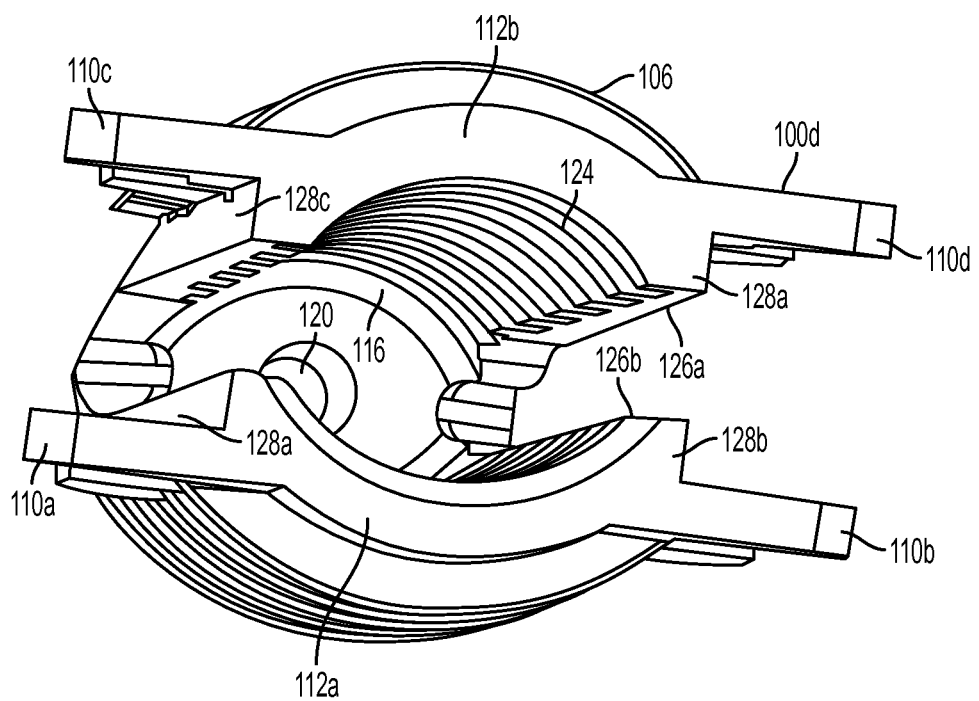
FIG. 4 is a top view of the sheath of FIG. 1.
Figure 5A:
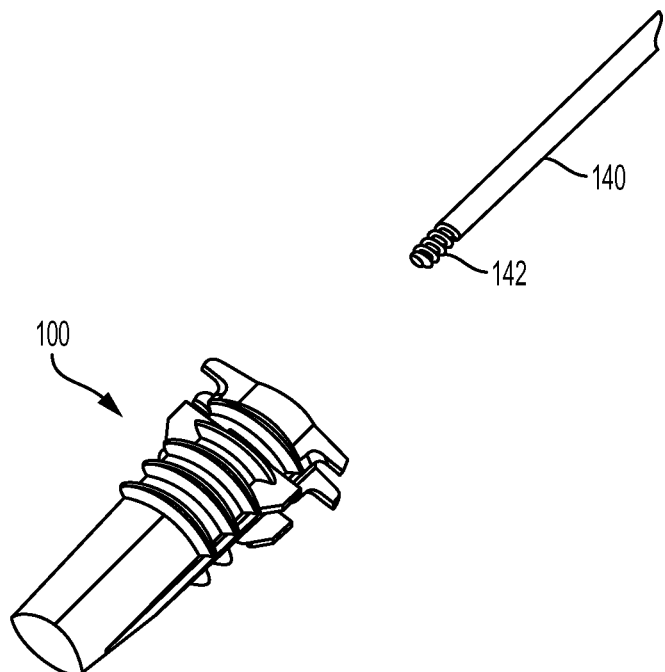
FIG. 5A is perspective view of the sheath of FIG. 1 shown with a guide wire for mating thereto.
Figure 5B:
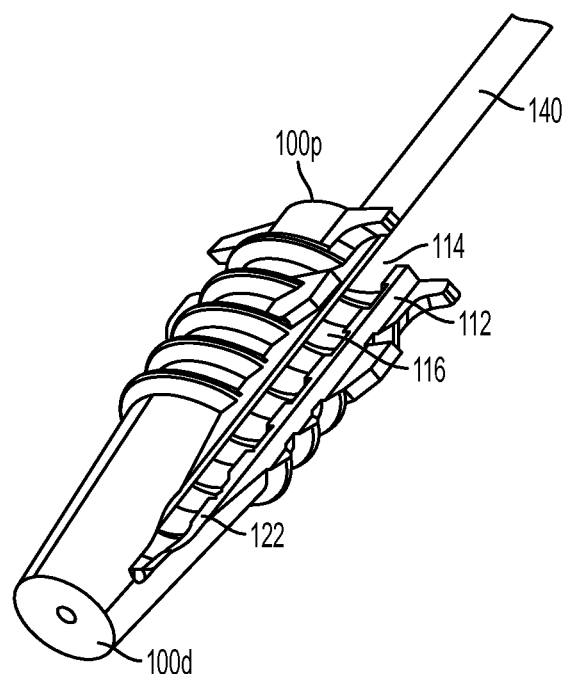
FIG. 5B is a side perspective view of the sheath and the guide wire of FIG. 5A shown mated.

Referring back to the embodiment of FIG. 2, the sheath 100 can further include cortical retaining tabs 108a, 108b positioned along the mid-section of the sheath 100, e.g., at a location just distal to the proximal end 100p. The cortical retaining tabs 108a, 108b are preferably positioned about 2 mm from the proximal-most end such that the cortical retaining tabs 108a, 108b will be positioned just beyond cortical bone and within cancellous bone when the sheath 100 is implanted in a bone hole. The cortical retaining tabs 108a, 108b can be sized to match a diameter of the bone hole. This allows the cortical retaining tabs 108a, 108b to be passed into the bone hole. In other words, the cortical retaining tabs 108a, 108b can have an outer diameter that is equal to or less than a maximum outer dimension or diameter of the sheath 100. Once implanted and after insertion of the screw into the sheath 100, the sheath will expand to cause the cortical retaining tabs 108a, 108b, or at least an outer corner thereof, to extend under a surface of the cortex to prevent pull out thereby locking the sheath 100 into the bone. In the illustrated embodiment, the sheath 100 includes four cortical retaining tabs 108a, 108b, 108c, 108d, with two on opposite sides of each sidewall 112a, 112b. However, the sheath 100 can include any number of cortical retaining tabs 108a, 108b As shown in FIG. 4, the sheath 100 can also include anti-collapse tabs 128a, 128b, 128c, 128d integrally formed or positioned on the interior walls 126a, 126b for preventing collapse of the walls 126a, 126b beyond a predetermined position. In the illustrated embodiment, an edge of each of the first and second sidewalls 112a, 112b, extending adjacent to the first and the second elongate slots 114a, 114b, define four anti-collapse tabs. The tabs can move toward one another, but they act as a stop to prevent the sidewalls 112a, 112b from fully collapsing. The tabs 128a, 128b, 128c, 128d can thus allow the sidewalls to collapse toward one another when the sheath 100 and tendon are inserted into bone but prior to completion of the procedure and the insertion of the screw 200.

Figure 8A:
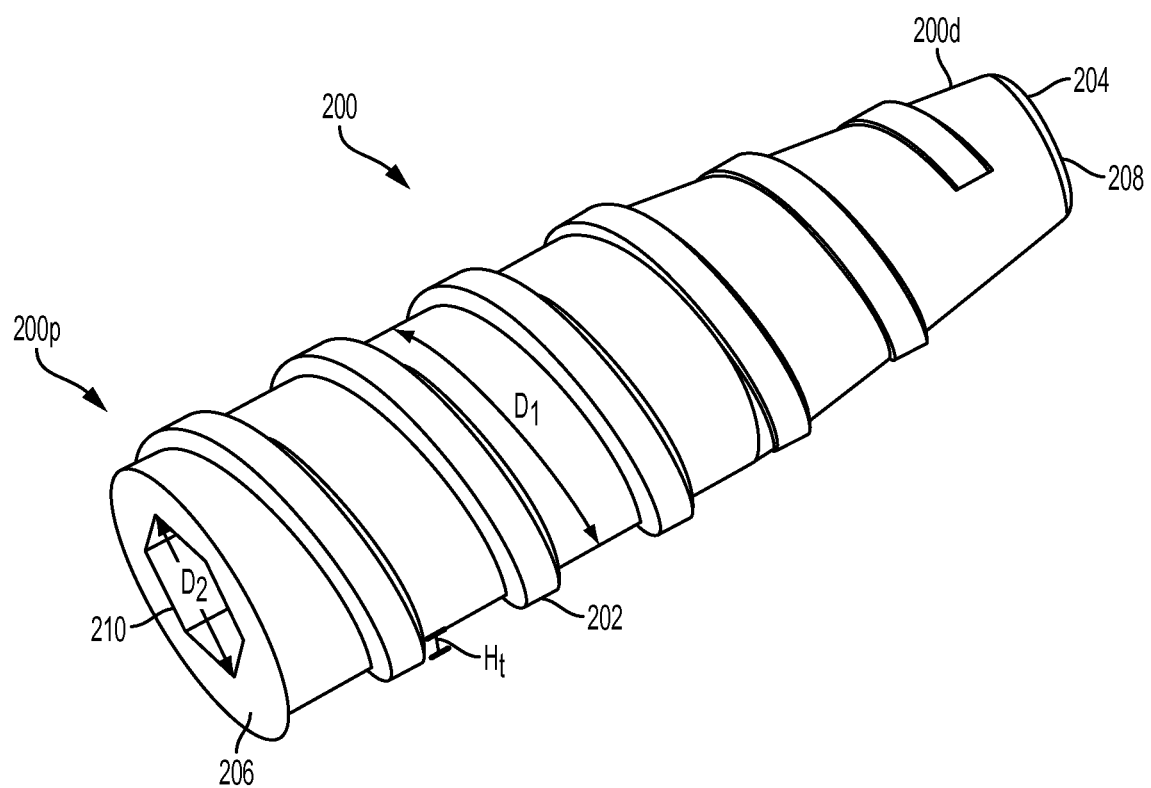
FIG. 8A is a side perspective view of the expander screw of FIG. 1.
Figure 9:
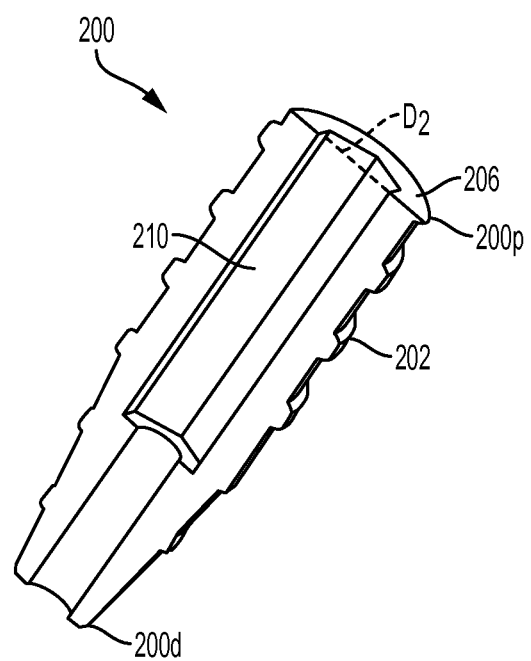
FIG. 9 is a cross-sectional perspective view of the expander screw of FIG. 1.
Figure 10:
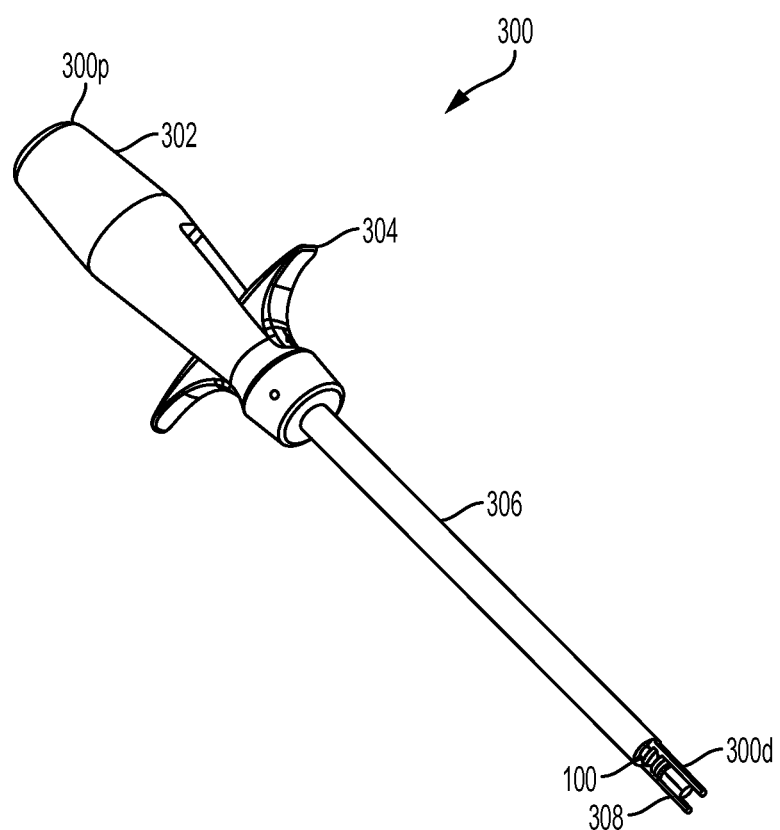
FIG. 10 is a perspective view of the inserter tool of FIG. 1.

As indicated above, the sheath 100 is configured to receive a screw 200 therein that is effective to expand the sheath 100 to anchor the sheath 100 and ligament coupled thereto within a bone hole. As shown in FIG. 8A, in one embodiment the screw 200 can have a generally cylindrical shape with a constant minor diameter $D_1$ along at least a proximal portion 200p, and preferably along a majority of the length, e.g., more than half of the total length. A distal portion 200d of the screw 200 can taper distally inward to a reduced diameter at the distal-most end. The screw 200 can have threads 202 formed there along and extending along the entire length to facilitate engagement with the sheath 100. The screw 200 can be fully cannulated for allowing the screw 200 to be delivered over a guidewire 140, and the screw 200 can have a flat proximal facing surface 206 and a flat distal facing surface 208. The proximal surface 206 and the distal surface 208, however, can have various shapes and the shape can be configured to conform to the sheath and/or the bone surface. As further shown in FIGS. 8A and 9, the inner lumen 210 can have a diameter that is sized to receive a guidewire. At least a proximal portion of the inner lumen 210 can be shaped to receive a driver tool. For example, as shown in FIG. 8A, the proximal portion 200p can have a hexagonal bore to receive a hexagonal drive tool.

Referring back to FIG. 1, the screw 200 can be inserted into the sheath 100 during use. Upon insertion into the sheath 100, the screw 200 can cause the sheath 100 to expand. In an exemplary embodiment, the threads 202 on the screw 200 have a height $H_t$ (FIG. 8) that is less than a height $H_g$ (FIG. 6) of the internal threads 124 formed in the sheath 100. This configuration will allow the minor diameter $D_1$ of the screw 200 to contact the inner minor diameter D1 (FIG. 6) of the sheath 100 and thereby cause expansion of the sheath 100. As a result, the threads 202 are not sized to cause expansion of the sheath 100, and rather than minor diameter of the screw 200 causes expansion. Additionally, the screw 200 can be shaped to cause the thicker mid-portion of the sheath 100 to expand radially outward by a distance that is greater than the proximal end 100p and the distal end 100d of the sheath, such that the mid-portion 100m forms the largest diameter of the sheath 100 in the expanded state, as previously discussed with respect FIG. 7.

Figure 8B:
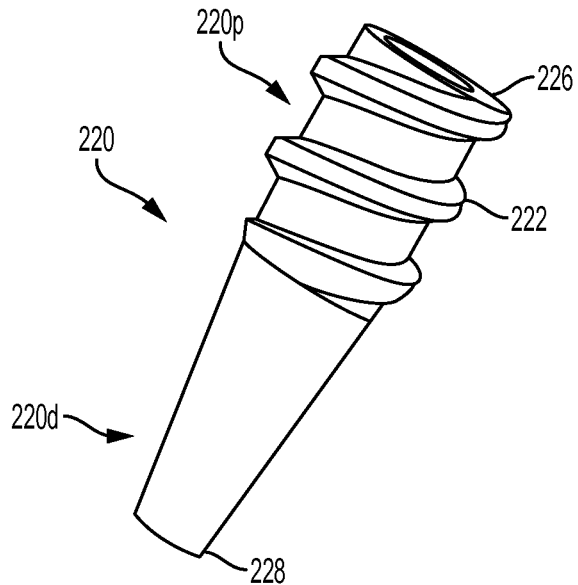
FIG. 8B is a side perspective view of another embodiment of an expander that is configured to be partially non-rotatably advanced into a bone hole and then rotatably advanced into the bone hole.

A person skilled in the art will appreciate that the expander can have a variety of other configurations, and the expander can be configured to be non-rotatably inserted into the sheath, rotatably inserted into the sheath, or partially non-rotatably and partially rotatably inserted into the sheath. FIG. 8B illustrates one embodiment of an expander 220 that is configured to be partially non-rotatably inserted into the sheath and then rotatably inserted into the sheath. In particular, the expander 220 includes a proximal portion 220p having threads 222 formed thereon, and a distal portion 220d that is non-threaded and free of surface features. The length of the proximal and distal portions 220p, 220d can vary, but in an exemplary embodiment each portion is about half of the entire length of the expander 220. The illustrated proximal portion 220p has a generally cylindrical shape with a constant minor diameter $D_1$, and the distal portion 220d of the expander 220 tapers distally inward to a reduced diameter at the distal-most end. The expander 220 can be fully cannulated for allowing the expander 220 to be delivered over a guidewire 140, and the expander 220 can have a flat proximal facing surface 226 and a flat distal facing surface 228. In use, the non-threaded distal portion 220d of the expander 220 can be non-rotatably advanced into the sheath 100. Once the distal portion 220d is fully disposed within the sheath 100, the expander 220 can then be rotated to thread the proximal portion 220p into the sheath. The sheath can include corresponding threads along an entire inner surface thereof, or along on a proximal portion of the inner surface thereof, for mating with the threads 222 on the expander 220.

Figure 8C:
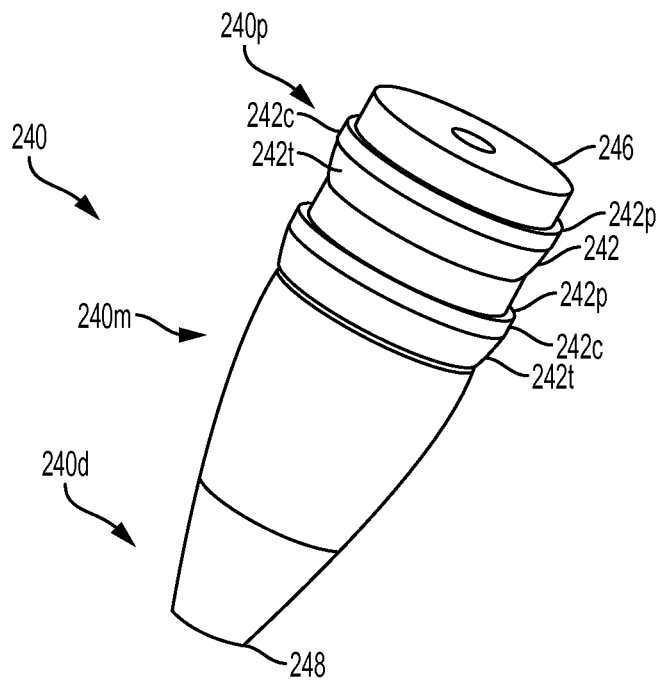
FIG. 8C is a side perspective view of another embodiment of an expander that is configured to be non-rotatably advanced into a bone hole.

FIG. 8C illustrates another embodiment of an expander 240 that is configured to be non-rotatably advanced into a sheath. In general, the expander 240 has a generally cylindrical shape with a constant minor diameter $D_1$ along a proximal portion 240p and a convex belly along a mid-portion 240m to a distal portion 240d. The distal portion 240d of the expander 240 is tapered distally inward to a reduced diameter at the distal-most end. The mid-portion 240m and the distal portion 240d can be free of any surface features and can be relatively smooth. The proximal portion 240p, on the other hand, can include one or more ribs or flanges 242 formed thereon and extending circumferentially therearound. In the illustrated embodiment, the proximal portion 240p includes two ribs 242 formed thereon and spaced longitudinally apart. Each rib 242 includes a flat proximal-facing surface 242p, and an outer sidewall having a proximal constant diameter portion 242c and a distal tapering portion 242t. The ribs 242 have an outer diameter that is greater than the minor outer diameter of the expander 240. The expander 240 can be fully cannulated for allowing the expander 240 to be delivered over a guidewire 140, and the expander 240 can have a flat proximal facing surface 246 and a flat distal facing surface 248. In use, the expander 240 can be non-rotatably advanced into the sheath 100. The ribs 242 on the proximal portion 240 can cause the sheath to expand outward thereby anchoring the sheath within the bone hole.

Sheath Inserter

Various inserter tools are also provided for inserting the sheath 100 and/or screw 200 into a bone hole. The inserter tool can also be used to perform various other functions in connection with insertion of the sheath into a bone hole. For example, the anchor inserter tool can be effective to initially measure a size of a tendon. Multiple inserter tools having different sizes can be provided, with the sizes corresponding to the appropriately sized sheath and screw to be used therewith. The inserter tool can also be configured to insert or "plunge" a tendon into a pre-drilled bone hole, and to maintain the tendon within the bone hole while delivering a sheath 100 into the bone hole. The inserter tool can further be configured to receive a guidewire 140 therein that is coupled to the sheath 100. This can allow the sheath 100 with the guidewire 140 mated thereto to be delivered into a bone hole, and the guidewire 140 can thereafter remain with the sheath 100 and facilitate delivery of the an expander into the sheath. In certain exemplary embodiment, the inserter tool can be configured to fixedly engage the guidewire 140 to prevent movement thereof during plunging of the tendon and during delivery of the sheath 100, and it can be configured to selectively release the guidewire 140 once the sheath 100 is implanted to allow the tool to be removed from the guidewire 140, leaving the sheath 100 implanted with the guidewire 140 extending therefrom.

FIGS. 10-17 illustrate one exemplary embodiment of a sheath inserter tool 300 and various components and features thereof. As shown, the sheath inserter tool 300 generally includes an outer component having a handle 302 with an outer shaft 306 extending therefrom, and an inner component that includes a trigger 304 that is slidably coupled to the handle 302 and an inner shaft 310 extending from the trigger 304 and through the outer shaft 306. The inner shaft 310 includes features for interacting with the sheath. The sheath inserter tool 300 can also include features disposed within the handle 302 for controlling movement of the inner and outer shafts 310, 306 relative to one another, as will be discussed in more detail below.

The handle 302 can have a variety of configurations, but in the illustrated embodiment the handle 302 on the outer component has a generally elongate cylindrical configuration to facilitate grasping thereof. The handle 302 can have a bore extending therethrough from the distal end 302d and terminating just distal to the proximal-most end. In other embodiments, however, the bore can extend through the proximal end of the handle 302. The bore can be configured to receive various components for controlling movement of the inner and outer shafts relative to one another. A distal portion of the bore can receive the proximal end of the outer shaft 306 for mating the shaft to the handle. The handle 302 can further include elongate longitudinal cut-outs 338a, 338b formed in opposite sidewalls thereof and in communication with the inner lumen. The cut-outs 338a, 338b can allow the trigger 304 on the inner component to extend therethrough and to slidably move there along.

The trigger 304 can also have various configurations, but as shown the trigger 304 is generally T-shaped and includes distal facing finger-gripping surfaces 340a, 340b. The trigger 304 extends laterally outward from opposed sides of the handle 302, through the cut-outs 338a, 338b, and thus allows a user to place the proximal end 300p of the handle 302 in their palm and to grasp the trigger 304 with two fingers to pull the trigger 304 proximally. The trigger can thus slide proximally and distally relative to the handle. As further shown in FIG. 11A, the trigger 304 can be fixedly mated to or integrally formed on the proximal end of the inner shaft 310. As a result, movement of the trigger 304 relative to the handle 302 moves the inner shaft 310 relative to the outer shaft 306.

As indicated above, the handle can include additional features for controlling movement of the inner and outer components relative to one another. As shown in FIG. 11A, the handle 302 includes a primary biasing member 314 e.g., a spring, disposed therein and configured to apply a distal biasing force to the trigger 304. The primary biasing member 314 thus pushes the trigger 304 and thus the inner shaft 310 distally. In order to move the trigger 304 and the inner shaft 310 proximally relative to the handle 302 and outer shaft 306, the biasing force must be overcome to cause compression of the primary biasing member 314. In an exemplary embodiment, a first force can be applied to move the trigger 304 in a proximal direction along a first range of motion, i.e., a first distance, to cause at least partial compression of the primary biasing member 314. The trigger 304 can also move further proximally along a second range of motion, i.e., a second distance, however the handle 302 can be configured to prevent proximal movement beyond the first range of motion unless a second force is applied to the trigger, 304 with the second force being greater than the first force. The second biasing member 318, e.g., a spring can provide the second force for proximal movement beyond the first range of motion. As shown in FIG. 11A, the secondary biasing member 318 is located proximal to the primary biasing member 314.

The handle can also include a feature for engaging the guidewire mated to the sheath. In one embodiment, a guidewire retainer or a guidewire grasper 316 can be disposed between the primary and second biasing members 314, 318. The guidewire retainer 316 can include a bore 342 formed therein that is configured to receive a proximal end of the guidewire 140 mated to the sheath 100. The bore 342 is preferably sized to engage the guidewire 140 by compression fit to hold the guidewire 140 in a fixed position. In one embodiment, the guidewire retainer 316 can be formed from a compressible material to engage the guidewire. A person skilled in the art will appreciate, however, that other techniques can be used to engage the guidewire. The guidewire grasper can move axially within the handle and proximal movement to a certain position can cause the guidewire grasper to release the guidewire. The secondary biasing member 318 can apply the distally-directed biasing force to the guidewire retainer 316 to prevent proximal movement of the guidewire retainer until the second force is applied to cause the retainer to move proximally and release the guidewire.

In order to allow the secondary biasing member to apply a secondary force, the proximal end of secondary biasing member 318 can define an abutment surface. In particular, as shown, the handle 302 can include a proximal-most member, e.g., a handle plunge 320, that abuts the proximal-most inner surface of the handle 302, and that allows the secondary biasing member 318 to be compressed between it and the guidewire retainer 316. In use, when the trigger 304 is moved proximally by a first distance, through the first range of motion, the primary biasing member 314 compresses. The secondary biasing member 318 applies a biasing force to the guidewire retainer 316 that is sufficient to prevent proximal movement of the guidewire retainer 316, and thus to resist movement of the trigger 304 beyond the first range of motion. When desired, a greater force can be applied to move the trigger 304 further proximally through the second range of motion. The greater force needs to be sufficient to overcome the biasing force of the secondary biasing member 318. When the trigger 304 is moved further proximally, beyond the first range of motion and through the second range of motion, the guidewire retainer 316 will move proximally to cause the secondary biasing member 318 to compress. As will be discussed in further detail below, proximal movement of the guidewire retainer 316 will release the guidewire 140, as the mating connection between the sheath 100 and guidewire 140, and abutment of the sheath 100 against the distal end of the outer shaft 306, will prevent the guidewire 140 from moving proximally with the guidewire retainer 316. The sheath inserter tool 300 can thus be removed, leaving the guidewire 140 behind.

Figure 11B:
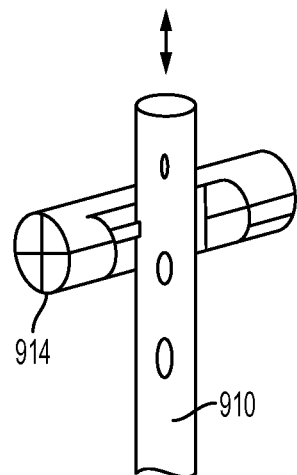
FIG. 11B is a perspective view of one embodiment of a locking mechanism for use with the inserter tool of FIG. 1.
Figure 11C:
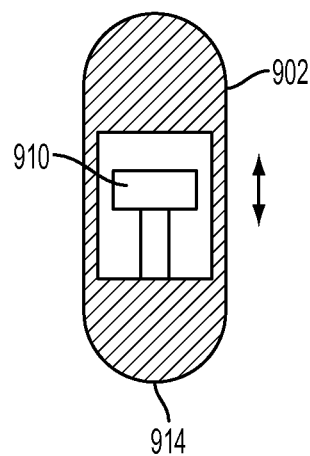
FIG. 11C is a side view of the locking mechanism of FIG. 11B.

A person skilled in the art will appreciate that the handle can include other features, such as a locking mechanism, for releasably locking the inner and outer components to one another. By way of non-limiting example, FIGS. 11B and 11C illustrate one embodiment of a locking mechanism that could be located on the handle 302 and configured to engage a proximal portion of the inner shaft 310. The locking mechanism includes a lock 914 which can be disposed at various locations on the handle 302. The lock 914 is generally in the form of an elongate shaft having a cut-out formed therein. The cut-out includes a longitudinally extending pin that is configured to be moved in and out of a hole in the proximal end of the inner shaft 310. When the lock 914 is pushed toward one side of the handle 302 and the pin extends through a hole, the inner shaft is prevented from movement. Conversely, when the lock 914 is pushed toward the other side of the handle such that the pin is removed from the hole, the inner shaft is free to move. Accordingly, when in a locked position, the lock 914 prevents proximal movement of the actuator and locks the inner and outer shafts from moving longitudinally with respect to each other. When in the unlocked position, the actuator and the inner shaft 310 can move proximally relative to the handle 302 and outer shaft 306. A person skilled in the art will appreciate that a variety of other locking mechanisms known in the art can be used to lock the inner and outer components relative to one another.

Figure 12A:
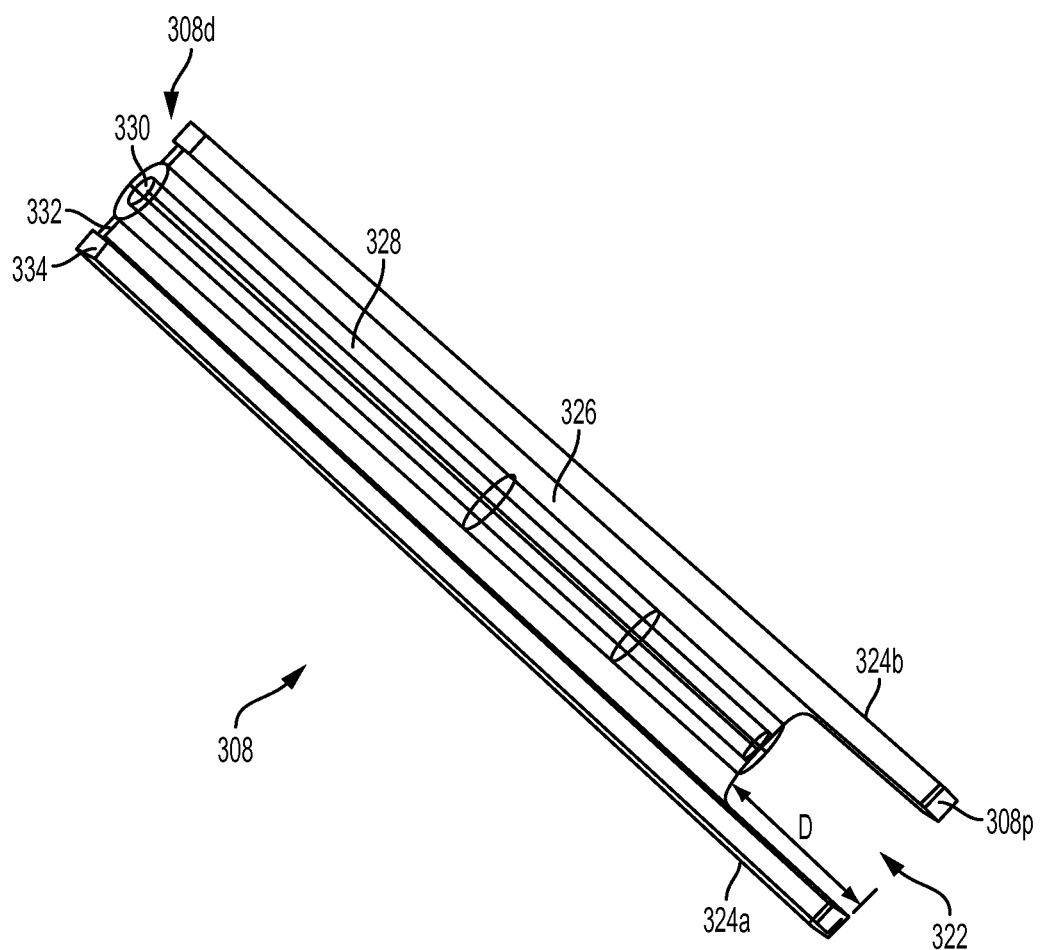
FIG. 12A is a partially transparent perspective view of a distal fork of the inserter tool of FIG. 1.
Figure 12B:
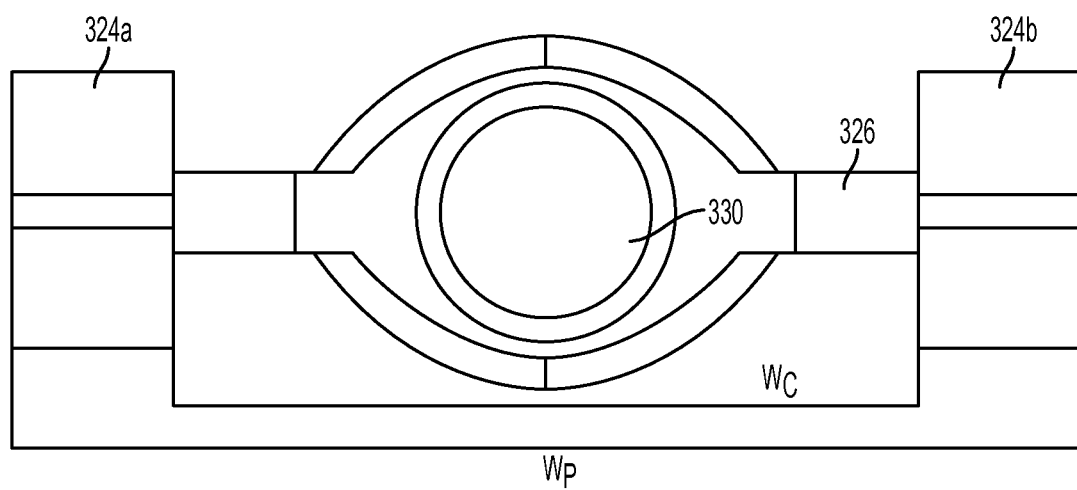
FIG. 12B is an end view of the distal fork of the inserter tool of FIG. 1.

As indicated above, the inner shaft 310 is coupled to and extends from the trigger 304 and can have a generally elongate cylindrical shape with a fork 308 on a distal end 300d thereof. The fork 308 can function to both measure a tendon, and to facilitate insertion of the tendon and sheath 100 into a bone hole. FIG. 12A is an enlarged transparent view of the fork 308, and FIG. 12B is an end view of the fork 308. As shown, the fork 308 includes first and second elongate prongs 324a, 324b that extending longitudinally along opposed sides of a cylindrical central portion 328. The elongate prongs 324a, 324b can each have a generally square or rectangular cross-sectional shape, and the prongs 324a, 324b can be coupled to the cylindrical central portion 328 by connectors 326 extending longitudinally along the entire length of the distal end. The connectors 326 can have a width We that is less than a width Wp of the prongs 324a, 324b. The central portion 328 can include a guidewire bore 330 or channel extending therethrough and sized to slidably receive the guidewire 140 mated to the sheath 100. The pair of prongs 324a, 324b can extending distally beyond the connectors 326 and the central portion 328 by a predetermined distance D to thereby define a u-shaped recess 322 between the pair of prongs 324a, 324b. The u-shaped recess 322 can be configured to receive the sheath 100 therein, with the prongs 324a, 324b extending into the opposed sidewall cut-outs in the sheath 100. In one embodiment, the u-shaped recess 322 can include a coned shaped protrusion formed therein to provide support to the sheath 100. The protrusion can have a cylindrical proximal portion with a tapering distal portion that decreases distally in diameter.

Figure 12C:
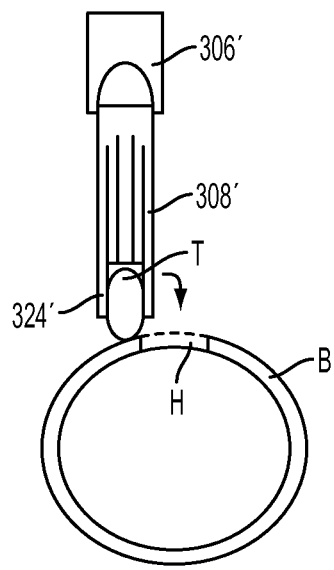
FIG. 12C illustrates another embodiment of an inserter tool having a fork with deformable prongs, showing the tool about to be inserted through a bone hole in bone.
Figure 12D:
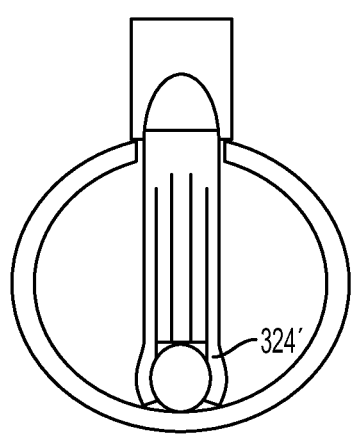
FIG. 12D illustrates the inserter tool of FIG. 12C inserted through the bone hole to cause the prongs on the fork to bow outward.

A person skilled in the art will appreciate that the first and second elongate prongs on the fork can have a variety of other configurations. FIGS. 12C and 12D illustrate an embodiment of an inserter tool that is similar to inserter tool 300 and includes an outer shaft 306' and an inner shaft (not shown) with a fork 308' on the distal end thereof. In this embodiment, the fork 308' has prongs 324' that are deformable and that can be configured to bow or flex outward into a generally convex configuration. The inner shaft and the fork 308' can configured to be locked relative to the outer shaft 306', and in use such a configuration can aid in dunking a sheath fully into a shallow bone hole, where the sheath length is less than the bone hole depth, but the overall length of the locked, extended retractable inserter forks are longer than the bone hole depth. In particular, FIG. 12C illustrates prongs 324' having a generally linear configuration. Once inserted through a bone hole H and into bone B, the locked, extended, retractable inserter fork 308' can have a length that allows the prongs 324' to abut against an opposite inner surface of the bone B. The prongs 324' can thus deform and bow outward, as shown in FIG. 12D. The outward expansion of the prongs 324' will occur below the near cortex, against the far interior cortical wall, thus aiding in anchoring the sheath (not shown) fully flush within the bone hole.

Figure 13:
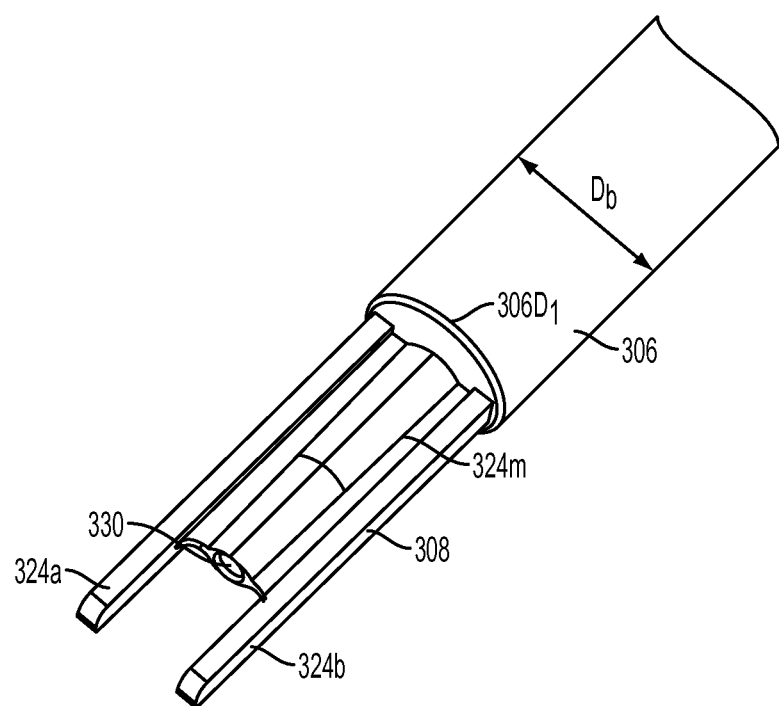
FIG. 13 is a perspective view of the distal fork and a portion of the outer shaft of the inserter tool of FIG. 1.

FIG. 13 illustrates the fork 308 extending from the distal end of the outer shaft 306. As shown, the outer shaft 306 has an outer diameter $D_b$ that is greater than a maximum width Wp of the prongs 324a, 324b. Such a configuration will allow the sheath proximal end to abut the outer shaft 306 distal end when the fork 308 is inserted into the sheath 100.

Figure 14A:
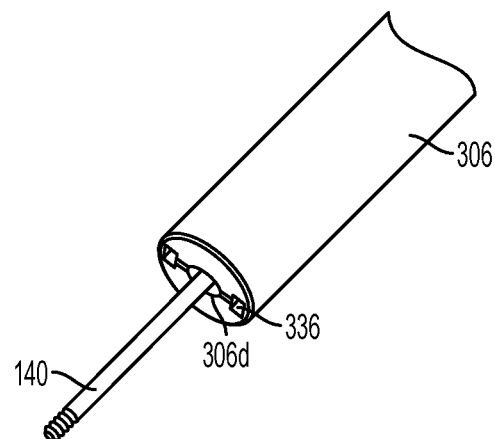
FIG. 14A is a perspective view of the guidewire of FIG. 5A extending from the outer shaft of the inserter tool of FIG. 1.

As indicated above, the inner shaft can move axially relative to the outer shaft to retract and extend the fork into and from the outer shaft 306. As shown in FIG. 14A, the barrel distal-facing end surface 306d can include a cut-out 336 formed therein that is shaped to match the shape of the fork 308 on the inner shaft 310. The cut-out 336 thus allows the fork 308 to be fully retracted into the outer shaft 306, as shown in FIG. 14A and also allows the guidewire 140 to be received therein. When fully assembled, the guidewire 140 and the sheath 100 mated thereto can be slid in a proximal direction into the distal end of the outer shaft 306. The guidewire 140 can be moved proximally until the proximal end of the guidewire 140 is received within and in engagement with the guidewire retainer 316 in the handle 302. The sheath will abut the distal end of the barrel to prevent further proximal movement of the sheath and the guidewire.

Figure 14B:
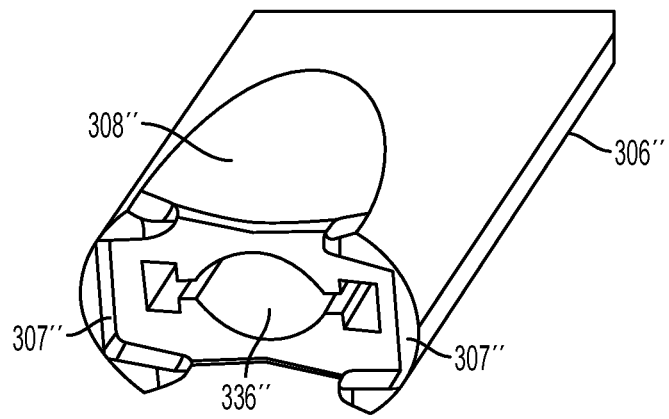
FIG. 14B is a perspective view of a distal end of an outer shaft of an inserter tool according to another embodiment.
Figure 14C:
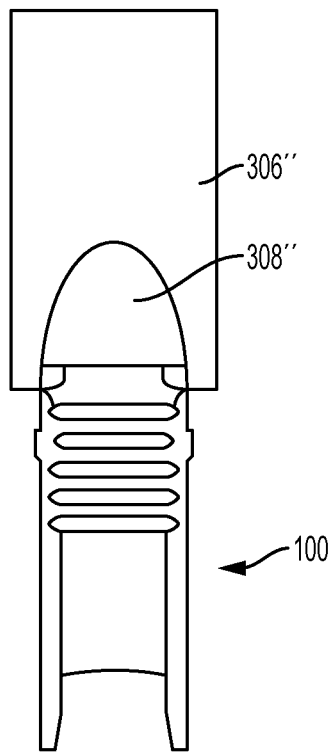
FIG. 14C is a side view of the outer shaft of FIG. 14B having a sheath coupled thereto.

In another embodiment, shown in FIGS. 14B and 14C, the outer shaft 306" can include cut-outs or recesses 307" that are configured to seat the anti-plunge tabs on the proximal end of the sheath 100. The recesses 307" can be formed on opposite sides of the cut-out 336" for allowing the anti-plunge tabs on the sheath to sit without the distal end of the outer shaft 306". As further shown in FIGS. 14A and 14B, the outer shaft 306" can also optionally include features to facilitate percutaneous insertion of the outer shaft 306" through tissue. For example, a concavity 308" (only one is shown) can be formed in opposite sides of the outer shaft 306" adjacent to the distal end to reduce the profile of the outer shaft and therefore facilitate insertion of the distal end through tissue. The concavity 308" in each sidewall can also seat the tendon, providing relief for the tendon during advancement of the sheath into the bone hole.

Figure 15:
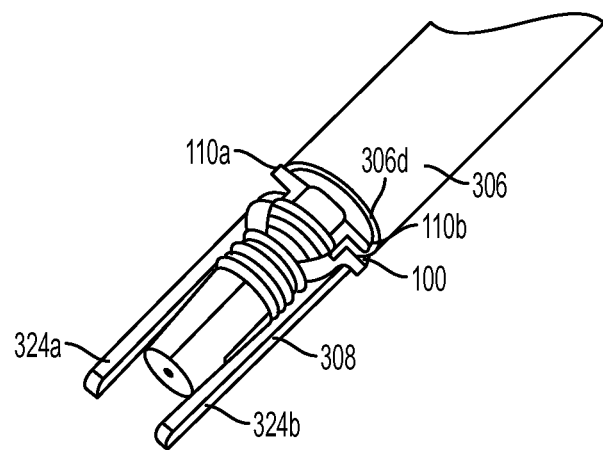
FIG. 15 is a side perspective view showing the sheath of FIG. 1 mounted onto the distal fork of the inserter tool of FIG. 1.

FIG. 15 illustrates the sheath 100 loaded onto the distal end of the inserter. As shown, the outer shaft 306 can have a diameter 306d that is greater than major diameter of the ribs on the sheath 100, and that is greater than a maximum width between the prongs 324a, 324b on the fork of the inserter tool. The outer diameter of the outer shaft 306 can be dimensioned with respect to the width of the anti-plunge tabs 110a, 110b, 110c, 110d so that the distal end of the outer shaft 306d can thus operate in conjunction with the anti-plunge tabs 110a, 110b, 110c, 110d on the sheath 100 to prevent over insertion of the sheath 100 into bone, as both the outer shaft 306 and the anti-plunge tabs 110a, 110b, 110c, 110d can abut the bone surface when the sheath is inserted into an appropriately sized bone hole. The bone hole is preferably reamed using a drill that is sized to correspond to the selected size of the sheath inserter tool 300. In particular, the bone hole can be reamed to have a diameter that is slightly greater than the diameter of the ribs 106a, 106b, 106c, 106d, 106e on the sheath 100, but less than the maximum width of the anti-plunge tabs 110a, 110b, 110c, 110d on the sheath 100. The distal end of the outer shaft 306 will also prevent proximal movement of the sheath 100 relative to the inserter tool, thereby maintaining the sheath and the guidewire attached thereto in a fixed position, as will be discussed below.

Figures 16A, 16B:
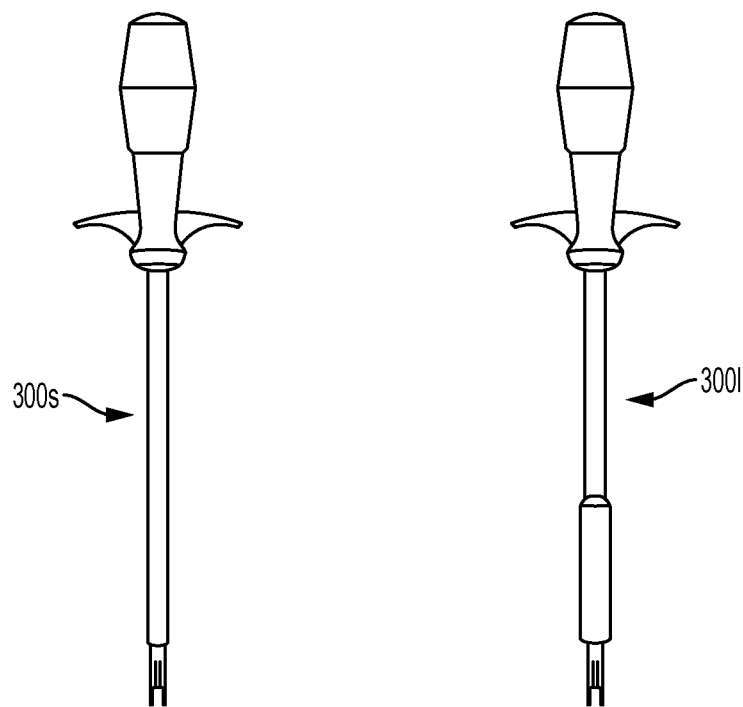
FIG. 16A is a side view of a size small inserter tool.
FIG. 16B is a side view of a size large inserter tool.
Figure 17A:
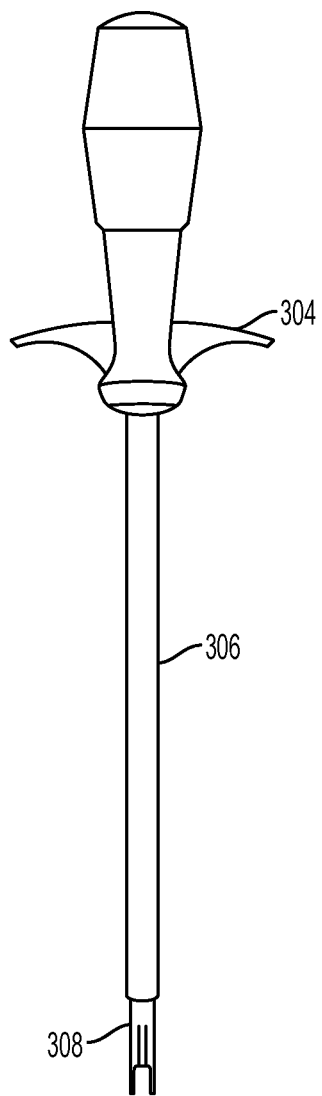
FIG. 17A is a side view of the inserter tool of FIG. 1, showing the inserter tool in an initial position.
Figure 17B:
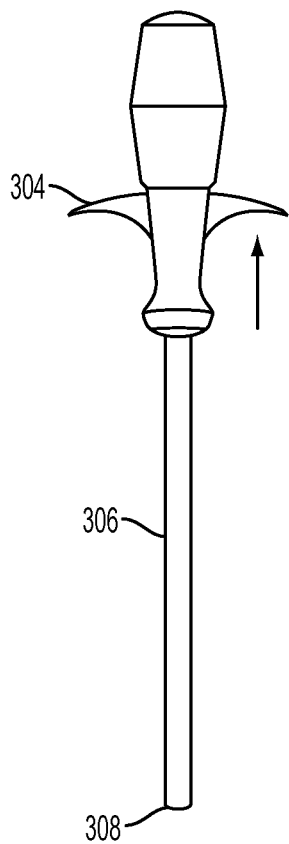
FIG. 17B is a side view of the inserter tool of FIG. 17A, showing a trigger pulled proximally to retract a distal fork into a distal end of an outer shaft of the tool.
Figure 17C:
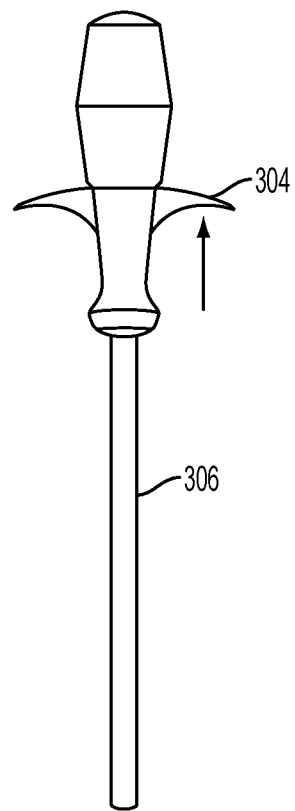
FIG. 17C is a side view of the inserter tool of FIG. 17B, showing the trigger pulled further proximally to release a guidewire from mating engagement with the inserter tool.

In one embodiment, the sheath inserter can be provided in multiple sizes that correspond to the size of the tendon and the anchor. FIGS. 16A and 16B illustrate the sheath inserter of FIGS. 10 and 11A, with FIG. 16A showing a size small sheath inserter tool 300s and FIG. 16B showing a size large sheath inserter tool 300l, as is evident from the increased size of the outer shaft 306l and the fork 308l. FIGS. 17A-17C illustrate use of the inserter. In FIG. 17A, the fork 308 is in the initial resting position, extending from the outer shaft 306. In FIG. 17B, the fork 308 is shown fully retracted into the outer shaft 306, with the trigger 304 moved proximally through the first range of motion. FIG. 17C shows full retraction of the fork 308 inside the outer shaft 306, and illustrate that further proximal movement through the second range of motion can release the guidewire 140. The sheath inserter tool 300 is preferably inserted percutaneously through tissue with the fork 308 in the fully retracted position.

Driver

Figure 18:
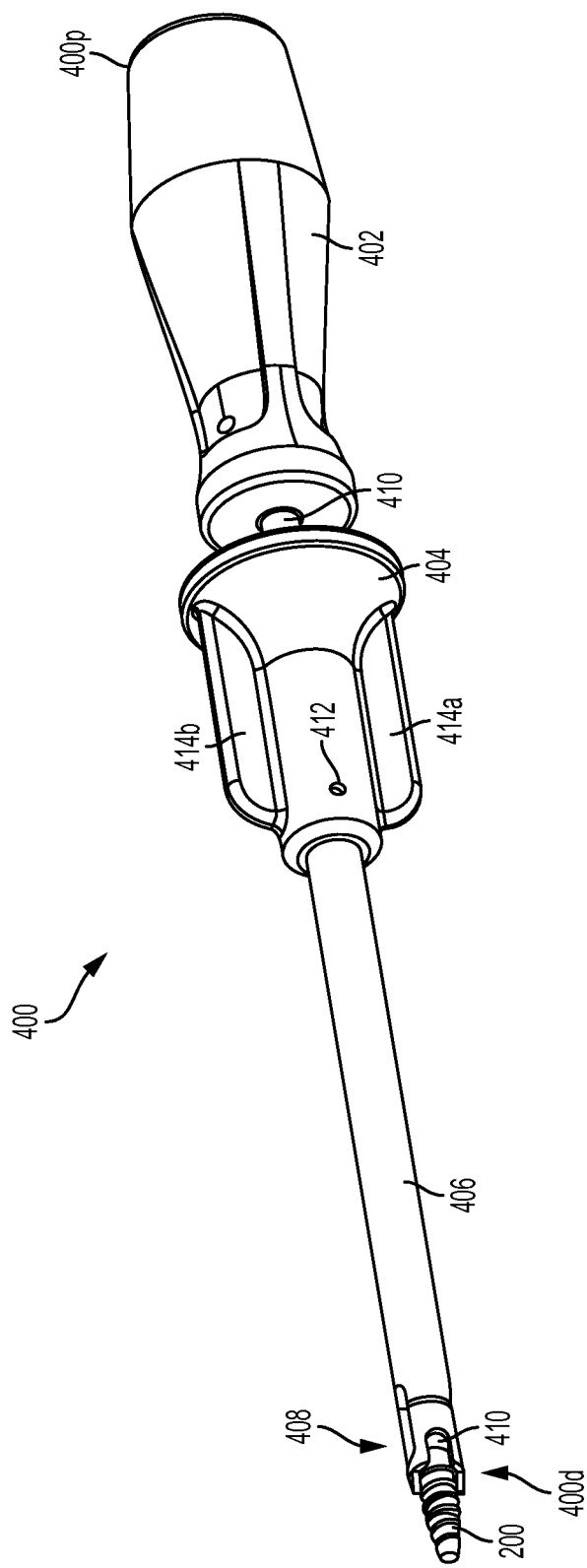
FIG. 18 is a side perspective view of the driver tool of FIG. 1.
Figure 19:
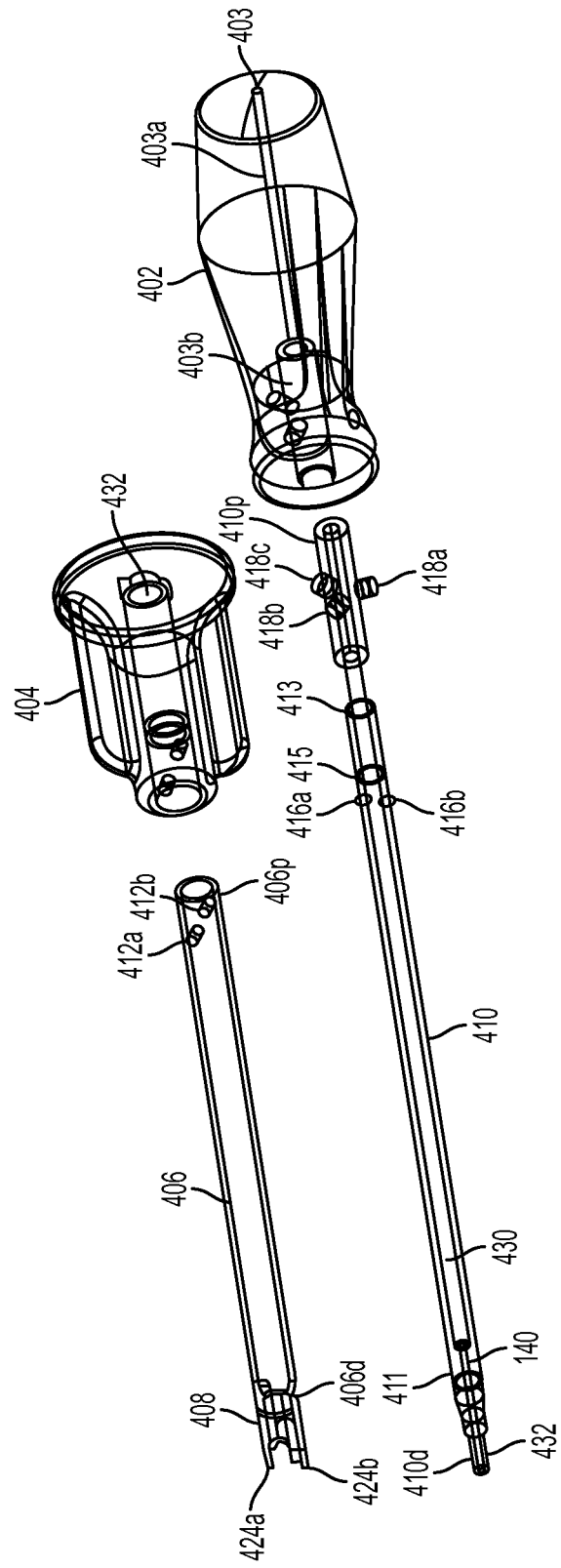
FIG. 19 is a transparent exploded view of the tool driver of FIG. 18.
Figure 20:
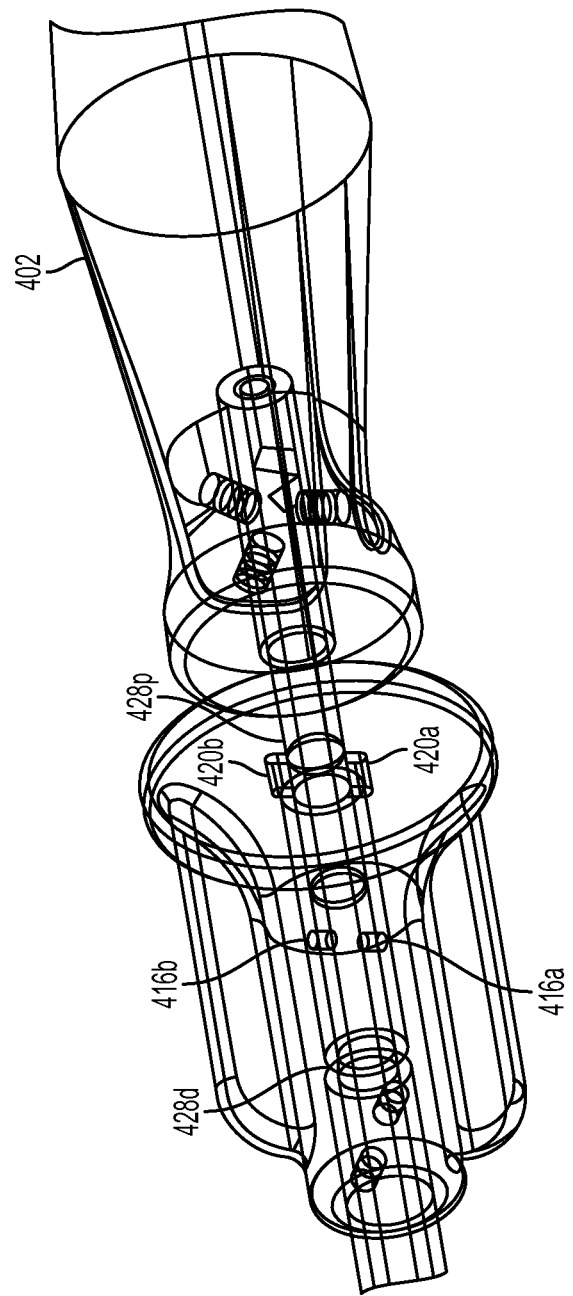
FIG. 20 is a transparent perspective view of a knob and a handle of the driver tool of FIG. 18.

Various driver devices are also provided for driving an expander into the sheath once the sheath is implanted in a bone hole. FIGS. 18 and 19 illustrate one exemplary embodiment of a driver tool 400. As shown, the driver tool 400 generally includes a driver handle 402 having an inner shaft 410 extending distally therefrom, and a knob 404 having an outer shaft 406 extending distally therefrom. The inner shaft 410 extends through the knob 404 and the outer shaft 406, with the driver handle 402 positioned proximal of the knob 404. An anti-rotation fork 408 is located on a distal end of the outer shaft 406 and can be configured to prevent rotation of the sheath 100 as the inner shaft 410 is used to thread the screw 200 into the sheath 100. The inner shaft 410 can include a guidewire channel 430 extending therethrough for allowing the guidewire 140 mated to the sheath 100 to be received therein.

The driver handle 402 and inner shaft 410 can have a variety of configurations. In the illustrated embodiment, the driver handle 402 has a generally elongate cylindrical configuration to facilitate grasping thereof. A bore 403 can extend through the handle and can include a proximal portion 403*a* that is sized to receive the guidewire and an enlarged distal portion 403*b* for receiving a proximal end of the inner shaft 410. The inner shaft 410 is preferably fixedly mated to or integrally formed with the driver handle 402. As shown in FIG. 19, the proximal end 410*p* of the inner shaft 410 includes mating screws 418*a*, 418*b*, 418*c* for securely and fixedly mating the inner shaft 410 to the driver handle 402. However other techniques, such as various mechanical engagement mechanisms, welding, adhesives, etc., can be used.

The inner shaft 410 can have a general elongate cylindrical configuration with a distal end 410*d* that is configured to mate to an expander, such as screw 200. For example, the distal end 410*d* can include a drive tip 432 formed thereon for engaging the screw 200. In the illustrated embodiment, the drive tip 432 has a hexagonal configuration for extending into a corresponding hexagonal drive socket formed in the screw to thereby allow the inner shaft 410 to rotate the screw 200. In other embodiments, other alternative shapes that non-rotatably mate can be used. The inner shaft 410 can further include a guidewire channel 430 extending therethrough for allowing the screw 200 and the inner shaft 410 to be slidably advanced over the guidewire 140 mated to the sheath 100, as will be discussed further below.

The knob 404 and outer shaft 406 can also have a variety of configurations, but as shown in FIGS. 18 and 19, the knob 404 is generally cylindrical with first and second opposed alignment indicators or tabs 414*a*, 414*b*. The tabs 414*a*, 414*b* can be aligned with prongs 424*a*, 424*b* on the anti-rotation fork 408, discussed below, to indicate the position of the prongs 424*a*, 424*b* to a user grasping the knob 404. The outer shaft 406 can have a generally elongate cylindrical configuration, with a proximal end 406*p* that is received within an inner lumen that extends through the knob 404. The proximal end 406*p* of the outer shaft 406 can be fixedly mated to the knob 404 using mating screws 412*a*, 412*b*, or other mating techniques.

As indicated above, the outer shaft 406 and the knob 404 can be slidably disposed over the inner shaft 410. In an exemplary embodiment, the outer shaft 406 and the inner shaft 410 are freely rotatably relative to one another, however longitudinal movement of the inner shaft 410 and the outer shaft 406 relative to one another is limited. As shown in FIG. 19, the inner shaft 410 can include stop pins 416*a*, 416*b* disposed thereon and protruding radially outward from opposite sides thereof. The stop pins 416*a*, 416*b* can be located just distal of the proximal end of the inner shaft 410. When the knob 404 is disposed over the inner shaft 410, the stop pins 416*a*, 416*b* can be positioned within the inner lumen 434 extending through the knob 404. The stops pins 416*a*, 416*b* and the knob 404 can be configured such that the stop pins 416*a*, 416*b* only allow the knob 404 to slide proximally and distally a predetermined distance. In particular, the knob 404 can include a reduced diameter region 428*d* adjacent the distal end that limits distal movement of the pins 416*a*, 416*b*, and a reduced diameter region 428*p* adjacent the proximal end that limits proximal movement of the pins. The proximal reduced diameter region 428*p* can, however, include opposed pin slots 420*a*, 420*b* formed therein for allowing the pins 416*a*, 416*b* to pass therethrough when properly aligned with the slots 420*a*, 420*b*. Such a configuration allows the knob 404 and outer shaft 406 to be removed from the inner shaft 410 and driver handle 402, e.g., for cleaning.

Figure 21:
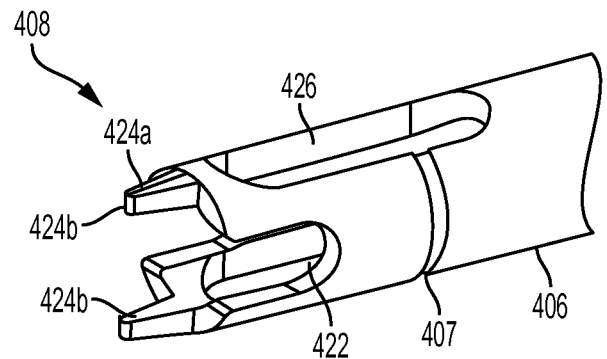
FIG. 21 is a perspective view of a distal end of an outer shaft of the driver tool of FIG. 18.
Figure 22:
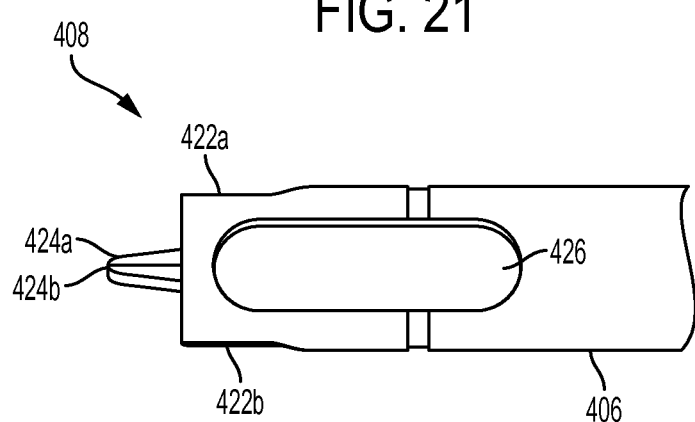
FIG. 22 is side view of the distal end of the outer shaft of FIG. 21.
Figure 23:
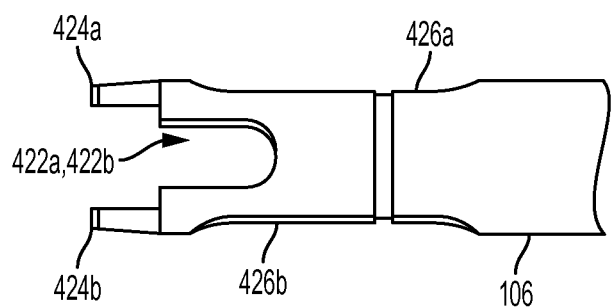
FIG. 23 is another side view of the distal end of the outer shaft of FIG. 21.

As indicated above, the distal end 406*d* of the outer shaft 406 can include an anti-rotation fork 408 having first and second opposed distal prongs 424*a*, 424*b* extending distally from opposite sides of the outer shaft 406. The prongs 424*a*, 424*b* can be configured to extend into the sidewalls slots in the sheath 100 to prevent rotation of the sheath 100 when the inner shaft 410 is rotated to drive the screw 200 into the sheath 100. FIGS. 21-23 illustrate the prongs 424*a*, 424*b* in more detail. As shown, each prong has a generally triangular configuration and extends from a semi-cylindrical sidewall. The prongs can thus extend into the slots in the sheath 100, while the sidewall abuts against a proximal end surface of the sheath. Such a configuration will limit insertion of the driver tool 400 into the sheath 100.

As further shown in FIGS. 21-23, the outer shaft 406 can also include features to facilitate viewing of the screw 200 coupled to the driver tool 400 and disposed within the outer shaft 406. For example, the outer shaft 406 can include one or more viewing windows or visibility windows 426 formed therein at a location adjacent to the distal end. The viewing windows 426 in the illustrated embodiment are in the form of elongate oval cut-outs formed through both sidewalls on opposite sides of the shaft and in alignment with the prongs 424*a*, 424*b*. However, the viewing windows can be at various locations and can have various configurations to allow for visibility into the inner lumen. As further shown, the outer shaft 406 can also include tendon cut-outs 422*a*, 422*b* positioned on opposed sides of the outer shaft 406 and offset from the prongs 424*a*, 424*b* and visibility windows 426 by about 90 degrees. The tendon cut-outs 422*a*, 422*b* can allow a tendon wrapped around the sheath 100 to protrude up into the cut-outs if needed.

Figure 24A:
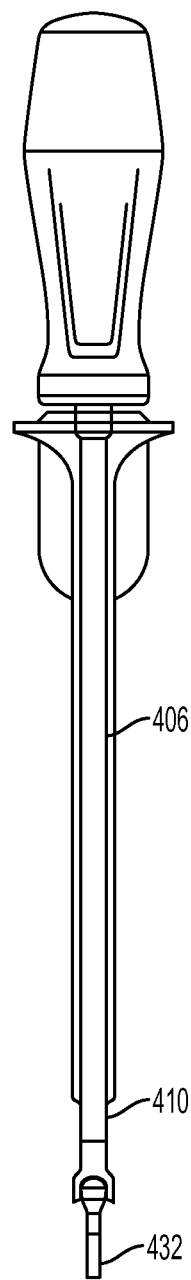
FIG. 24A is a side view of the driver tool of FIG. 1, showing the driver tool in an initial position.
Figure 24B:
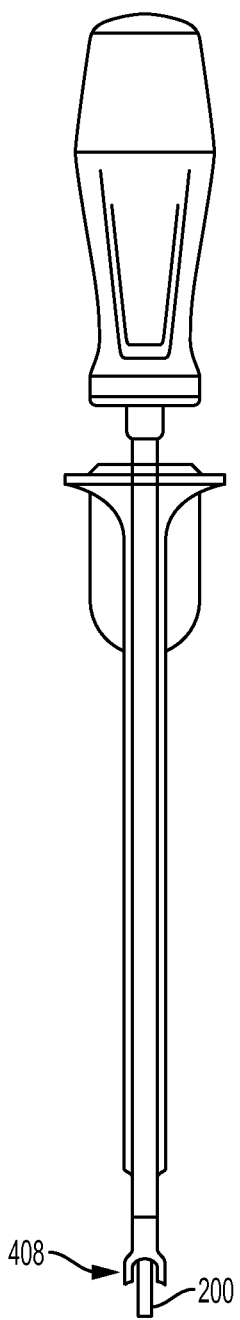
FIG. 24B is a side view of the driver tool of FIG. 24A, showing the outer shaft moved distally relative to the inner shaft.
Figure 24C:
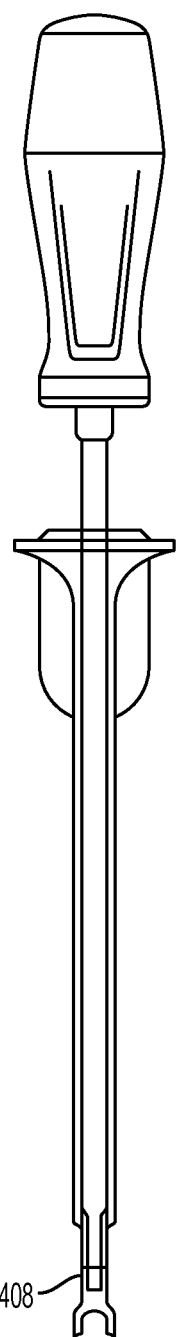
FIG. 24C is a side view of the driver tool of FIG. 24B, showing the outer shaft moved further distally relative to the inner shaft.

In use, as shown in FIGS. 24A-24C, the screw can be mated to the drive tip 432 on the inner shaft 410. The anti-rotation fork 408 can be advanced over the screw 200 such that the anti-rotation fork 408 can extend into the slots in the sheath 100 to prevent rotation of the sheath during insertion of the screw into the sheath. When the prongs are seated within the slots in the sheath, the driver handle 402 can be rotated relative to the knob 404 to thereby rotate the inner shaft 410 within the outer shaft 406. The inner shaft 410 will thus rotate and drive the screw 200 into the sheath 100 while the outer shaft 406 holds the sheath 100 stationary and prevents it from rotating. Such a configuration is particularly advantageous as it prevents rotation of the tendon, since the tendon is positioned around the sheath. Moreover, the anti-rotation fork 408 can also be effective to prevent the sheath 100 from backing-out of the bone tunnel during insertion of the screw 200. Without the anti-rotation fork 408, the tendon can have a tendency to pull the sheath out of the bone hole. The anti-rotation fork 408 can thus be used to push the sheath into the bone hole until the anti-plunge tabs on the sheath rest against with the bone surface.

The driver can also include markings to facilitate use. For example, one or more laser lines can be formed on the inner and/or outer shafts to indicate the position of the outer shaft relative to the inner shaft, thereby indicating the position of the screw relative to the sheath. In the illustrated embodiment, a first marking, in the form of a laser etched band 407, extends around the distal end portion of the outer shaft 406 on the inserter tool, as shown in FIG. 21. A second marking, in the form of a laser etched band 411, extends around the distal end portion of the inner shaft 410, as shown in FIG. 19. Alignment of the band 411 on the inner shaft with the band 407 on the outer shaft will indicate that the expander screw is fully driven into the sheath. A pair of markings can also or alternatively be formed on the proximal portion of the device. As shown in FIG. 19, the inner shaft 410 can include a pair of markings, in the form of laser etched bands 413, 415, that are located distal of the driver handle 402. The distal band 415 will align with the proximal end surface of the knob 404 when the device is in the initial configuration, prior to driving the expander screw into the sheath. The distal band 413, when aligned with the proximal end surface of the knob 404, will indicate that the expander screw is fully driven into the sheath.

Loader

The driver tool 400 can also optionally be used with a screw loader cartridge 500 to facilitate loading of the screw 200 onto the guidewire for delivering the screw into the sheath. FIG. 25 illustrates one embodiment of a screw loader cartridge 500. The screw loader cartridge 500 can be formed from various materials, such as metal or a molded plastic, and can have various shapes and configurations. In the illustrated embodiment, the screw loader cartridge 500 includes a proximal portion 500*p* with wings 502 formed thereon to facilitate grasping, and a distal portion 500*d* that is in the shape of a funnel 504 that is cut almost in half. The screw loader cartridge 500 can thus have a generally planer side as shown. An elongate channel 506 can be formed in the proximal portion 500*p* and it can extend toward the funnel 504 and can communicate with the funnel 504. The channel 506 can be shaped to seat the screw 200 and optionally a distal portion of the driver tool 400, including the anti-rotation fork 408. For example, the screw loader cartridge 500 can seat the screw 200 and the anti-rotation fork 408 on the outer shaft such that the outer shaft is in its proximal-most position and prevented from further movement. Such a configuration can help prevent rotation and axial translation of the driver tool inner and outer shafts when the loader and expander are mated thereto. This can be particularly desirable for packaging and preventing movement during shipping until use of the device. The screw 200 can be held within the channel 506 by press fit or using other techniques known in the art. When the screw 200 is seated within the channel 506, the guidewire channel (not shown) extending through the screw 200 can align with the opening of the funnel 504. In use, the guidewire can thus be inserted into the funnel 504, which will thereby guide the guidewire into the screw 200 for ease of insertion.

FIGS. 26A-26D illustrate use of the screw loader cartridge 500 for loading the screw onto the guidewire. FIG. 26A is a side view of the screw loader cartridge 500, showing the screw 200 seated therein. As shown in FIG. 26B, the screw 200 can simply be side-loaded into the channel 506. As shown in FIG. 26C, the funnel 504 can receive and guide the guidewire 140 into the screw 200. As shown in FIG. 26D, once the screw 200 is advanced along the guidewire 140, the tabs 502 on the screw loader cartridge 500 can be grasped and used to pull back on the screw loader cartridge 500 and disengage the screw loader cartridge 500 from the screw 200. The loader can be discarded or optionally sterilized and reused. The components can optionally be shipped with the screw and loader pre-loaded onto the screw driver tool.

Tendon Sizer

Figure 27A:
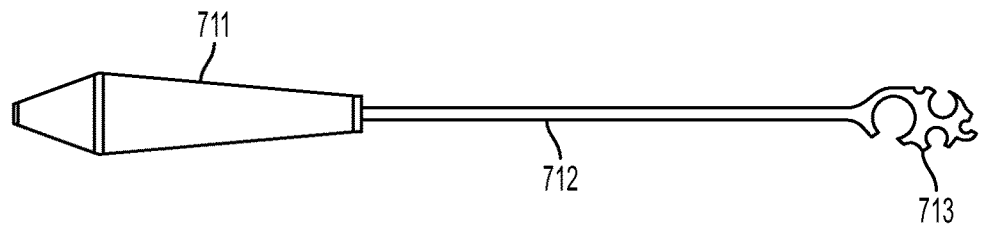
FIG. 27A is a side view of one embodiment of a tendon measuring device.
Figure 27B:
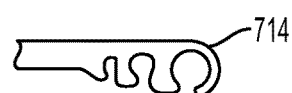
FIG. 27B is a side view of a distal end of another embodiment of a tendon measuring device.

As explained above, the fork on the inserter can be used to measure a size of a tendon to be anchored. In other embodiments, a separate tool can additionally or alternatively be used to measure a tendon. FIGS. 27A-31 include various embodiments for measuring the size of a tendon. In the embodiment of FIG. 27A, the tendon sizer 710 generally includes a handle 711 with a shaft 712 extending distally therefrom. A distal end of the shaft 712 includes a sizer 713 having various cut-outs formed therein, each with a different size. A tendon can be positioned within each cut-out until the size of the tendon matches the size of the cut-out. Markings (not shown) can be provided on the tool to indicate either the size of the tendon, or the size of the implant and tool set to use in connection with a tendon anchoring procedure. FIG. 27B illustrates a similar sizer 714, however the cut-out are aligned axially along the distal end, rather than positioned in a circular orientation as in the FIG. 27A embodiment.

Figure 28:
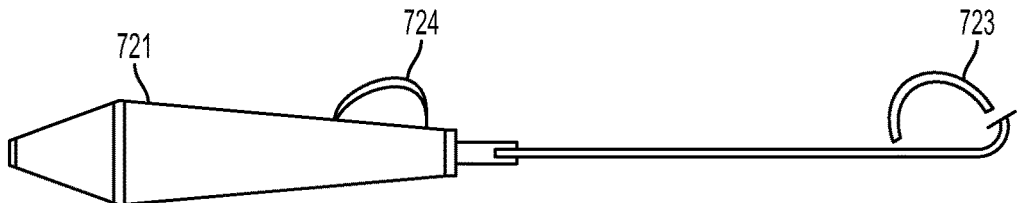
FIG. 28 is a side view of another embodiment of a tendon measuring device.

FIG. 28 illustrates another embodiment of a tendon measuring device 720 that is similar to the device of FIG. 27A, but that includes a retractable wire loop 723 on a distal end thereof. A knob 724 on the handle 721 can be slid proximally and distally to adjust a size of the loop 723. A tendon can thus be positioned within the loop, and once adjusted to match the size of the tendon, the device can indicate the size to the user.

Figure 29:
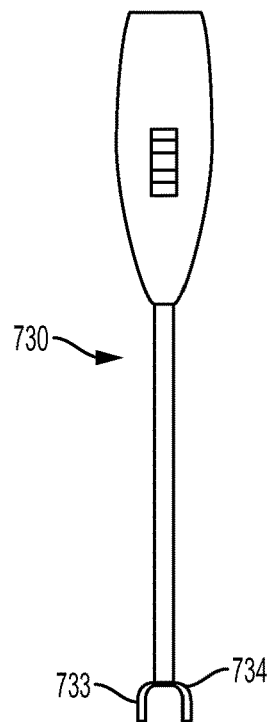
FIG. 29 is a side view of another embodiment of a tendon measuring device.
Figure 30:
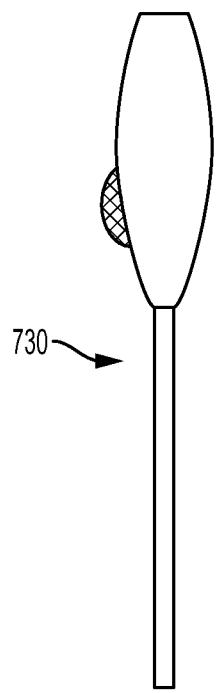
FIG. 30 is another side view of the tendon measuring device of FIG. 29.
Figure 31:
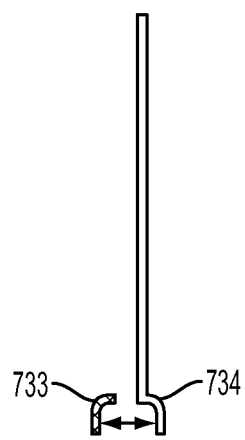
FIG. 31 is a side view of a distal end of the tendon measuring device of FIG. 29.

FIGS. 29-31 illustrate another embodiment of a tendon measuring device 730 that is similar to the device of FIG. 28, but rather than an adjustable wire loop, device 730 includes an adjustable arm 733 that moves with respect to a stationary arm 734 to allow a size of a tendon to be measured.

Figure 32:
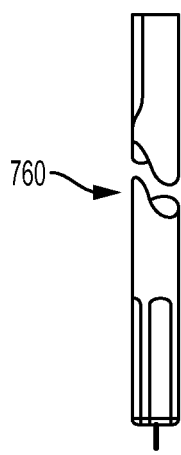
FIG. 32 is a side view of a combination guidewire and bone hole drilling device according to another embodiment.
Figure 33A:
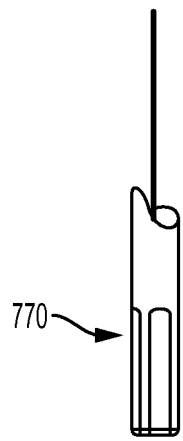
FIG. 33A is a side view of an embodiment of a combination tendon measuring and bone hole drilling device, showing a fork retracted within the distal end.
Figure 33B:
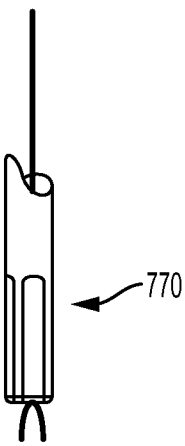
FIG. 33B is a side view of the device of FIG. 33A, showing the fork extended partially from the distal end.
Figure 33C:
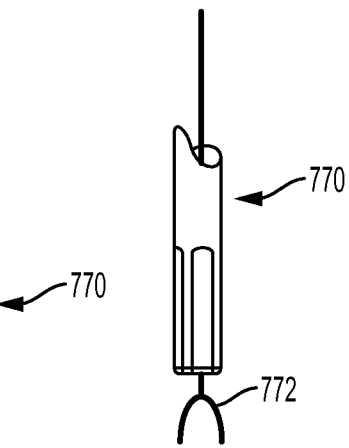
FIG. 33C is a side view of the device of FIG. 33A, showing the fork extended fully from the distal end.

In other embodiments, a combination tendon measuring device and bone hole preparation device are provided. FIGS. 32-33C illustrate various other devices for determining tendon size and/or for reaming a bone hole. In FIG. 32, a combination guidewire and bone reamer tool 760 is provided. In general, the device has a shaft with a distal end in the form of a reamer for reaming a bone hole, and a guidewire extends through the shaft. FIGS. 33A-33C illustrate a device that is similar to the device of FIG. 32, but that is in the form of a combination reamer and sizer tool 770. In particular, the reamer includes a forked sizer 772 slidably disposed therein. As the forked sizer 772 is extended from the distal end of the reamer, the fork expands in size for measuring tendons of differing size. The device can include markings or other features on a proximal end (not shown) for indicating the size of the measured tendon and/or the size of the implant and tool set to be used with the tendon.

Figure 34A:
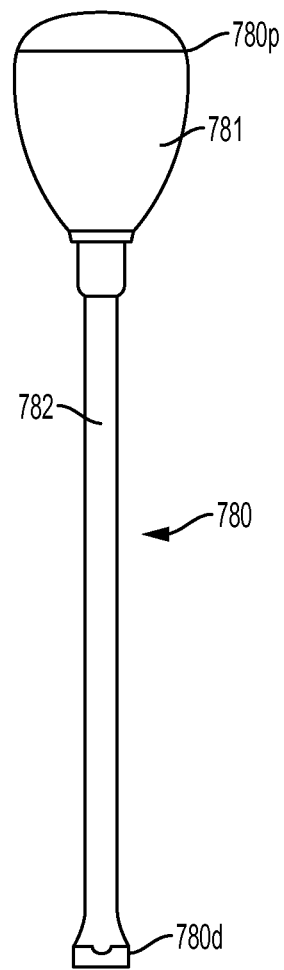
FIG. 34A is a side view of another embodiment of a tendon measuring device.
Figure 34B:
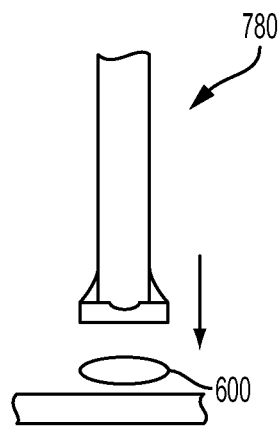
FIG. 34B is a side view of a distal portion of the tendon measuring device of FIG. 34A, shown positioned adjacent to a tendon to be measured.
Figure 34C:
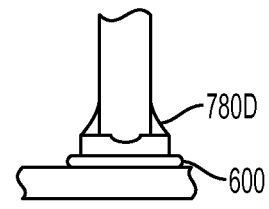
FIG. 34C is a side view of the distal portion of the tendon measuring device and the tendon of FIG. 34B, showing the measuring device measuring the tendon.

In another embodiment, as shown in FIG. 34A-34C, a tendon measuring device 780 is provided having a tamp 780 for measuring a tendon size. The device 780 includes a handle 781 having an elongate shaft 782 extending distally therefrom with the tamp 780 formed on the distal end thereof. In use, the tamp 780 can be inserted and pressed down on the bicep tendon in the ream and dunk location, as shown in FIGS. 34B-C. If the tendon compresses to a width of the tamp 780, the tendon requires a small scheme tool and implant set. If the tendon compresses and it is larger than the tamp 780, as shown in FIG. 34C, then it requires a large scheme tool and implant set.

Figure 35:
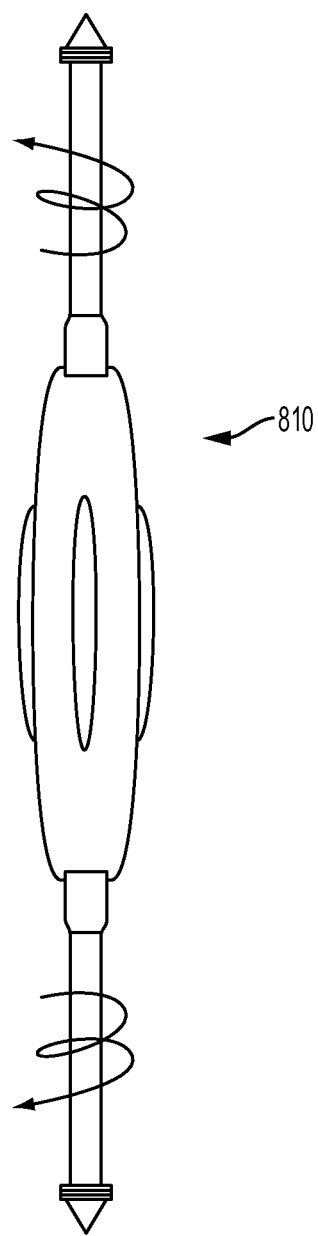
FIG. 35 is a top view of another embodiment of a bone hole preparation device.
Figure 36:
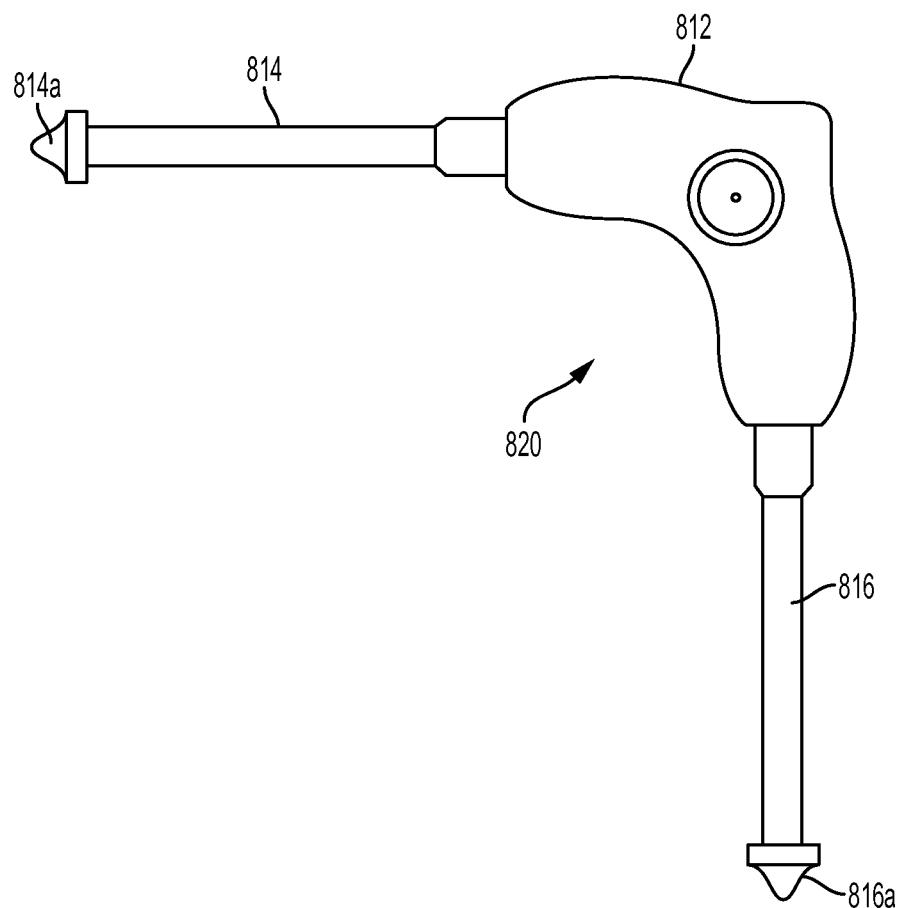
FIG. 36 is a side view of the bone hole preparation device of FIG. 35.
Figure 37:
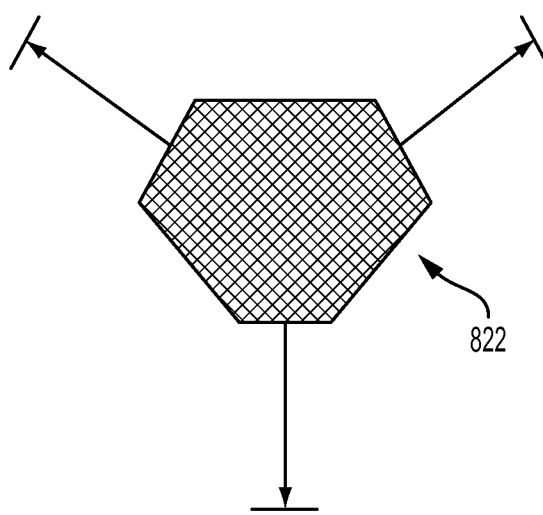
FIG. 37 is an end view of a tip of the device of FIG. 35.
Figure 38:
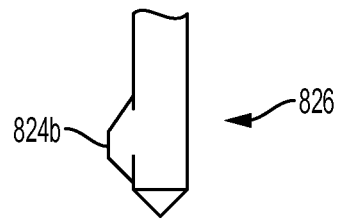
FIG. 38 is a side view of one embodiment of an angled tip of a bone hole preparation device.
Figure 39:
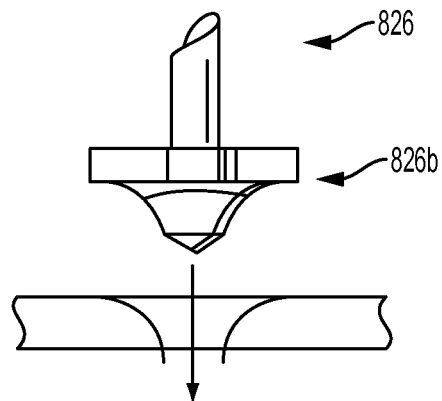
FIG. 39 is a side view of one embodiment of a rounded edge tip of a bone hole preparation device.

FIGS. 35-37 illustrate another embodiment of a device 810 that can be used to prepare a bone hole. The device 810 includes a generally L-shaped handle 812 having first and second shafts 814, 816 extending from opposed ends thereof. Each shaft can include a bone hole cutter 814*a*, 816*a* formed on a distal end thereof. While the shape of the bone hole cutters 814*a*, 816*a* can vary, in an exemplary embodiment, as shown in FIG. 37, each cutter can have a generally triangular configuration with truncated corners. One of the cutters, e.g., cutter 814a can have a first size and the other cutter, e.g., 816a can have a second size that differs from the first size. For example, the cutters can be provided in small and large sizes that correspond to small and large implant and tool sizes. The user can thus select the shaft and cutter having an appropriate size. As indicated above, the cutters can have a variety of configurations. FIGS. 38-39 illustrate additional cutter tip configurations for forming a bone hole having a desired shape. In FIG. 38, the cutter device 824 includes a tip having a protrusion 824b extending from a side thereof for forming a notch in a proximal end of a bone hole. The device can optionally include two protrusions for forming two notches. In FIG. 39, the cutter 826b on the device 826 has a configuration that forms a rounded edge at the top of the bone hole.

Method

The various implants and devices disclosed herein can be used to perform a variety of procedures in which it is desirable to anchor tissue to bone. FIGS. 40A-40E illustrate one exemplary method for performing a biceps tenodesis surgery. While the method is described in connection with the system of FIG. 1, a person skilled in the art will appreciate that the method can be performed using various anchors and tools, and that is can be performed for anchoring any tissue to any bone.

Figure 40A:
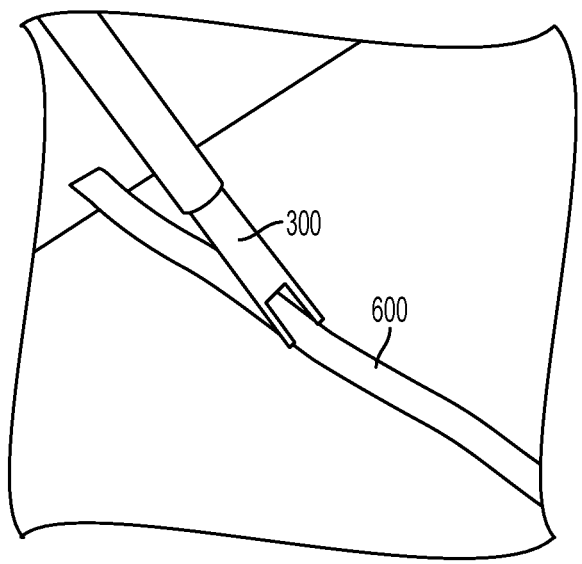
FIG. 40A is a perspective view of a distal portion of the inserter tool of FIG. 1, shown measuring a tendon to be anchored to bone.

In a biceps tenodesis procedure, a biceps tendon is retrieved, e.g., using suture, and a size of the tendon needs to be determined to allow a surgeon to select an appropriately sized implant and tools. This can be achieved using the sheath inserter tool 300. In particular, with the fork on the inner shaft fully retracted into the outer shaft, the sheath inserter tool 300 can be passed through tissue and positioned adjacent to the tendon and the implant site. As shown in FIG. 40A, the fork on the sheath inserter tool 300 can be manipulated to position the tendon 600 within the fork. If multiple inserter tools are provided, the smallest tool is preferably used first and the tendon is positioned between the forks on the distal end. If the tendon fits, then the implant (sheath and screw) that has a size corresponding to the size of the sheath inserter tool is used. If the tendon is too large and does not fit between the prongs on the fork, the next size inserter tool can be used to again measure the tendon. In an exemplary embodiment, a kit is provided having a small and a large sheath inserter, a small and a large implant (sheath and screw), and a small and large screw driver and loader. After properly sizing the tendon, the proper size reamer can be used to ream a bore in the bone, e.g., the humorous.

Various bone hole preparation devices can be used. During a biceps tenodesis procedure, improper preparation of the bone hole including rough or uneven edges can cause damage to the tendon including tearing or trauma. In some embodiments, a dual or triple ended tool can be used that will break the edge of the bone opening with a quarter turn back and forth. For example, the tool of FIGS. 35-36 can be inserted percutaneously, and the appropriately sized tip can be selected, inserted into the bone hole, and rotated by hand to form a bone hole opening as shown in FIG. 37. Alternatively, the device of FIG. 38 or FIG. 39 can be used to create an angled surface within the bone hole. The angled surface can provide an alternate means of bone hole preparation that can mitigate the potential for the tendon to rip or tear on a sharp edge of the bone.

Figure 40B:
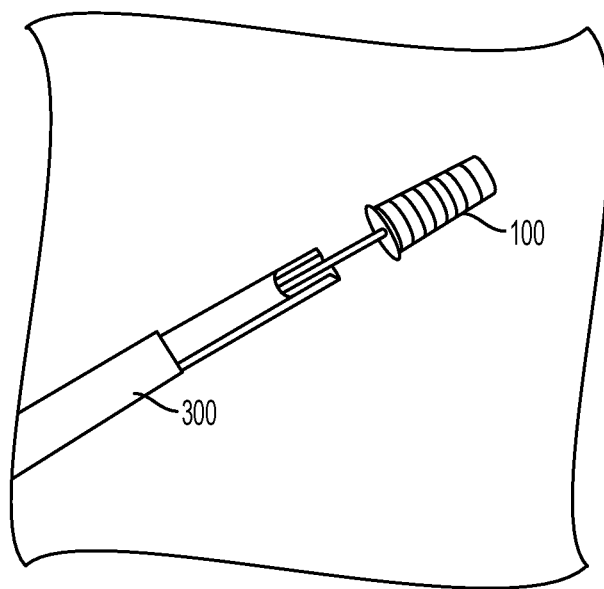
FIG. 40B is a perspective view of the distal portion of the inserter tool of FIG. 40A with the sheath of FIG. 1 being loaded onto the inserter tool.

After the bone hole is prepared, the tendon can be plunged into the bone hole using the appropriately sized inserter tool. The sheath and guidewire can be loaded onto the inserter tool prior to plunging the tendon. As shown in FIG. 40B, the guidewire 140 can be threaded into the inner bore in the sheath 100, which can be loaded into the distal end of the sheath inserter tool 300. This can be achieved by advancing the proximal end of the guidewire 140 into the distal end of the sheath inserter tool 300, and moving the guidewire 140 proximally until the guidewire 140 is press-fit into the guidewire retainer in the handle. The guidewire and sheath, or the guidewire, sheath, and inserter tool, can optionally be pre-packaged together in a mated configuration.

Figure 40C:
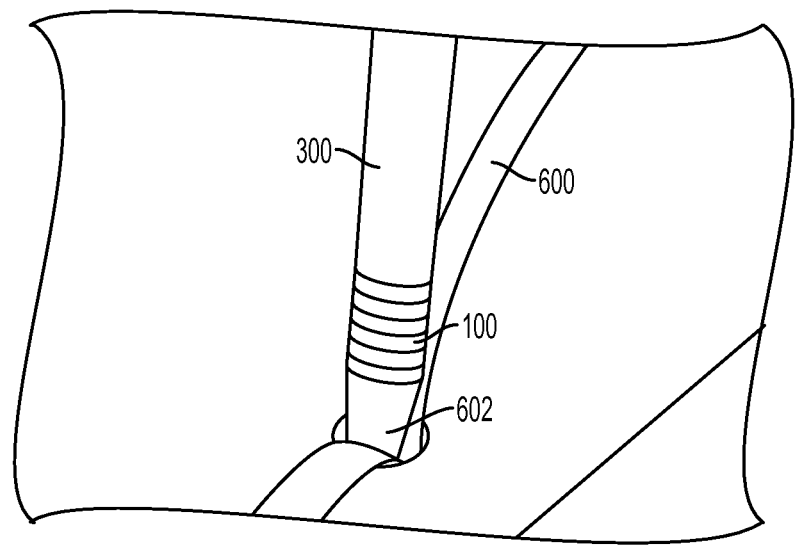
FIG. 40C is a perspective view of the inserter tool and sheath of FIG. 40B, showing the assembly being used to dunk a tendon into a bone hole in bone.
Figure 40D:
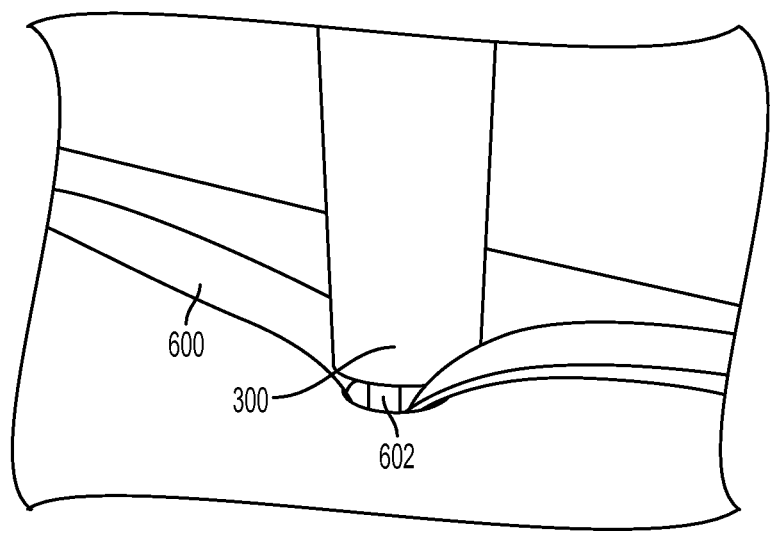
FIG. 40D is a perspective view of the sheath and inserter tool of FIG. 40C, showing the sheath fully inserted into the bone hole.
Figure 40E:
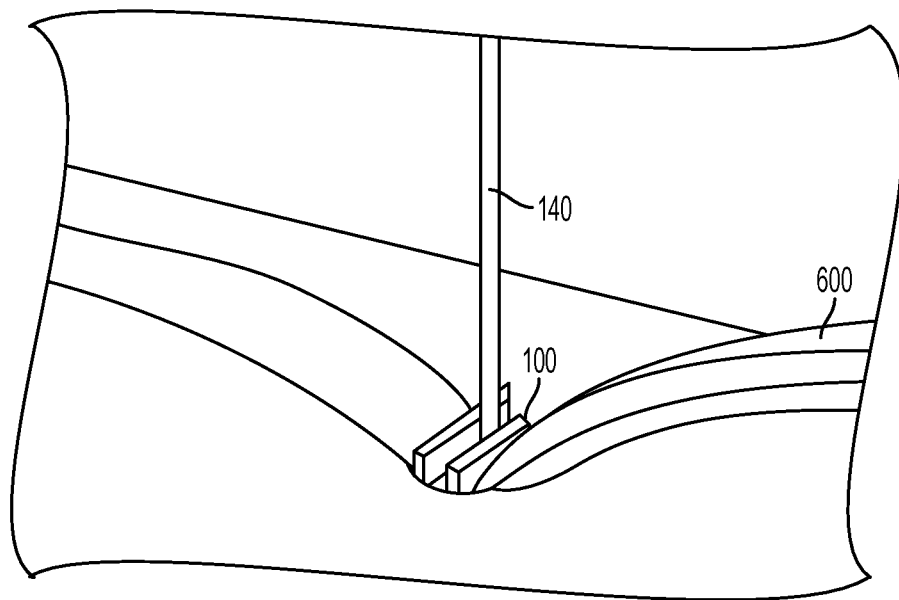
FIG. 40E is a perspective view of the sheath of FIG. 40D, showing the inserter tool removed leaving the guidewire coupled to the implanted sheath.

FIGS. 40C-40E illustrates various steps of inserting the sheath 100 and tendon 600 into the bone hole 602. For example, the fork 308 can be retracted by pulling proximally on the trigger through the first range of motion to allow for percutaneous insertion through the skin. The tip of the sheath can serve as an obturator to pass the sheath and inserter tool through tissue. Once passed through tissue, the operator can release the trigger to allow the fork 308 to extend distally out of the outer shaft. The fork 308 can be position around the tendon 600. A suture can be used to tension the tendon, and the forks can be positioned proximal or distal to the hole with the tendon therebetween. The sheath will thus rest against the tendon. The fork 308, with the tendon therebetween, can then be slid toward the hole 602 and dunked into hole 602, as shown in FIG. 40C. The bone hole diameter can be sized to allow the fork 308 and the sheath to be easily inserted thereon. Some resistance may be encounter due to the tendon being wrapped around the sheath. Since the outer shaft of the sheath inserter tool 300 is oversized compared to the tunnel 602, the outer shaft will be prevented from entering into the bone hole 602. If resistance is encountered, the proximal end of the inserter tool can be tapped with a mallet. The cortical bone is typically only 1 mm to 2 mm thick. When tapping with mallet, the goal is to tap the cortical retaining tabs into the hole until the anti-plunge tabs on the sheath 100 abut the bone surface such that over insertion of the sheath into the hole is prevented. The cortical retaining tabs are preferably sized so as to not cut through the bone when inserted therethrough. During the insertion process, the fork 308 can continue to straddle the tendon 600 all the way into bone 602. When the sheath 100 is fully inserted, the anti-plunge tabs and the distal end of the outer shaft will rest against the bone, as shown in FIG. 40D, and the cortical retaining tabs will extend below the cortical bone. The sheath inserter tool 300 can be removed by pulling the trigger through the first range of motion to retract the fork, and further proximally through second range of motion to thereby release the guidewire 140 from the handle. The sheath inserter tool 300 can then be slid off of the guidewire 140, leaving the sheath 100 in the bone hole 602 with the guidewire 140 extending therefrom, as shown in FIG. 40E.

Figure 41A:
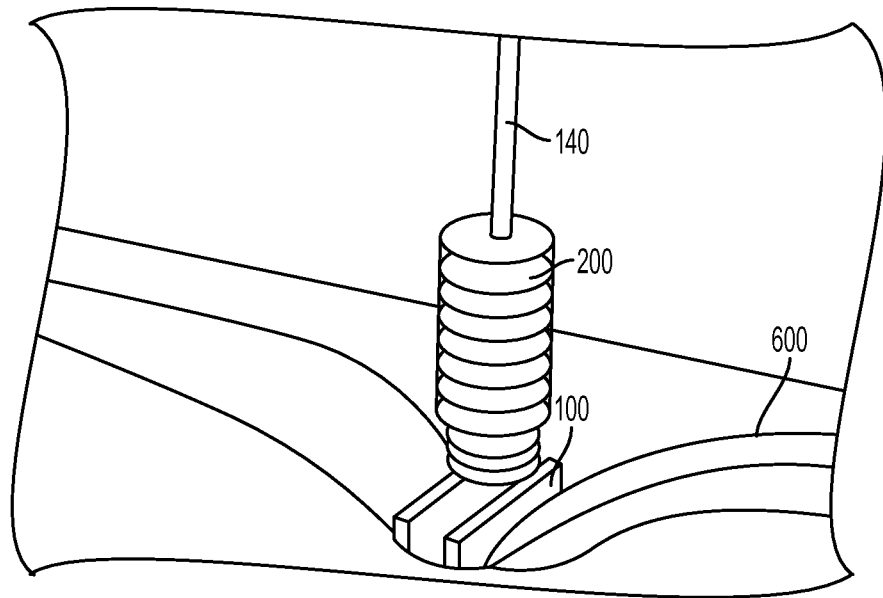
FIG. 41A is a perspective view of the expander screw of FIG. 1 loaded onto the guidewire of FIG. 40E.
Figure 41B:
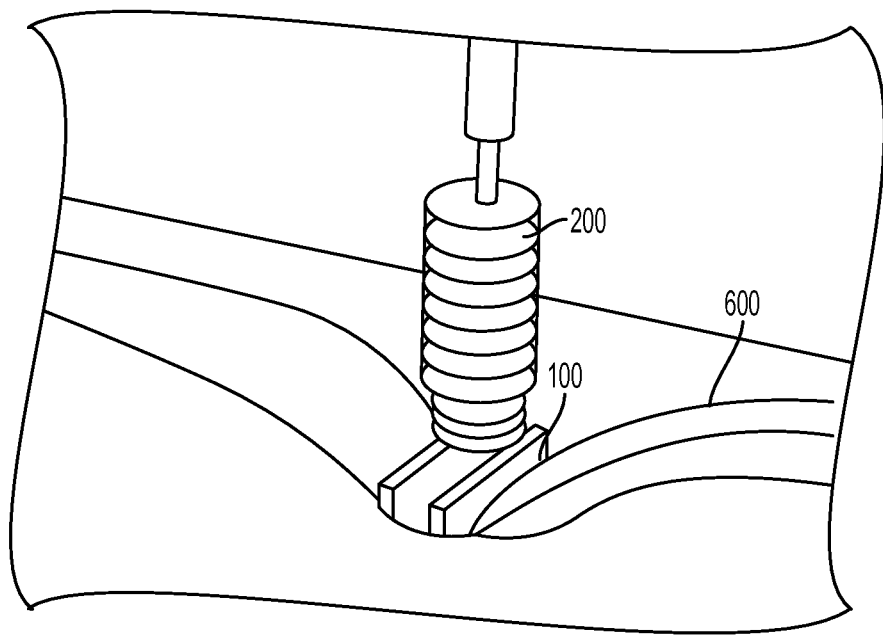
FIG. 41B is a perspective view of the expander screw of FIG. 41A, showing the driver tool of FIG. 1 being advanced over the guidewire.
Figure 41C:
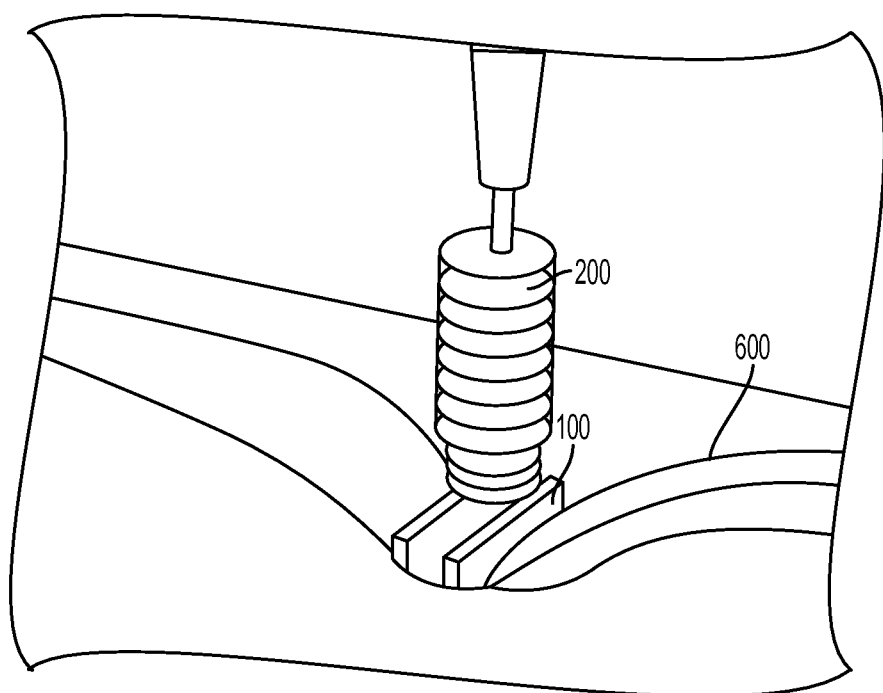
FIG. 41C is a perspective view of the driver tool and expander screw of FIG. 41B, with the driver tool engaged with the expander screw.
Figure 41D:
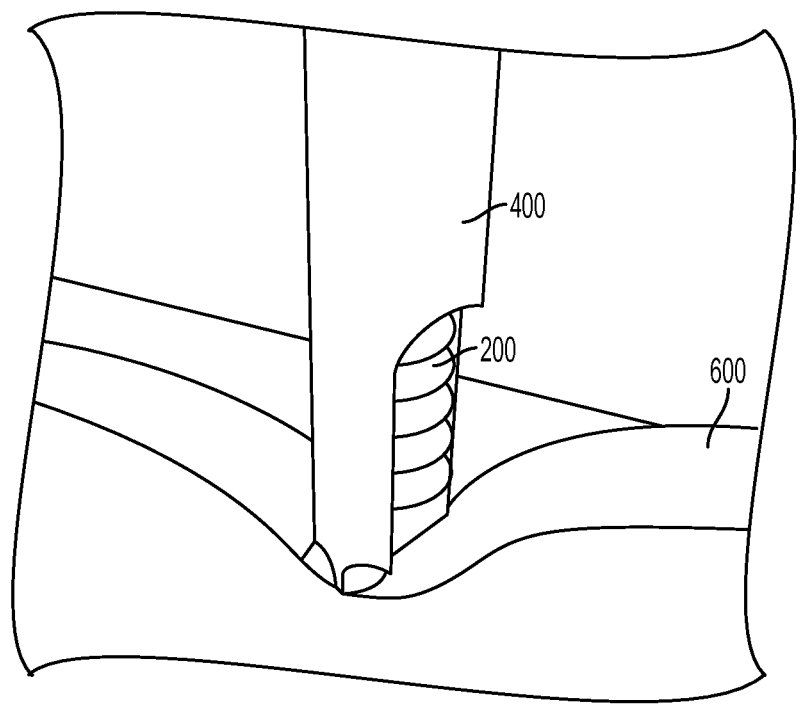
FIG. 41D is a perspective view of the driver tool and expander screw of FIG. 41C, showing an outer shaft of the driver tool advanced distally to position prongs on the outer shaft within slots in the sheath.

Once the sheath inserter tool 300 is removed, the screw 200 can be driven into the sheath 100 using the driver tool 400. The screw 200 can be loaded onto the driver tool 400 using the loader cartridge, or as indicated above the screw, loader, and driver can be pre-packaged in a fully assembly configuration. As discussed above, the loader tab has a funneled distal tip to assist in positioning the guidewire into the screw 200. The funnel can thus be advanced over the guidewire that is attached to the implanted sheath. The funnel will thereby guide the guidewire into the screw, which can be slid a distance down the guidewire. If desired, the screw driver can be advanced over the guidewire in conjunction with the screw. The loader can then be removed, and the driver tool 400 can be used to advance the screw 200 into the sheath 100, as shown in FIGS. 41A-41C. The prongs on the outer shaft of the driver tool 400 will extend into the slots in the sheath 100, as shown in FIG. 41D. The driver tool 400 can hold the sheath 100 within the bone hole 602, preventing back out during screw 200 insertion. The viewing windows opposite one another and aligned with the tines can facilitate viewing of the screw, and the side cut-outs offset from the viewing windows can receive the tendon so as to allow outer shaft to rest against sheath, as shown in FIG. 41D. In some embodiments, the outer shaft could be formed from a transparent material to allow viewing therethrough.

Figure 41E:
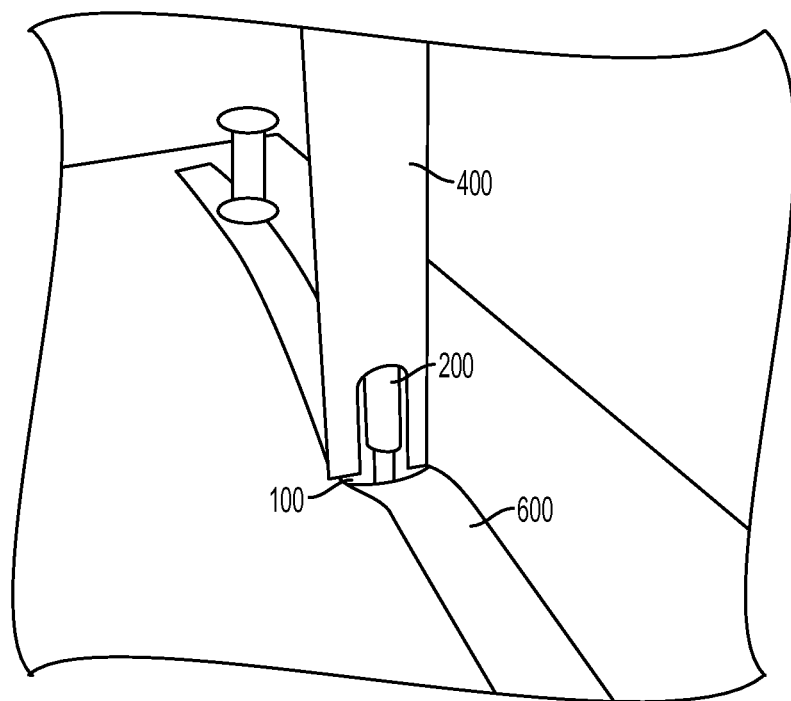
FIG. 41E is a perspective view of the driver tool and expander screw of FIG. 41D, showing the expander screw fully driven into the sheath.
Figure 41F:
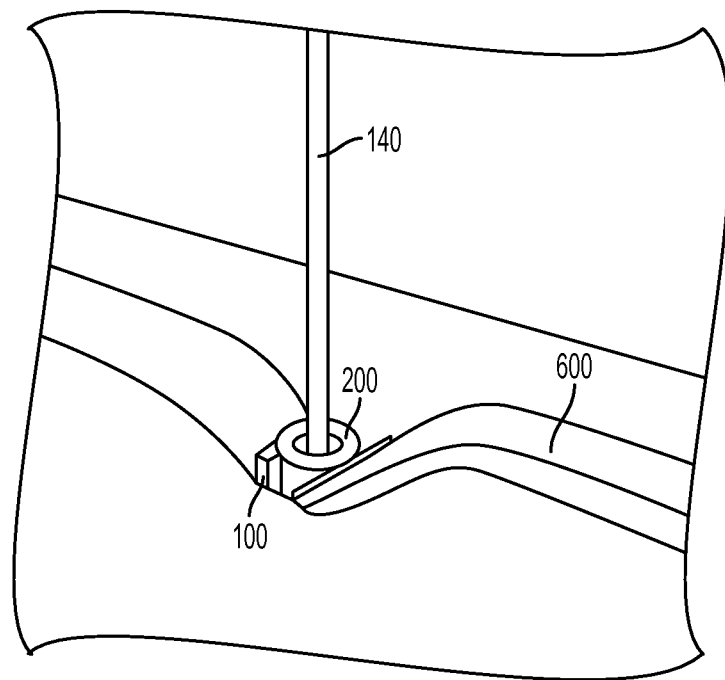
FIG. 41F is a perspective view of the driver tool and expander screw of FIG. 41E, showing the driver tool removed, leaving the guidewire extending from the expander screw disposed within the sheath.
Figure 41G:
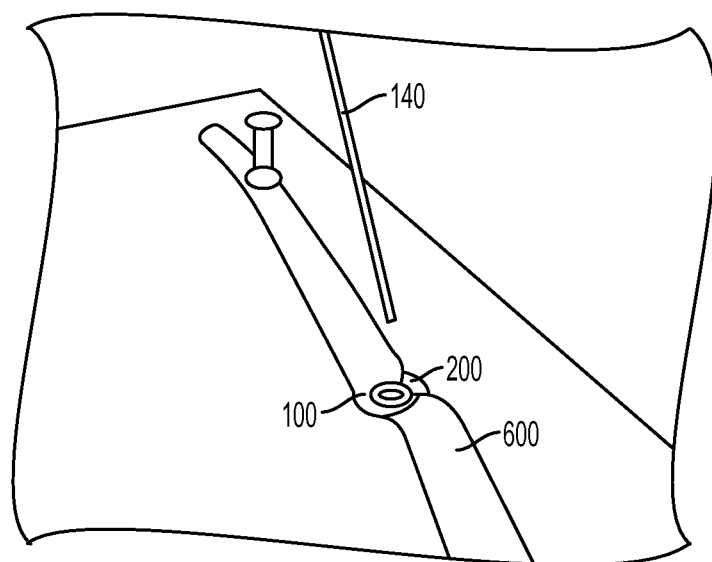
FIG. 41G is a perspective view of the sheath and expander screw of FIG. 41F, showing the guidewire being removed from the implant.

Once the driver tool 400 is seated with the outer shaft resting against bone, the outer shaft handle is held stationary while the inner shaft knob is rotated to drive the screw 200 into the sheath 100, as shown in FIG. 41E. In one embodiment, as discussed above, the shaft can have two laser lines, one on the inner shaft the other one on the outer shaft. When they are aligned, the screw 200 will be fully inserted. The proximal end of inner shaft can also have a line that will align with the knob on the outer shaft to indicate full insertion of the screw 200 into the sheath 100. The line can be particularly useful when the procedure is done without a scope (e.g., sub-pec during mini-open procedure). When the screw 200 is fully inserted into the sheath 100, the screw will cause the sheath to expand radially outward to engage the tendon between the sheath and the bone hole, and to thereby anchor the sheath and tendon within the bone hole. The ribs on the outer surface of the sheath can engage bone to prevent back-out. The expanded mid-portion of the sheath, as well as the cortical retainer tabs, can also help retain the sheath within the bone hole. As shown in FIGS. 41F-41G, once the screw 200 is fully inserted into the bone hole, the driver tool 400 can be slid off of the guidewire 140. The guidewire 140 can be removed, e.g., by bending the proximal end and turning the guidewire 140, to unthread it from the sheath 100.

A person skilled in the art will appreciate that the biceps tenodesis methods and devices disclosed herein can be used in a variety of surgical procedures to trauma or damage to a tendon being attached to a bone via a bone hole. The present invention also has application in conventional joint repair surgeries.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An anchor assembly for anchoring a tendon to bone, comprising:
    a sheath having a substantially solid distal end with only two sidewalls extending proximally therefrom and separated by first and second slots, a width between the slots decreasing toward the substantially solid distal end, the sidewalls defining an inner lumen therebetween, and the solid distal end of the sheath having a mating feature, wherein the sheath includes at least one anti-collapse tab formed on at least one of the sidewalls adjacent to one of the first and second slots, the at least one anti-collapse tab being configured to limit movement of the sidewalls toward one another;
    a guidewire having a distal tip configured to releasably mate with the mating feature in the sheath, the guidewire extending proximally from the sheath when mated thereto; and
    an expander having a generally elongate cylindrical configuration, tapered distally along a distal portion, and configured to be received within the inner lumen of the sheath, the expander having a lumen extending therethrough for receiving the guidewire.

2. The anchor assembly of claim 1, wherein the mating feature comprises a threaded bore formed in the sheath and the distal tip on the guidewire is threaded for threadably engaging the threaded bore.

3. The anchor assembly of claim 1, wherein the sheath includes at least one anti-plunge tab extending radially outward from a proximal-most end thereof and configured to limit an insertion depth of the sheath into a bone hole.

4. The anchor assembly of claim 3, wherein the sheath includes at least one retaining tab extending radially outward from the sheath at a predetermined distance from the at least one anti-plunge tab, the distance being configured such that the at least one anti-plunge tab can be positioned on a proximal surface of cortical bone and the at least one retaining tab can be positioned on a distal surface of the cortical bone.

5. The anchor assembly of claim 1, wherein a distal-facing end of the sheath is concave for seating a tendon.

6. The anchor assembly of claim 1, wherein a proximal-facing end of the sheath is convex.

7. The anchor assembly of claim 1, wherein the sidewalls have an increased thickness at a mid-portion thereof as compared to proximal and distal portions thereof.

8. The anchor assembly of claim 1, wherein the sidewalls include ribs extending radially therearound.

9. The anchor assembly of claim 8, wherein the ribs on a first sidewall of the anchor are angled distally and the ribs on a second opposite sidewall of the anchor are angled proximally.

10. The anchor assembly of claim 1, wherein the sidewalls of the anchor have threads formed on an internal surface thereof, and the expander includes threads formed on an external surface thereof for threadably mating with the threads formed on the internal surface of the at least two sidewalls.

11. The anchor assembly of claim 1, wherein the first and second slots each have a proximal portion, a distal portion, and a transition region extending between the proximal and distal portions, the proximal and distal portions each having a constant width, and the transition region having a width that tapers inward in a distal direction.

12. The anchor assembly of claim 11, wherein a length of transition region is substantially equally to a width of the proximal portion.

13. An anchor assembly for anchoring a tendon to bone, comprising:
- a sheath having
  - a substantially solid end,
  - two sidewalls extending proximally from the distal end, the sidewalls being separated by at least two slots, a width between the slots decreasing toward the substantially solid distal end, and the sidewalls defining an inner lumen therebetween,
  - at least one anti-plunge tab extending from a proximal-most end of the sheath adjacent to at least one of the slots, the at least one anti-plunge tab preventing over-insertion of the sheath into a bone hole,
  - at least one retaining tab extending from the sheath at a location distal to the at least one anti-plunge tab, the at least one retaining tab being positioned a distance apart from the at least one anti-plunge tab, the distance being configured such that when the at least one anti-plunge tab is positioned on a proximal surface of a cortical bone, the at least one retaining tab will extend beneath a distal surface of the cortical bone,
- at least one anti-collapse tab formed on at least one of the sidewalls adjacent to one of the first and second slots, the at least one anti-collapse tab being configured to limit movement of the sidewalls toward one another; and
- an expander configured to be received between the at least two sidewalls on the sheath to cause the sheath to expand and engage bone.

14. The anchor assembly of claim 13, wherein the at least one anti-plunge tab comprises a pair of anti-plunge tabs, and the at least one retaining tab comprises a pair of retaining tabs.

15. The anchor assembly of claim 13, wherein the distance is greater than about 0.5 mm.

16. The anchor assembly of claim 13, wherein the at least one anti-plunge tab extends radially outward by a distance that is greater than a distance that the at least one retaining tab extends outward.

17. The anchor assembly of claim 13, wherein the at least one anti-plunge tab is co-planar with the at least one retaining tab.

* * * * *